United States Patent
Both et al.

(10) Patent No.: US 7,037,712 B2
(45) Date of Patent: *May 2, 2006

(54) DNA ENCODING OVINE ADENOVIRUS (OAV287) AND ITS USE AS A VIRAL VECTOR

(75) Inventors: Gerald Wayne Both, North Ryde (AU); David Bernard Boyle, Leopold (AU); Sadhanshu Vrati, New Dehli (IN)

(73) Assignee: Commonwealth Scientific and Industrial Research Organisation, Victoria (AU)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/464,767

(22) Filed: Dec. 16, 1999

(65) Prior Publication Data

US 2002/0045249 A1    Apr. 18, 2002

Related U.S. Application Data

(63) Continuation-in-part of application No. 08/776,274, filed as application No. PCT/AU95/00453 on Jul. 26, 1995, now abandoned.

(30) Foreign Application Priority Data

Jul. 26, 1994   (AU) .................... PM7101

(51) Int. Cl.
*C12N 15/861* (2006.01)
*C07H 21/04* (2006.01)
*A61K 35/76* (2006.01)
*A61K 48/00* (2006.01)

(52) U.S. Cl. .................. 435/320.1; 435/325; 435/456; 424/93.2; 536/23.1; 536/23.72

(58) Field of Classification Search ............ 435/320.1, 435/325, 455; 424/93.2; 514/44; 536/23.1, 536/23.7, 23.72
See application file for complete search history.

(56) References Cited

U.S. PATENT DOCUMENTS 6,020,172 A * 2/2000 Both ................. 435/91.41

OTHER PUBLICATIONS

Adair et al.: "Serological Identification of an Australian Adenovirus Isolate From Sheep", Australian Veterinary Journal, vol. 63, No. 5, 1986, p. 162.
Elgadi et al.: "Sequence and Sequence Analysis of E1 and pIX Regions of the BAV3 Genome", INTERVIROLOGY, vol. 36, 1993, pp. 113-120.
Shibata et al.: Nucleotide Sequence of E1 Region of Canine Adenovirus Type 2, VIROLOGY, vol. 172, 1989, pp. 460-467.
Salmon et al.: "Subcloning and Restriction Mapping of Bovine Adenovirus Type 2", INTERVIROLOGY, vol. 36, No. 2, 1993, pp. 72-78.
Vrati et al.: "Sequence of Ovine Adenovirus Homologs for 100K Hexon Assembly, 33K, pVIII, and Fiber Genes: Early Retion E3 is not in the expected Location", VIROLOGY, vol. 209, Jun. 1, 1995, pp. 400-408.
"Oligonucleotide probes for the screening of recombinant DNA libraries", by Wallace et al., Methods Enzymol. vol. 152, p. 432-442.
"Computational complexity, protein structure prediction, and the Levinthal paradox", by Ngo et al., The Protein Folding Problem and Tertiary Structure Prediction, Birkhouser Boston: Boston, MA, pp. 433 and 492-595.
Sambrook et al., Molecular Cloning, A Laboratory Manual, 2nd ed., Cold Spring Harbor Laboratory, Cold Spring Harbor, NY, pp. 11-47.
"Report and recommendations of the panel to assess the NIH investment in research on gene therapy", by Orkin et al., issued by the U.S. National Institute of Health.
"Facilitating oligonucleotide delivery: helping antisense deliver on its promis", by Gewirtz, et al., Proc. Natl. Acad. Sci. USA, vol. 93, pp. 3161-3163.

(Continued)

*Primary Examiner*—Scott D. Priebe
(74) *Attorney, Agent, or Firm*—McDermott Will & Emery LLP

(57) ABSTRACT

A genome of an ovine adenovirus designated OAV287 is isolated from sheep and sequenced. Portions of the genome not essential for maintenance or viability of the virus can be deleted or altered. A nucleotide sequence encoding a non-adenoviral polypeptide can be incorporated into the genome. The a full-length clone of the genome can be provided as part of a plasmid or viral vector. Cells can be transformed with a vector of the invention such that they express an exogenous protein.

20 Claims, 32 Drawing Sheets

OTHER PUBLICATIONS

"Toward gene-inhibition therapy: a review of progress and prospects in the fields of antiviral antisense nucleic acids and ribozymes", by James, Anitviral Chem. Chemother. vol. 2, No. 4, pp. 191-214.

"Ribozymes as human therapeutic agents", by Christofferson, et al., J. Med. Chem. vol. 38, No. 12, pp. 2023-2037.

"Adenovirus vectors as recombinant viral vaccines", by Imler, Vaccine vol. 13, No. 13, 1143-1151.

"Characterization of Australian Ovine Adenovirus Isolates", by Boyle et al., Veterinary Microbiology, vol. 41, No. 3 (1994), pp. 281-291.

"Synthetic Vaccines", by Nicholson, published by Blackwell Scientific Publications (Oxford, UK) pp. 346-361.

"In Vivo Adenovirus-mediated Gene Transfer to Lungs Via Pulmonary Artery", by Lemarchand et al., Journal of Applied Physiology, vol. 76, No. 6 (1994), pp. 2840-2845.

* cited by examiner

```
CTATTCATAT ATATAACGTT GCACACAGGC GGGGCGTGTG GGTTTTTTAT TGTTTATTGT    60
CATGGAATTT ACAAAGAAGT AAGTTGTTGG ATCTTTATTC ACAATTCTTT TAACAATGAC   120
TTTTTTACTT ATTACATTTT TCATCTTTTT TACTTCACAT GATATTTTAC TTAAATTTTG   180
TACATACAAG CCAAAATTCG CATAAAATGT CTTACTTTAA AAAGTTAAAT TTTTTTTTTA   240
ACGCATAAAT GGACGTACAG CAGCAATTGG AATAGCAGGA AGGGCCATTG TAAAGTGTGT   300
TCCTGCTGAT GCCGCTGCAG AAAGGATAGA TGCTATCGTA CGCATAAACC CCCCTCCTAT   360
TTGTTCATCT GCTGCTTTTA TTATATCTTC TGCCAATCTA GGTGATATTT GCTTTTGAAT   420
GCTGTTTCCA AAAGCTTGCA TCATCGGATT TTCAATTAAA TGGATTGGAT TTGCAGAATT   480
TCCTTAAAAA TAGCCCAACC CATCTAAAGC AGTTAAAAGT ATTCTCCCTC CAGGAACCAC   540
AGATATAATT AAGCGGAGCA ACCGAGAGGT TAAATTCCAG GGTCCTCCGA AGAGAGTATC   600
TAGGATCAGG CCAAGAAGTG AACCAAAAAG ACTTGTAAGT AGAAGTTGTC TGATATGGTT   660
TGGAGAGGAC TGTTAAAATT GCAAAACGGT ATCTAATGAC CATTTCTTCT TTACTTTTAC   720
ATCTGTATCA TGTTCTCCAT CAGAAGGTCT TATTGGGAAG TACCATTGGT CACGAGCATC   780
TTTGAAGACT TCTGTTTCTT GAAATTCTGT TTTCGGTAAG CGACTAGCAG TTATGGTATT   840
AGGAATATTG ACGGTAATGT TATTCACATC TACAATTTCT GGAGGAATCC ATCTTGCATA   900
GGATGAAATG GGTTTTGTGG GTTCTTTCAA TATATAATTG CGAGGAGGGT TTTTCCAAAA   960
TCTCTGAACA TAAGTATTTT CTGATTTTGG CGGTTTTTTG CTTTTTCGCG CTCTTTTTCT  1020
TGGCTTTGGT CTTTGAAATT TTTTCTTCCT TTTTCTGTAG GCTCCTCCTG CTAAAGCTGT  1080
GTTATTTGTG ACGTACATCC TGTTAGCTAC ACGATTTTCC CGGACTGCAA ATTTTTTTGC  1140
CAAATGGAAA AGAAATTGCT GAAACCTTCT ATTAATCATA TAATTTGTCA GTGGAATCAT  1200
GAATCAGATA GTGCAGGATT TTTTCTTTTT GATACTGATA ATTTATACTA TTATGTATTG  1260
GATCAAGTCT CTTGGATATG TTTAAGAGAT ATAACTCTTC ATTGTGATCG CATGTGGTTA  1320
GCGGTTTGTT TTTGTTTGTG CAAATCTAAA TTTGATGTAC ACAATATTCT AGCGGGAGTA  1380
CATGTTATGT AATGAAAATG ACGTCGGGGA TTGAATGGAT TGAGCCTTAT TTGACATTTT  1440
TCTGTGATTT TTTTGCCTTA TTAGGAAATA AATTTGTGGC GCCAGTACGA TGGAGATTGG  1500
AATGACTCCT GCATTTACAG AAAGGAATTT GTACTGTGTT TTGCTTGACT TTAATTTAAG  1560
ATGGTATCAG CAGATATTTA ACCCAATATG GATTAAGCCA AATTTATGGG CTTTCTCTGA  1620
TTTTTAAAA AAAATGGCCT TTATTTATGC TAGCGACTTG GCGTTGTTAA ATTCTTACAT  1680
CCCTGGTAAT GTTTGTAACA AACTTGATAT CATCAAGAAA GATCTTCCTG AAGATTTTAC  1740
CGTGTCTATG TTTTGTGTCT TAGTGTGTTG GCTTGCTTCT TTCTGTAAAG GTTCTAATTT  1800
AGCTGAAACT CGCCAGAATT GTCACGCGGT AAGCAAATTT CTGGCACAAC TATCAAAATT  1860
AATAAAACCC TAATTTTTAG TTTGTAAAAA TAGAATTCAA ATTTTTAACG CCACAATGAC  1920
TTCGGCCGAG TTTTCTGTTG AATTTCCTTA TGTTTCTAAG CCAATTGTTC CATGGCCTGC  1980
TTCGGCATCT TCTAATAATT CATCGAGTCA GAATATTGAC TTTCCTGTTC TTAAACCAGA  2040
TCAAGATCCA ATAGCCTTCT TTCAAACTAA CAATACGGCT TACTTACAAC CTGGAGCTAC  2100
TTATTACTGG AAGTGTATCG AACTGTCAAA GCCTATTCAC ATTTACGGTC AAGGAGCTAC  2160
AGTACAACTT GTCGGACCTG GACCTGTGTT TGTTTTCAAC AGTGAAAGTG TTATTCCTGA  2220
AGATTTTTAC GTCGTGTTTG AAAATATCAA CTTTATTGAA GATGAATTTC CTATTAGAAG  2280
TGGCCAGTTA AGTTTAGGAC TTACAACTCA CAGTGCTGTA TGCTTTATCA ATGTATGGAA  2340
AACTTCAATA GTCAATTGTA ACTTTAAAAA TTTAGGGGA GCGGCTCTTT GGTATTCAGA  2400
TAATAGAAAT TTTTGGAATG CGAGAAAATG GAATCAGCAG CATTTAGTTT CAAATTGTCG  2460
TTTTAATGGT TGTAGAATTG GAATTTCTAA TACTGGTTCA TCTGAATATT CCATAGCCAG  2520
TCAAAATCAA TTTTATGATT GTCAAATCTG TTTTAATGTA ACGGGGGTA ATTGGTCTAG  2580
AAATAATAAT GTTATTGTTA ACTGTAGATG TGCTTATCTG CATGTTGGAG ATAACATGTG  2640
GTATGAAGGC CATTCCGAAA ATAATAATCC CGCTAAGGGT ACTTCTGCA ATAACATAAT  2700
TAACCATGCT GATAACGGAG GCAATGTCTG GCCTACTCAG TTTAAAGTTA CAGATGGATC  2760
AACGATACAG TTAGCATCAT TTTATTTTGA TGATAATCAA GAAATTCCAC CTTGTTATAG  2820
CGGTAATTTT CATTGGTTTG GAGATGTAAA CATTGTAAAT TTTCTACCA CAAAATTGA   2880
TAAATGGTGC ATTACTGGAT GTAATTTCTA TGGTAATACA CATCAGCTA ACGATGCTGG   2940
TCAAGTTCAG GTTGCTGAAG CTGTAAAAGA CAAAGTGTTT ATTATTGGGT GTTCTGGTAA  3000
TAATGTAACC ATGAAAAATA TTGTAGAAGG TAACATGACT CCAAAAATTG GTACAATAAA  3060
GTAAAAAACT TTTTATTCAA AACAAAATGG ATTTACATTT AAACGTTTTA CATATTGATT  3120
CTGCGTATAA GTTCTTTTTC TAAACACTCT TCTAATTTCC ATACATGCTT GATAAAACAA  3180
```

FIG. 1(A-1)

```
ACTTTGTAAA TTCATAAATA TAGGTTTGAC TTGATCAGAA GGTGAATAAT AGCTCCATCT 3240
AAATGATTCG GTAATAGGAA CATTATTATA TATTAACCAG CTATATTTTG AGTTAACTCT 3300
TGCATGATCC ACTATATCTT TAAGTACAGG GATAAGTGCA CTCGGAAATC CAAAAGAATA 3360
GTTTTTAATA AATCTATTTA TCTGTGAAGA ATCAAGCTGC GGACTAATAA CATGACATTT 3420
TGATTGAATT TTTAAATCCT TAATATTTCC TCTATCATGA CGCGGGTTCA TATTATGTAA 3480
AACTACTACA ACAGTGTAAC CATTACATTT GGCAAATCTA TTAAAAATTT TTGACGGTAA 3540
AGCATGAAAG AAAGAACTTA TAGAATGACA TGATCCCAAT TGATTCATAC ATTCATCTAT 3600
TATAATACAG ATAGATCCTT CACTTGCAGC TCTGCAGAAT ATATTATCTG GATTATCAAT 3660
ATTTAGATTA GTATCGGAAA TAGCATCTTT GAAAGCTAAT TGTATAAATT TTGGATTTAA 3720
TGTTTTTGTT AGTGGATTAG AGAATGCATC GTAGTTTCCT TCAACACACT GTGCTTTCCA 3780
CGCAATTTTT TCTTCTAATG GAACAGTACC TTTTTCTGGA GTTATGAAAA AAATTGTTTC 3840
TGGTATTGGA TCAATTAGTT TTCCAGATAT AATATTTCTT ATAAATTGAG ATTTTCCGCT 3900
ACCTGTGGGT CCATATACAG TAACAATGAA TGGTTGTAAT CCGCAGTTTA AACTGGGTAT 3960
ACAGCCATCT TTTAACAGAT TGTGAGCCTC ATTTACAGTT TTTGATAAT TTACAGCAAT 4020
ATTGTGTAAA TCAGTCATAA GTTGACCATG ATACATACAT TTATCAAAAA CTTCTTGACT 4080
TTCTGGAAAT GGATTTCTGC AAATAGAAGG ATCTATCTTT ACAACATCAT TTTTCCAATT 4140
TAATGTGTCA CTTAAAAATT TTCCGAAAAA GGATTTTCTG TCAATGGTTC TTGCGGTCTT 4200
GGATTTGGGT GTCTCTTGTC GTACGGGTAA AGTAAGTATC CTTTCTTCCA CTGGATCCCT 4260
TTCCTCATCG TTTGATCCTT CCAAGGTCTC AGAATTCTGG TTAGTTGCTT CTCTAGCACC 4320
GTGAATGGTA CATCGGTTCC ACTTGCGGTT TGCAGTGTCT TTTTTAAACT TTTCCTCGAT 4380
GTCTGAAACT CTTTCTGTGG TTGTTCTAAT AAATTATAGT CAGTAAAACA ATGTTTTAGA 4440
ATTTCATAGT TTAAACAATT TTTAGCATGA CCTTTGGCTC TTAATTTTCC TTCTCCAATA 4500
AATTTACAGT TTTTACAAGT TATGTCTTTT AAAGCATATA ATTTAGGAGC TAAAATACAT 4560
GTTTCTGAAC TGAATGCTTC AGCTCCGCAA CGGTTACAAA CAGTTTCGCA TTCAACCAAC 4620
CAAGTTAGAC ATGGATGTTT TTCATCAAAG ATTAAATTTG AGTTATATTT TTTAAGTCTA 4680
TGTAATCCTT TTGATAACAT GAGTTGGTGG CCCTTTTCTG TTAAGAATAA CGAGTCTGTA 4740
TCACCATAAA TACTTTTTAT CTCCCTTTCT ATGTAAGGTT TACCCATATC TTCCCCATAT 4800
AAAATTTCTG CCCACTCACT CATGAAAGCT CTGGTCCAAG CCAGCACAAA GGATGCTATC 4860
TGAGTTGGAT ATCGGTTGTT CTTGATCCAT TCTTCCTTAT CCTCAATAGT TGTTAAAATT 4920
AAATCATTAC AATCAGCAGA TAAAAAAGTT ATAGGCTTAA AAGTCACGTG ATCTTGATTT 4980
CCTATAAAAA GTGGAAAATT AAAATTTTCA TTTGTGTCTT TGGAATCTTT GGGCGGCATT 5040
TCAGGTAGGT TTGAAAAATA CTGATTCCAC TCAAATGAAC GTTTTGGTAA TGATTTACTA 5100
ATCACAGTTG TGTATGATGT AATTTCAGCT GATCCATTTT CTAATCTTTT TTTATCTTTC 5160
TCTTCAATAT TTTCAGCAAA CACTACTTTC TTTTTATCTA TACGGGTAGC AAACGAACCA 5220
TATAAAGCAT TTGATAACAA TTTACTTATA CTTCGCTGAA TCTTGTTGTT ACTTTTACTT 5280
GCTTTTTCTT TAGCCATAAT ATTTACTTTC ACATATTTTT GACATAACGG TTTCCAGTCA 5340
CTCCATACAG CATACATTTC AGAGCTTTTG ATTATTTGC ATTTCCATCC TCTATTGTGT 5400
AAGGTGATTA AATCGATAGA GGTCAGTACT TCATTATCA ATGTTTCATT TGACCAGCAT 5460
AACTTTCCAC TTTTTTTAGA ACATAATGGA GGTAACACAT CAAGATAATC TAATGATGGG 5520
GGTTCACAAT CGGCTACCAC AATCATAGGT TTGATTGAAT TGTCAAAATA ATCTATTTTT 5580
TCTTTTCTTT GTAGTAGTTC TTGAAAGTAA TCTATTTGTG CATTGGCTTC AAAAGCATTT 5640
AAAGTTTTTC CATATGGAAG TGGATGCGTT AAGGCACTAG CATACATTCC GCAGATATCA 5700
TACACATATA TTGCTTCTTC AAATATTCCT AAAAATGAAG GATAACATCT TCCTCCTCTT 5760
AAACTCATTC TAACAAAATC ATACATTTTT TCTGATGGAG CTTCCAACTT TCTTAGGAAT 5820
TCAGAGGGAT GATCTTCTTC ATTATAAAAG ATTGTTTAA ACAATGCTTG AGTATTACTA 5880
CTAATTGTAG GACGTTGGAA TATATTAAAA GAACACTCAA GCTTAAAGA TGTTGTACAG 5940
AACTCTTGAT AACCTTCTAT AAGTTTTTCA ACTAAATTGAG CCGTAACTAT AACATCATCA 6000
ATACAATACT CCTTAGCTTC CTCTAATAAG TTGTATTTTT GGTTGTGTTT TGGTTTGTTT 6060
TGTAAATATT CTTCAAATGA ATTCCAAATAT TTTGAACTG GATAACCATT GTTTCTTTT 6120
TCATATTCTC CCAACATAAA AAATCATTG ATTGCCCTGT AAGGACAATA ACCTTTGCTA 6180
ACACTCAACT GATATGCAGT AGCAGCGTCT CTTAAAGAAG AGTGGGTTAA CAAAAATGTA 6240
TCCCTAACCA TAAATTTTAT ACCTTGCCAT TTCATATCTT CAAAATTAAT AATTCCATTT 6300
TTCCATCTTT CATAAGTTGT ATGTGAAGGT TTCTTAAAGC AAGGATTTGG AAGAGATAAT 6360
```

FIG. 1(A-2)

```
GTAATATCAT TAAATAACAG TTTTCCAGCA CGAGGCATAA AGCTTCTTGT CAGCTTAAAC 6420
ATTGAAAGTT CTTCACTGTC TATTCCTTCT AATACATGAC TTGCAAGTAT GATTTCATCA 6480
AAACCACAGA TATTATGACC TACTACATAT AATTCAATAT ATCTTGGTTC GCACTGTTTT 6540
AATTTTTTTT CTTTATTTAA GACCATGATG TCTTCATATG ATAAATTTGA TTCAAGACCA 6600
TGATTTTCAC AAAACGTTGA CCAGTATTTT TTAGCTACTG AAATTTGTAG CTCTGTTCTG 6660
AATTTTTTAA AAGCTATGCC AATTTCATCT TCTTTTTTAT TTAACATTAC AAAACATTCT 6720
CTGTTTACCT CATAACCTAT ATCGGTAGCT ATTTTAGAAG CAATTTTTAT GAGTGATTTA 6780
CATCCAATTA ACTTAAAAAC CAACAAGTAA GGAGTTAACT GTTTTCCATA CAAAGAATGG 6840
TAAGTATATG TTTCAATATC ATAAACAATA AAAGACGTT TTGCTTTTAT GGCTCCAACT 6900
GGATTAAATT TGATTTTTTC CCACCAGAGT TTTGTTTCAT GGTGAATATT GTGATAATAG 6960
AAGTCCCGTC TTCTGGATGA GCAGTTGTGT ATATTACTAT AAATTGTTCC GCAGAATTCA 7020
CATTTATTCT GTTGTTTAAC AGTTTTTATT AAATATATTT CTCCTTTTAA AATCAATAAT 7080
TCTATTGGTA ACAAATTTCC ATTAAGAATT TCTTCAGTCA TCTTAAAAAA TCTTTTGTTG 7140
AACTTCCATA TTTTTAAAGA TACGGGGGTG TTAGAATCAC AAAGTTTTAA AACATCTAAA 7200
ACATTTTCTA CTTTCTTGAA AGAATTTAAT TTTAAACCCT GAATTGCAAA GTAATTATAA 7260
AAACTTTTTT CAAAATTCTT GTAGTATATA ATTTTATAT ATGTATCCTC ATATATTCCA 7320
GTAATATAAG TAGTAGTTCT TTGCTTTATT ATTGTCTTTG AAGCCATCTG TTTAAAGCCG 7380
CTTCCCGTAC TCGCTCAAAG CTTCTTAAAA CAACTTCATT TGTACTATAG CCAACAATTC 7440
CAGACAATTT TATTCTAAAT GCTATTTCAA CTGAATCTAA ATCTGAAAAA TCCGTGTTTA 7500
CTTGGTTGAT TACTTCTTCT ATGCTCCCAC TGTCTTCTAC GAAGTCTATA TCTTGAAGTA 7560
ATTGGTCTCT TTCTTCTGGA GTTGAAAAAG AGTAAGATCT TTCATTAGCT TCTATAATTC 7620
CTAAAAAATC ACGAGTTATT CTGCTATATA GTTGTCTGAA TGCTTGTGTT TCTCTATTAA 7680
ACCAAACTCT AGTAAATATA TCTTCTCCAT TTTCATTTCT ACCTCTTAAT ATAATTTGAA 7740
CAAATTGGAT TCCAATATTT CTGGCAGCTA ACCTATTTTG CACTAAATTT AAGTATAAGT 7800
AATATAGCGT GCTTGCCACA TGCTCTAATA TAAAGAAATA CACTAACCAT TTTTGAATAA 7860
AATCATCAGT CAATCTATTT TCATTATAAA ATCTAATAAG TAATTGAAAA AATTCACTTC 7920
CGTAATTAAA AAAATTACTC CTTCTTGCTT CAGGAGTTAA TTCTTCTTCT AAATTTTGAA 7980
TTAAATCTAC TATTGAAGCT ATCACTTCAT CATTAAATTC TTCCCTACTC AGATCGCTTG 8040
AGCTCGGCTC GCGATCTGAA AATCCTTCAT CTTCTATTTC AGGAACAGTA AGAGGAGAAC 8100
TAGAAGTTTC TTCAACATTC CTTACCCTTT GGCGTCTATT AACAGGTAAT CTATCAATAA 8160
ATCTTCTGAT TACATCACCC CTTGAACGTC TCATTATTTC AGTAATAGCT CTATAATTTT 8220
CCCTAGGTCT TAATCTGAAT GGTAATCCTA CTCTTGTCCC TGACCTTAAA GTTAATGCTC 8280
CACCATGCAT CCCACCTTTT CCTAAAGTTA ATACAGTTGC TAAATCTTTT AAATTAATTC 8340
GATTTCAGC TTCTGGAATT TCCAGCTGTG AAAATTCATC TATAAAAGC TCAATCCAGA 8400
ATTCAGAAAA AGGTAAGTCT AATATACATT CACTATTATG CATGTTAGAC AAAATTAAAA 8460
ATTTACATAA AGCTTTTTTA ATTTTACAAA TTAACTTTAT AAGGTAAGTA TCCCTTTCTT 8520
GCAAATTTAA AACCATAAAA GCTTGAGAAA AAGGTTGATA ATGCTGCTGA AAAGATCTAT 8580
TCTGATTTTG AGCTGAAATA GCGGAGCCAA AACCTTGCAT GTCTGCAAGT TGCAGACTCC 8640
CTAATATTCT ATCCATTAAA ACCGCGTTTT GAATTTGACT AATTGTTTGT GAAAAATTTT 8700
CTACATTTTG AATTGCTCTC ATATATGACC CAGTATTTAT GGAGTATGAA CAATCAGTTA 8760
AAATTTGCCA GGTCATGCGT CTCTCAAAAC TTATAGGTGA AAGATACAAC TTATATGAAA 8820
TGTTGCTGTA AGTCCGCTGA TCAAACAGAT ACTGGTTTAA AACTCGCGCC ACATAAAAAT 8880
ACCCAATTAA TAAATTTGGT GGAGGTTCTC CTTCAAATGG TGGTTGTGAA GTAACAGGTC 8940
CTCTTGGCG TAAATCGAGT AATTGAGTCA CTGGATAATT AAAAAATCGA TTAGCCCATT 9000
TTATTCCCCT TTCATGTATA GTCCTTGACC TGGCAATACT TGATTATTA AGGTCAAGTG 9060
TTAAACGTAA ATATCGTAAG GTATGTTGAC TTTGCCCAGT GAGTTGTTGC CATTGGTGAA 9120
TCTCCAAGGC AAACAAAAAA TTTATCTTAT TACTGCAGAT GCATCCTATT TTACAAAATT 9180
TACGTTCATC ATTGGAAACT CCAGACTTAT CAAGCAACTC CCCGGGCACG TCAAATAAAA 9240
ATGAAAAGA TGAATTTGAA CCAGCAGTTG GCATTTCTAG CAAACCATCT GATGAATTTA 9300
ATATGAGACG ATCTCAAAGA GATGATAATT TACCTAAAAG TCAGATACCA GTAGTAGATA 9360
TACTACATGA TAAAAATCCT AAAATGGCAG AAGAAGGAGA CTTAATGTAT AAATCTTCTG 9420
CTTGCATAAA ACTTGATGAT TCTAAACAAT TAAAAACTGA TATGTTCAGG CCGGATTTTG 9480
CTGGAACTAG TCCAGCTCAA AGACACATAG AAGCGGCAGA GCTAAAGAGA AATGGATCTT 9540
```

FIG. 1(A-3)

```
ATACTCGTAG TTTAGAACAA TGGACACATG ATTCTTTTAT AAGTCATGTT AAACAATTAC  9600
TTTCTAGACC ATTTATATCT CTAGGTATTA CATATTTGGA TGATTTTTTG CAGACTTATT  9660
TAGATCATAC TGAATCGTCT TCTTTAAACT TTCAACTGTT TACTTTAATA AATCACTGTT  9720
CAGAAAATAC TTTAAAACGG ATTTTAAAAC ACATTTCTAA AAAAAATGAA AAAAATCAAT  9780
ATGTAAATCA ATGGTTGATT GATCTCATTA CATGTATATA TCTAATTATA AGAGATGAAC  9840
AAAATGTTAC AGAACAAGTT AATGCCCTTT TAGTAACTAG TAATCACTTA GCTTTACATT  9900
TTGCAAAGAA AGCTACAGGT GGATTCTATC CTACAGCAGA CAAGTTAGCG AAGACTCATA  9960
TTTTTTTCAA GAGAATAATT TTAGGAATAC TTTCGCTAGC AGAAAGTATA GGTTGCTATA 10020
CTGTGAATCC ATATTGCAAA AATCCTTTGA AAAAGTCAAA AGTAGAAGTA GAACCAAGTG 10080
ACGAAATGTA TATGTTCAGC TTAAAAGGTG CACTTGAACA TCCTGATTCC GACGAAGACG 10140
AAGACAGTGG ACTTCAAAAT GAATAATTAT CATAAATGGA CTTCTAATGT TATAGATGCA 10200
ATTCTATCAA ACAAAGCTCT TTTAGCTATA AAAATTTTAA AAGTCAACCG TTTGCAAACA 10260
AATTGAATGC TTTAGAATCA GCAGTTGTGC CTCCAAGAAA AGATGATACT CCTGAAATGA 10320
TAGCAAATCT TTTAAAAGAA TTAGTTGCTT TGGGAGCTAT TCGCAGTGAT GAAGTTGGCC 10380
CATTATATTC TGACCTTCTT ATCAGAGTTC ACAAATATAA TAGCTTGAAT GTTCAATCAA 10440
ATTTGCAAAC TTTAACAGGA GACATTAAAT CACTTCAATC CGATATAATT AGAAGTTCCG 10500
ATATTCCCAA TTTAAGTAAT CAAGTTGTTT TAAATACATT TTTAAATTCT TTGCCCTCAA 10560
CTGTTACATT TGGACAACAT AATTATGAAG CTTTTAAACA AACTCTAAGA TTATTTGTTA 10620
ATGAGACACC TAATATTACA GTTTTTAGAT CAGGAAATGA TACTTTAATT CAGGTTAACA 10680
TAACAGGAAT TCATACAATT AATTTGAATG ATGCATTTAA AAATTTAAAA AATTTTTGGG 10740
GAATAGTATT AACAGGTGAA TTTATTCCAG GTGATATTAC AAGCAGACTA ACAGCTAATA 10800
CAAGAGTACT GCTTTATTTT CTTGCTCCTT TTACAAATGA TAATACATTC ACACCTGATA 10860
CTTTTCTAGC TTTACTCATG AAATTATATA GATTGACAGT TTCTTCTGCT TTAGATTTTG 10920
AAGAAGAAAC TGAAGCTGAA GTAGAAAATG TAGCTCAACA AATAGGATCC ACTAGTGCAG 10980
ATTTTACAAA GACTTTAGGA TATCTATTAA AAAACAAAGA AGAATCATTT TCGCCTCCCA 11040
AATCATTATC TCCTAGACAA CTGGGTATTT TAAGGTTCAT ACAGAAAAGT CTGGTAGATA 11100
AAATTGATAG AAATAATGAA GATCCATGGG ATGCTTTAGA AACTTTATCT TATTCATTTT 11160
CTCCGTCATT TTATGAGGCC AATGGGCCTT TTATTAGACG GTTAATAACT TATATGGAAT 11220
TTGCCTTACG TAATTCTCCT ACTTACTTCA GAGAAATTTA CTCCAACAAA TATTGGATAC 11280
CACCCAATTC ATTTTGGACT CAAAATTATG CAGACTTTTT TTCGGAAAAG AAAGAAAAAC 11340
AAAATTTCGA AACATTTGAA CCGCGGGAAC TTCCTTTACA AATCTCTGAG GAAGAAGCTG 11400
TCCCGCATAC AGAAGATTTT CAGTCAGCCA TCTCGCCCTC TATGGGCCAA ACTTCACTCC 11460
CTGCTCCTTC TGTGTCAGAA TACAGTAGCG TGCCTCGGTC AGCTTTTTAC CCTCTCAGAG 11520
AACGTATCCA AGAGAGCATT TCAAAGGCAG TCATCCCTCC TTTGACAGGC TATGTCGGAA 11580
AACAAATAGG TGAAACTATT TTCCCTGGTA GTGGAGATCT TGTAGCACCC GCTGCGTCTT 11640
TAGTTGCAGC ACAATTGGTT GATTCAAGGT TTAATAACAG AAGACAAAGA TTGAAAGACG 11700
CAGCCAGAAA GCGTCACCGC TATGTTAGAG AGATGCATAA TATTTCTGAT AAAGAGTCAA 11760
ATGCTTCTAA TGATACGGTA ATATCACCTT TGATTGGACA TGGTTCGCGC ACTGAAAATC 11820
GTTTTGAATA TTTGAGACCT AAAGGTGGAA ATTATTTATA CTAATAAAAA TCATAACAGA 11880
CCTGACGGGC GGTCATCCTT TTTTATTAGA TGCAGAAATT TCTACCTCCA CCACGAATCC 11940
TTGCTCCAAC AGAGGGTAGA AACAGTATTA CTTATACGCC TCTGGCACCA CTGCAAGATA 12000
CAACAAAAGT ATTCTTTATT GACAATAAGT CTTCGGACAT TGAAAGTTTA AACTTTACTA 12060
ATAATCACAG TAACTTTTTT ACAAATATTA TTCAAAATGC TGATTTCGCA GCGGATGAAG 12120
CAGCCAACGCA AGATATTAAA CTGGATGAAA GATCTAGATG GGGCGGTGAA CTGAAAACTT 12180
TTATAAAAAC AAATTGCCCC AATGTTTCAG AATTTTTTAA CAGTAATAGC TTTCTAGCCA 12240
GATTAATGGT AGATAAAACT GATCCAGAAC ATCCTAAATA CGAATGGGTA CAAATTACAA 12300
TTCCTGAAGG CAATTACACT GGAAGCGAAC TTATAGATCA ACTTAACAAT GGTATTTAA 12360
ACAATTACTT AGAAGTGGGA CCCAAAAAG GAGTAGAAAT TGAAGACATA GGAGTAAAAT 12420
TTGATACAAG AGATTTTTCA CTTGGATATG ATCCTGAAAC GGGACTAATT ACTCCAGGAA 12480
AATATACATA TAAAGCTTTT CATCCAGATA TTATCTTGCT ACCTGAATGT GGCGTAGATT 12540
TTACATATTC TAGAATTAAT AATATGTTAG GTATAAGAAA GAGATTTCCA TATACTAAAG 12600
GATTTCAAAT TTTATACAGT GATTTGACGA AGGGAATAAT CTCTCCATTA CTGAATTTAA 12660
ATAACTATCC TCATTCTATC GAACCTGTAA TGCAAGACGA AAATGGAGTT AGCTATAATG 12720
```

FIG. 1(A-4)

```
TAGAAAAAAT AAGTGACAAT CCCCCCAGAT GGCAAACAAA GTACAGATCT TGGACTTTAA 12780
GTTATAAAAA TAATGGAGGA GCTAAAGCCC TAACTGTACT AACTGTTCCG GACATAACAG 12840
GAGGATTAGG TCAAATTTAT TGGTCAATGC CAGATACTTT TAAAGCACCT ATTACTTTTA 12900
CTAACAATAC TACAAAGCCA GAAACACTTC CAATTGTTGG ATTACATATG TTTCCTTTAA 12960
AAGCAGGGTT AGTTCATAAT ATAAATGCGG TTTATTCTCA ACTTTTGGAA CAAATTACAA 13020
ATACAACTCA AGTATTCAAT AGATTTCCTA AAAATGCTAT ACTAATGCAA CCACCTTACA 13080
GCACCGTAAC ATGGATAAGT GAAATGTCC CCTTTGTTGC AGATCACGGG ATTCAGCCAT 13140
TAAAAAACAG CCTTACAGGT GTACAAAGAG TTACTATAAC AGACGACAGA AGGAGATCTT 13200
GTCCATACAT ACAGAAATCT TTGGCGACTG TTGTCCCTAA AGTACTTTCA AGTGCTACAC 13260
TTCAGTAACA ATCTGGCTGA TATCTCTGGG CCTTATCCTC CTGGAACCGT TATGTCTATT 13320
TTAGTTAGTC CCTCTGATAA TACCGGGTGG GGTATTGGAA CATCAAGTAT GAGGGCTACT 13380
GGCTTGAAAT TTTCTAAAAA ACAACCTGTT AGAGTGCGAC CTTATTACAG AGCTCAGTGG 13440
GGACAGCTTA ATGCTCGTAC TTCACTTGAG AAACTAAAAA CCAAATTGAA ATATTATGAA 13500
AAATTGTACA GGACAGACT AAAAAGAAAA ACAGTTGTTC CAAAGAAAAA GAGGTCACCT 13560
ACATCTCCTG CGGATCGACT TAAAAAATAT CTTAAAGCTG TCAGTCAAAT CAAAGCTTTC 13620
AATAGAGCTA GAAGAGCAGC CCAATAAATA TTATTTTTCA CTTGCAGATG AAGGTAGTTC 13680
ACGTGCTTAA ATCTCCTCAT CGTCGAAGAC ATACACGTCG TTACAAAAAA CTAAAAAAAA 13740
TCAATCTATC TCCATACATT TTACCTAAAG AATTGCAAGG CGGTTTTTTA CCAGCTCTCA 13800
TTCCTATCAT AGCAGCCGCA ATTAGCGCAG CCCCTGCTAT AGCTGGAACT GTAATAGCTG 13860
CTAAAAATGC TAATCGTTCT TAAAATTTAG AAAACTTTTT TTTAACAGA TCACATGGCT 13920
TTTTCAAGAT TAGCTCCCCA TTGCGGCTTA ACACCTGTTT ATGGCCACAC CGTTGGAATC 13980
TGTGATATGA GAGGAGGTTT CAGCTGGTCT AGTTTGGGAA ATTCTTTTAC TTCTGGTTTA 14040
AGAAACATAG GTTCATTTAT ATCAAATACT GCTCAAAAAA TAGGTCAATC ACAAGGATTT 14100
CAGCAAGCCA AACAAGGTCT ACTGCAATCA AATGTTTTAG AAAATGCAGG ACAATTAGCA 14160
GGTCAAACTT TAAATACTTT GGTAGATATT GGAAGATTAA AGGTAGAGAA AGATCTAGAA 14220
AAATTGAAAC AAAAAGTTAT AGGGAACGAC CAACAAATTA CTCAAGAACA ATTAGCTCAA 14280
CTAATAGCCA GCTTAAAACC AAAAGATGAA ATGTTTGTAA AGCAATCAGA AAAAATTGTT 14340
GAACCTATGA GACCAGAAAT TAAATCTAGC CAAATGCCTG TAGAAATGTC TTTTTATGAT 14400
TCTGTAAGTG ATGAACCAAT CATAAAAACC AAAGAAGTTA GCCCTCCTTC ATTTTCATCT 14460
GAATCTTCAC ATTCATATTC TCACCCAAGA AAAAGAAAAC GCGTATCCGG TTGGGGTGCA 14520
TTTTTGGATA ACATGACTGG AGATGGAGTA AATTTTAATA CAAGAAGATA TTGTTATTAA 14580
AAACACTTTT TATTTACAGA TGGAGCCACA GCGTGAATTT TTTCACATTG CGGGTAGAAA 14640
TGCAAGGGAA TACTTGTCTG AAAATCTGGT ACAATTCATC TCTGCCACTC AAAGTTTTTT 14700
TAATCTTGGA GAAAAATTTA GAGATCCTTT TGTAGCTCCA TCGACGGGTG TAACTACTGA 14760
CCGTTCTCAG AAACTTCAAC TTCGTATAGT TCCGATTCAA ACTGAGGACA ATGAAAACTT 14820
TTACAAAACT AGATTTACTT TAAATGTAGG AGATAACAGA GTTGCAGATC TTGGAAGTGC 14880
ATATTTGAC ATTGAAGGAG TTATTGATAG AGGACCTACT TTTAAACCTT ATGGAGGGAC 14940
AGCTTATAAT CCATTAGCCC CAAAATCAGC TTTTCCCAAT GCAGCTTTTA TGGATACTGA 15000
TGAAGCTACA ACAATTTATA TTGCTCAACT CCCTAATGCT TATAATGCTC AAAACAAAGG 15060
TGTAGAAGAA GCAATTCGAG TAGAAGCAAA CACTACTACT CCTAATCCTC AATCAGGAGA 15120
ATATGCTACT TATGACTCTG CCAAATTTAA TCCAGAAACT ACTGGTGCTT CTGGAAGGCT 15180
TTTAGGAATT AATAGCTTAG GAGATCTTTT TCCGGCTTAT GGATCTTATT GTAGACCTCA 15240
ATCAGCAGAT GGTAACATTT CAACTGCACC CATAACTAAA GTCTATCTAA ACACTACTGC 15300
TACAGATGAC AGGGTCAGTG GAGTTACTGC AGTTGACACC GCAACCAGAT TGCATCCAGA 15360
TGCTCATTAT ATTGAATATA CTGATGAAGC CAAAGCTACA GCTATAGGAA ATCGCCCAAA 15420
TTATATTGGT TTCCGAGACA ATTTTATTGG ACTCATGTTC TACAATAATG GTTCTAATGC 15480
AGGAACATTT TCCAGCCAAA CACAACAACT TAATGTTCTT TTAGACTTGA ATGACAGAAA 15540
CAGTGAACTA AGCTATCAAT ATCTAATAGC AGATCTGACA GATAGGTATA GATATTTGC 15600
ACTTTGGAAC CAAGCAGTTG ATAGTTACGA CCAGTATGTC AGAATTTTGC ATAATGAAGG 15660
ATATGAAGAA GCCCCTCCGG CCTTATCATT TCCTTCTCAA GGTATCCAAA ATTATTTCAT 15720
GCCTACTGCG GCAGGTAATG CGATGACAGT AGACACGGGT AGAAATACTG CAGCAAAAAC 15780
AGATAACACC AAGGCTTTTA TAGGATATGG CAACATGCCA TCTTTGGAAA TGAATCTGAC 15840
AGCAAATCTA CAACGTACAT TTTTGTGGTC TAATGTAGCA ATGTATCTGC CAGATAGGCT 15900
```

FIG. 1(A-5)

```
GAAAACAACA CCACCCAACA TAAATCTACC TGATGACACC AACTCTTACG GATATATAAA 15960
TGGAAGGGTC CCTCTAGCAA ACATAATAGA TACATGGACT AACATTGGGG CTAGGTGGTC 16020
ATTAGATGTT ATGGATACTG TAAATCCATT TAATCACCAC AGAAATTCAG GACTAAAGTA 16080
TAGGTCACAA CTGTTAGGAA ATGGAAGATA TTGCAGATTT CACATTCAAG TACCTCAAAA 16140
ATTTTTTCCT ATAAAAAATC TTTTGTTGCT GCCAGGAACA TATAATTATG AATGGTACTT 16200
TAGAAAGGAT CCCAACATGG TTTTTCAGTC TACTTTAGGT AACGACCTTA GAGCAGATGG 16260
CGCAACTATT ACATACACCA ACATAAATTT ATATGTTTCA TTTTTCCCTA TGAATTATGA 16320
AACAGTAAGT GAACTTGAAT TGATGTTGCG TAATGCTACT AATGATCAAA ACTTTGCAGA 16380
TTATTTGGGT GCGGTAACTA ATCTTTATCA AATCCCAGCT AATACAAATA CTGTAGTAGT 16440
GAACGTACCA GATAGATCTT GGGGTGCTTT CAGAGGATGG AGTTTCAATA GAATTAAAGC 16500
TTCAGAAACA CCTATGATAG GAGCAACAAA AGATCCAAAT TTTACTTATT CAGGATCTAT 16560
ACCGCTACTA GATGGTACTT TCTATTTAAC ACACACTTTT CAACGAGTTT CTATTCAGTG 16620
GCATTCTAGC GTTCCATGGC CAGGAGATGA TAGGCTTTTG ATTCCAAATT GGTTTGAAAT 16680
TAAGAGAGAT CCTAATATGG ACGCAGAAGG TTATACTATG AGTCAAAGTA CTATCACAAA 16740
AGATTTTAT TTGGTACAAA TGGCTGCTAA TTATAATCAA GCTTATCAAG GTTATAAATT 16800
GCCAGTACAT TCTAAATATT ATGCATTTTT AGAAAATTTT CAACCTATGA GTCGCCAAGT 16860
ACCAATTTAT GGTAATGGCA CTTATGATTT ATATACTGCT TATATTACAA ACCAAAGAAC 16920
CATGCAAATT TGGAATAATA GTGGTTTAGA ATCTAAAACT TCAAATCCTC CTATGTTATC 16980
CAACACTGGT CATCTTTATG TAGCTAACTG GCCATACCCT TTCATTGGAC CAAATGCTAT 17040
TGAAAACCAA CAAACTGAAA GGAAATTTTT GTGTGATAAG TATATGTGGC AGATACCATT 17100
TTCTAGTAAT TTTTTGAATA TGGGTAATTT AACAGATTTA GGGCAAAGTG TTTTGTACAC 17160
TAATTCTAGT CATTCACTTA ATATGGTTTT TACTGTGGAT AGTATGCCTG AAACAACTTA 17220
TCTAATGCTT TTATTTGGTG TTTTCGACCA AGTTGTTATT AATCAACCAA CAAGAAGTGG 17280
AATAAGTGTA GCTTATTTGC GCCTTCCTTT TTCAGCTGGT AGTGCAGCAA CATGAGCGGC 17340
ACATCCGAAA GTGAGCTGAA AAATCTGATT TCATCATTAC ATTTAAATAA TGGATTTTTG 17400
GGCATTTTTG ATTGCAGATT TCCAGGTTTT CTGCAAAAAT CTAAAATTCA AACTGCTATT 17460
ATTAATACAG GTCCCAGAGA ACAAGGCGGA ATACACTGGA TAACATTAGC ATTAGAACCC 17520
ATTTCTTATA AGCTATTTAT ATTTGATCCA CTCGGATGGA AAGACACTCA ATTAATTAAA 17580
TTTTATAATT TTTCACTAAA TTCTCTTATT AAAAGGTCGG CCTTAAATAA CTCAGACAGA 17640
TGTATTACAG TAGAAAGAAA TACTCAAAGT GTTCAATGTA CCTGTGCGGG ATCGTGCGGC 17700
TTGTTTTGTA TATTTTTCTT ATACTGTTTT CACTTTTATA AACAAAATGT ATTTAAAAGT 17760
TGGCTTTTTC AAAAATTAAA CGGTTCAACC CCTTCTCTGA TCCCATGTGA ACCACATCTA 17820
TTACATGAAA ACCAGACATT TCTTTATGAT TTTTAAATG CAAAAAGTGT TTATTTTCGA 17880
AAAATTATA GAACATTTAT TGAAAATACT AAGACTGGAT TAATAAAAAC ACATTAATTG 17940
TATTCTTGCT TTTTGACGTT TTCATTAGTC TTCATCTTCA TCTTCTTCTT CACTGCTAGA 18000
TTCCAAGATG GTTTTTTTTT TCTTTGATGG AGTAGGCTCT TCAATAGTTC CAAAAGGATT 18060
CATATCAGAA TCCTCTTCTA TGTTAGGCAA CATAGTATTT TTAACCTGGA ATGACTGATT 18120
CCACTTAAAT TGAGAAAACT GAATTGGAAT GTTATTTCCC ATACATTCAT TCCAAAATTT 18180
ACGCACAAGA GTTAAACACT GTAACATATC TGGCAAGCTA ATTTTCATCT CACAAAATTT 18240
TCCATTATTA CGTCTCAAGT TGTATTGATA GTTACAACAT TGAAACACAA AAACAGCAGG 18300
GAATCTAACT GCTGCGGCCT GAACTCTATT AACATCCTGA ACATCAATTC CTTCCACTCC 18360
AGATATAGAA AATGGAGTTA TTTTAGGGAG TTGTTTTCCT ATTGTTTGTT TGCCACCATA 18420
ATTACATTCA CACTGACCCA ATATAAAAG CATATTTCCG ACTTTAGCTT TCGGAAACAC 18480
AGCTTTTGTA GTTTCAATGG CATTTTGCAT AGCCAGCAAG GCCTTCTTTT CATCTGAAAA 18540
GTTAAGACCA CAACTGCGAG GAGAACATTG CCCAAAACGC TGATGGGCAT CCTCAGCACA 18600
TAACACGTAA TGTTCCTGAA CTATTTTTAC TACTTGTTTA TTCATACGCC CATTACTAAG 18660
AACACCCCTC CCTTCCTTTA GGGCTTGCAC CCCTGCTTCC GATGTTGGAG GCATTTCAAT 18720
TTCATTCACC CTTTTAAACA TGAAGTCACC ATGAAACAT CTAGGACGGT CCTCCTCCCA 18780
ATCATGATAC CACAAATAAC AACCAGAAGC ATTAAAGTTT GGAATCAAGT CAATTTGCTT 18840
ACAAATTGCA CTATATAGCA TTCTACCTCC TACAGTAGCC ATAGATTTAC TGCTACTATA 18900
AGTCAAATTT ATAATTTTCA TCTTTTTCAT GTACTGAGCA AATAATTTTT CACAATCTCC 18960
TTCTTCAGGA TGAACTTCA TTTGACTGGT ATCAACTTTA ACACACTCTC CAAATTTAGC 19020
TAAAATTTCG AGCGCCGCTT GAACTTTATT CTGAAATTCT TCTGTAGTAG ATTTCTCTT 19080
```

FIG. 1(A-6)

```
CTTGATAGAT TTAGTAACTT TTTTAGAAGA CATTATGTTA GTTTTTTTCT CGTTGTAGGA 19140
TGGCTGAAAA AAATATGGGA GAGTCAGAGA AGGGTTTGAA CGAAGAAGAA TTTAACTCTA 19200
TTCTATCAAA ACATCTGGAA AGACAAATTA AAATCTGTAA AGCGTTAACA TCAAAATTAT 19260
CGAACTGGAA TATTGGAACA TTGTTAGAAA ACTTGTTATT TTGTCCTGAT GAAAGACAAT 19320
CATCAGGTGA TCCCGACCCA AAACTAAACT TTTATCCGCC TTTTTTAATT CCGGAATGTC 19380
TTGCATTGCA CTATCCATTT TTTCTAACAA CTCCTATTCC GCTATCATGC AAAGCGAACA 19440
AAATAGGAAC TAACACTTAC CGAAAATGGA TGAACAATCA AGTCCTGGAT TTACAAATAC 19500
CTTCCTTGGA AAATTGCAAA TGGGATGATA GCTTGGGAAA TGTAGATTTA ATTGAAGAGC 19560
TTAAAGAGAA CCAAAAACTT GTTTTAGTAA AACAAGACCA TGAAAGAAAT ATATGGTTTA 19620
AATCAAAATG CAAACAACTT CAAAGTTTCA GCTATCCCTC ACTCAGTCTG CCCCCAGTTT 19680
TACAACAAGT TTTAATTGAA TCTCTTATCG GCATTAGTCA GGATCCTAAT AACTTTGACA 19740
AAAATTACGA ACCTGCAATA ACTCTAGAAA AACTACAACA TGTAAACTGT GATCAAGATT 19800
TAAAACAAGT TCAACAAAAA GTATCTTCAG CCGCTACATA CGGAATACTT TTGAAATGCA 19860
TTCAGACTTT ATTCAGTGAC AAATTATTCA TTCAAAACTG CCAGGAATCA TTACATTACA 19920
CCTTTAACCA TGGTTATGTA AAATTACTTC AATTTTTGAC AAATGTCAGT TTAAGCGAAT 19980
TTGTAACTTT CCATGGTTTA ACACACAGGA ACAGACTCAA TAATCCGCAG CAACATACAC 20040
AATTGGCAAC CGAAGACAAA ATAGACTATA TCATAGATAC AGTGTATTTA TTTTTGGTAT 20100
TTACGTGGCA GACAGCAATG GATATTTGGA ATCAAACATT AGATGATAAA ACAATAAATA 20160
TAATTAAAGA GGAATTAAAC CAAAATTTTG AGAAAATTGT CAAAGCTGAA TCAGTTGATG 20220
AAGTTTCTGA AATTTTAAAG TCTATTATTT TCCCTGAACT CATGCTGCGA GCTTTTTGTT 20280
CTAATTTACC TGATTTTATA AATCAGAGTC AGATATCAAA TTTTAGAAAC TTTATCTGCA 20340
TTAAATCCGG CATACCGCAG TCAATTTGCC CCCTATTACC TTCAGATCTA ATTCCTTTAA 20400
CTTTCCTAGA AAGTCATCCA ATACTCTGGA GTCATGTAAT GTTACTAAAT CTTGCTTCAT 20460
TTCTAGTAAA CCAAGGCAAT TATTTGCATG AACCCGAAAA ACCTTTAAAT ATTTCATCAG 20520
TTTACTGTAA TTGTAATTTA TGCTCTCCGC AAAGAATGCC ATGTTACAAT AGCAGTTTGA 20580
TGCAAGAAAT ACTAACCATT GATAAATTCG AGTTCACAAA CTCTGATAAA ACAAAACAGC 20640
TAAAACTGAC CCTCCAAACT TTTGCTAATG CCTATCTTAA CAAATTTAAC TCAGCAGAAT 20700
TCTACCATGA CCAAGTTTTA TTCTACAAAA ACTGTAAAAG TAAATTTTCT AACCAATTAA 20760
CAGCTTGTGT AATAAAAGAC GAAAAATTAT TGGCTAAAAT AGCAGAAATT CAAATAACGC 20820
GGGAAAAAGA ACTCTTAAAA AGAGGAAAAG GAATTTATTT GGATCCAGAA ACAGGAGAAA 20880
TCTTAAACAA TGGAGAAGCC ATATCATCCT CTGAAACTT CCAAAGGCAA AGAACTAGCT 20940
ATGCTCTACC ATCAAATGAA GGAGAGCGAG CTGGATGGGA AGCCGATGAG CGAAGAAGAC 21000
GAAGGAGAAG TGAGTGAGGA TGAAACAGAG ACAACAATTC AAAGAAAAT GAAGTTTACA 21060
AGTAAGTAAG CTCTAAATTT TTTATATTAA AAACTGAATT TTTTTAGACA AAATTATTTT 21120
AAATTAAATC TTTATAGCTA GCAGTTGATC TTTGTTCGTT TTTCAGAAAA CTCAAGTGTT 21180
CAGTCATATC AAGTTCACTT GCCTCTGAAA CACGAAATTG CGGAAATTCT AGAAAAAATT 21240
AGACTAGAAT CTAAAAAATA TCCAGGAAAA GTTATCAAA TAAGAAATAG AACTCCAGCA 21300
AGTATTACAA AACGATACCT GTATGAAAGA GATCTGAAGA AACTGTTCCA GTATCTAGAA 21360
GACGCAAAGA AGCTTTACGC TAAGTACCAA AGCTGAGGCT TTATAGTTTT AAATTTTCCC 21420
GCCATGGCTC AACCAGTGAC GCCTTACGTC TGGAAATACC AACCAGAAAC AGGATATACT 21480
GCTGGAGCCC ATCAAAATTA TAACACTGTT ATCAATGGT TGCATGCCAA TCCACAAATG 21540
TTTGCCAGAA TTCAACATAT AAACACCGCA CGGTTAACATC TGGACAAATT CCGCTCTGAT 21600
TTGACCCGAG ATGACATCGC GGTTAACATC AACAACTGGC CTGCAGAGGA TTTAATGCAA 21660
CCTCCTAATT TTCCTTACAT TCCTGCGACC TCTAAATCCG CTTCAACCAT AAATGACTGG 21720
TTGGCTACCA CTCAAGGAAT TCAACTCACT GGAACTAGTG AACTAAACGG GTGGGATCT 21780
AACCGCCTGA CTTCCTATCC GGATATTCCA CCCATTTTAA AGTATGAAAG GCCTGGTCAA 21840
CAACTTCAAG GCCAAGGACT TTTAAGCAA GAAAATATTT ATTTATTTTA CGAATCTCCG 21900
CGCCTCCCTC GCTCTGGAGG ATTAACTCCC CAACAATTTG TAAAAGAATT TCCGCCTGTT 21960
GTTTATAATA ACCCCTTCTC AGAATCTATG AGTGTATTTC CGAAAGAATT TAGTCCTTTG 22020
TTTAACCCTT CAGAATCTTT GAAAAAAACA TCCAGTCAAA CTTACAATA TAAATAAAAA 22080
ACTTCTATTG ATCTTTATAC TTACACTAAA GCATCGCGTT TATTTTCGTC GCCATAAAAA 22140
TATATCAAAG ACCCGTAATT CTCTAACTTT AAATCATTTC TTGAACTAAT CTTAATCCAT 22200
TTAAATGTAG GAATTAAATAT ATCAGAAACC AGTAACAAGC CAGAATTAAA ATATACTTGT 22260
```

FIG. 1(A-7)

```
GTCATTTTTA CAGATGAAGC GAGCACGCTG GGACCCGGTT TATCCCTTTT CTGAAGAGAG 22320
ACTGGTTCCT CTGCCTCCTT TTATTGAAGC CGGAAAAGGG CTAAAAAGCG AAGGGTTGAT 22380
CTTATCTTTA AACTTTACTG ATCCTATCAC TATAAATCAA ACCGGTTTCT TAACTGTAAA 22440
ATTGGGAGAT GGAATATTCA TAAACGGAGA GGGTGGCCTA TCAAGCACTG CTCCAAAAGT 22500
CAAAGTTCCC CTGACTGTCT CAGATGAAAC ATTGCAACTG CTATTAAGTA ATTCTCTAAC 22560
AACTGAGTCA GACTCTTTAG CTTTAAAACA ACCGCAACTT CCCCTAAAAA TAAATGATGA 22620
GGGGAGTTTA GTATTGAACT TAAATACTCC TTTAAATCTA CAAAATGAGA GATTGAGTTT 22680
AAATGTTTCA AATCCACTAA AGATAGCGGC AGATTCTTTA ACTATAAACT TAAAGGAACC 22740
CCTAGGATTG CAAAATGAAA GTTGGGCTT AAATCTAAGT GATCCTATGA ATATAACTCC 22800
AGAAGGAAAT TTAGGTATTA AATTGAAAAA TCCTATGAAA GTTGAAGAAA GTTCTTTAGC 22860
CTTAAACTAT AAGAATCCTC TCGCCATTAG TAATGATGCG TTAAGTATAA ACATTGCGAA 22920
TCCATTAACT GTTAATACAA GCGGATCTCT AGGAATATCT TATTCTACTC CCTTACGAAT 22980
TTCAAATAAT GCTTTATCAT TATTTATAGG AAAACCTTTA GGATTAGGAA CTGACGGCTC 23040
TTTAACTGTA AATTTAACTA GGCCTCTGGT ATGTCGTCAG AACACTTTGG CCATAAACTA 23100
CTCAGCCCCA CTAGTGTCAT TGCAAGACAA TCTTACTTTA AGTTATGCTC AACCATTAAC 23160
TGTAAGCGAT AATTCTTTAA GATTGTCTCT AAATTCTCCA CTAAACACAA ATAGTGATGG 23220
AAAACTTAGT GTAAACTATT CTAATCCTTT AGTTGTGACT GACTCTAATC TTACCCTCAG 23280
TGTTAAAAAA CCTGTAATGA TTAACAACAA AGGTAATGTT GACTTAAGCT TTACAGCTCC 23340
CATAAAATTA AATGATGCAG AACAGTTGAC TTTAGAAACC ACTGAGCCCT GGAAGTGGC 23400
CGATAACGCT CTAAAACTGA AACTTGGAAA AGGCTTAACT GTTAGTAATA ATGCTTTAAC 23460
CTTAAACCTT GGAAACGGTT TGACTTTCCA ACAAGGTCTT TTACAAATTA AAACTAATAG 23520
CTCTCTAGGG TTTAATGCTT CTGGGGAATT ATCAACAGCT ACAAAGCAGG GAACCATAAC 23580
CGTTAACTTT CTAAGCACAA CTCCTATAGC TTTTGGGTGG CAAATAATAC CTACTACTGT 23640
AGCTTTCATT TATATTTTAT CAGGAACACA ATTTACTCCT CAATCCCCAG TAACTTCTTT 23700
AGGTTTTCAA CCCCCACAAG ACTTTTTGGA TTTCTTCGTT TTAAGTCCGT TTGTTACATC 23760
TGTAACTCAA ATTGTGGGAA ATGATGTTAA GGTTATTGGC CTAACTATTT CTAAAAACCA 23820
ATCTACCATA ACTATGAAAT TTACTTCTCC CTTAGCTGAA AATGTACCAG TTAGTATGTT 23880
TACAGCACAT CAATTCAGAC AATGAATATT TTAAAAATTC TTTATTAAAG AGTAATCTTT 23940
TTACATACCG TTCTTGACAT AATGTGCCTC TATAATTAAC AAATCTAAGC AAGCAAGGTT 24000
GATCATTGGA ATCTATAGAA GCATAACTCT TCCAATAAGC ATAATCATAT GGCGGTAAAT 24060
GAAAACCCCT TAAATCTACC ATATTCATCT TTAAGTGTAC AGTATCTAAC AGGTTTTTAC 24120
AATCTTGCAC TTCTGCAATT TTAAAAACAA ACAGTACTTT CATAGGACAA CAATTGTAAC 24180
GGTTATAATC TGTTACTAAAA TTACTTATTT CTTCTTCCAA TGGCAAAGCA TTCCAAAGTC 24240
TTGTTATAAG TACTGTAAAA TCATCAAATG AATAACATAA CACATTTGTA CAACAATTGG 24300
TCCAAGGTAA AAAAACAGGC ACACGAACAT GAACTTTTTT TAAAATTAAC ATCAGTGTCT 24360
GTTTTAAACT TTGACATTGC AAAGAATTTG GCTGCAAGCA ATGACAATGA AATTGATTTT 24420
GCTGACAAGG TAAGTCACAC AAATACAACT TTAACAGCCT AAATATAACA ACATTAATGT 24480
AACTTTCCAA GACTTTAAAA CTAACAAACG GTATATCACA ATAAAAAAGA TGATGAATCC 24540
CTTCGCAACA CATAATGGAG TTCATGCTAC ATCCAAAGAT GGTTCCGACA AACCTCTGTA 24600
AATTAAAGAA CAACAATACA ACATACGAAG AAAATTAAAA CGTTTTTCAA AACGAGATAT 24660
ACATTGCTGC AAAGTATCTG AACATTTACA TTTTATACTT ATAAGCTCAC AAGTTTCAGA 24720
AAATGTAATT CGTTAACAG TTTGATATGA ATACCATTTT GAAGAAAAAT AGAAAGAGTT 24780
TTGTGCATTT GTAAGCTCCC AGAAACATTA ACGGACAGGC AAATCCAAGT ATTACAACAA 24840
ACAGGAACAG TCTTAACGTT TCGTTCAGAA AACAAAGTAA CAGGCATATG ATTAAAGCAA 24900
GACAATAAAA CACTTTTGGC AGCTAAACAT TGCAAAGATC CAGGTGAATT ACAATGACAA 24960
TGATAATAAA ACTTATAAGC CATATCGGCC CTCTTGCAAA ACGAATCAGC TTTTTGGCTT 25020
ATAGGAAAAT AACAAAAAAA CTGATTATAT ATGAATGGAG TTAATATCTT CTTCAAATTA 25080
TACACACGAA TAGCAGAACC AAGACGACCA CGCCCAACAC AGGTAAATAT TTCAAGTCCA 25140
TGACTAGGAA CAGATGGTTT CTCACAAGCA ACAACTTTGA TTTGCTTATC CATCACTGCC 25200
AATCAGGCTT AATAGGAAAA GAAGAAAAAT AATTTTCCCA ATAATAACGA AAGAAATTCC 25260
ACGTTTCATC CTGTACATTA CTAGTCACAA ATACAACCTC CGCTATCAAA GATTCCCTAT 25320
CATTTAAAAC TCCCACCAAA TTGTCCCAGT CTACCTCAAA AAAGCCAGTT CCCATATTTT 25380
CAAAATTTGC CCATTTTAAA TAATCCAAAG CATCAAATTC AGGAAACAAA TCTTTCTGAG 25440
```

FIG. 1(A-8)

```
CTAAAACATA TACAGTTTTA TCGCCATTAA ATCTAAAAGC CATCCTAAAT GGACCTCTAG 25500
CCCAGTAGTT TAAGTACCGG GAAGAGACTA TACAATATAC TTGATATTGA TGTCTGTTAA 25560
GTGGTGATAA AAAAGAAAGT AATTCAGAAT TAGGATAAAG CATTCTCCCA TGTTGATTCA 25620
TCTACAAAAA ACAAAAAAAT TATAAGGTTC ATAGAAAACC TACTATTTAA CAAATCTATA 25680
AAAATGCATT AAAAAGTTAC CTTGAATATA AATTCAGATC ACCTAAAAAA CGAAAAAAAA 25740
TAACATTTAT GTTAGTAAAT GATAGTCTTT AAAAATTAGA AAAGAATCAA GTCGCTTTTA 25800
TACTTACAAA CTCCAAATAA ATTCTGTAAC CAAGAGAAAA ATTGTAACCT AAAAGGTAAA 25860
GAAGAACATT ATAAGATTAA AACCACTCTA AAATCTGAAA AGCATTATGA AAAATTCTGA 25920
TAGCTGCAAC TTACTAGTCT TCTCCAAATG TTGCAGGCAT TTCAAAAAAT CAAGAGGAAA 25980
ACCGGAGTTT ATAAAGTAGT AGTCTGATTA TATCTGAAAA AGTTTAACTT CCTTTTCAAC 26040
CCAACCCAGT CCAATAAAAT TCCAACCTTA ACTTCTTTCC TGCTAAAACT CCATAAAAGT 26100
CCAATTACCA CTTGACTTTT ATTTAACCTC AATTATGTTA CATGTTATTC TACCCATAAA 26160
AACTTGATGA CCAAGAACTG ACCTTTCCCA TGTTTTCTG AAATAACAAA AATGTTGATT 26220
TAAAGATTTT TAACTACCCA AAAAACCCGC TCTCATGATT TTTTCTTATA TAAACAGGAT 26280
ACAAAAGAAC TGGCAAAGAT ATTCCATCAT ACTTCTCCAA CTGTCAAAAC ATACCACTTA 26340
ACCTCTCCCA TGTTTTTTCC CTTTTGCACA AACAGGATAT AAAAAATATT TTTGCCACAA 26400
TGTTTTTCCT TTTACTCAAC TGCCAGAATA AAAATGAACA GCTTAACCTT TTTCCCTCTT 26460
AACCCATTGC GTTCCTCTAA GAAAAAAATT ATCCCGCCCA ATATGCTAAA GGCTTCTCCC 26520
GCCAAAACAG CTCAACTTAA AATCTCTCAT GAATAAAACC CAGAGAAAAT TTCCAGTAAT 26580
AAAAATTAAT AACCGTGAAG TACTAGATCT AATAATGATA TTTTGAACTC ATAAAAATCC 26640
ACCATCCATG TAATGTTACA AACACTTTTT TATTGAGTTT TTCTTACAA CTGCATTACA 26700
TACAGGCCAA GCATCAAACT TTCTTCTGTA TTTCTTCCTA GACCACAAAA TTACAGACTT 26760
ATATTTCTGC CACAAATCTC TATGATCTTT ACAGTAACAC TTACATTTAA ATGGGGAATA 26820
CAGCAGCAAA TAAGGATGAG TTAAACATGC GATACAATGA CCAGAAGGAA GATAATACAA 26880
TACATCACAC CAAAATGAAG GTACAGACAA CATCGCATGA AATCTTAAAT GTGATTTTAC 26940
AATAAATTTC TGCAGCAGCT TACAATCTAT ATTAGCAAAC CGTTTTATAT ACAAACATAA 27000
AAACTTGGAA CTTTTCACCA ACTCAATCAT GTTATTATAA CACATTACAA ATTTTGCTAT 27060
ATCTTTATTT GTCAAATAAC AAAATATCTC AATCCACAGC TCATCTGGCA GCAAACTTCG 27120
CAAATCCATG ACCTGTAAAA GATACAACAG AAAACAGAAA ATTAATGCCA TTCAATAACA 27180
TAAAAAATAC AGTCAAATCA CATACTTTTT CTCACTTACA AAACTTTGTG AGCAGGCCTC 27240
CAAAACAAAC TTCAGAAAAT GGATGCATAC AAGAACATTC TCCTCTCAAA AATTGCTTTA 27300
ACTGAATGCG GCATTTTGCA CCTCCAGAAA AATGCAGTCC ATGAGAGGC TCTTCTCTTA 27360
AAACACAGAA ATGCTTCTGC AAAATCTGTA AAGAAACTAA CAACTTCCAA ATTCCAATCA 27420
TCATGCATTG CAAAGAAGGA CATTCAACAG CAAAAGGATC GTGATGAATG CATTTAAGCT 27480
TACTGTATGA CTCATTTTCA TGAATTACAG TCTGTAACTT ACTATAGAAAAC ATTTAAGCT 27540
CTGCTTCACA AATTAATAAT GCTAATTTCT TTAAGCAGCT CAAAGAAAAC TCATCAGGAC 27600
AACGGCATTT AAGAAAGCAA CAAAATGATT TCTTAAAATA CATTTTTCCA GCATGATGAA 27660
CAATAAAAAA TTTCAACGTT AAACAATGCA AAAATGCATT TTATGGTTGTA TGCTCCAAAA 27720
TTTTTTCAGC TGAAGCTAAA TCACAGCCTA TTTATTACA TGATTTTGTA TGCTCCAAAA 27780
GAGCTTGTTT TAATTGCTTC AAATCCATCT TCTTAAATTG CTACAGAAAC TGCAGACCAC 27840
GAACCGCATT CAGGCCAATT CCAGTTATTG TTTAAATTTG CTACAGAAAC TGCAGACCAC 27900
AAAACCACAT CCTCTAAATC AACCCACAAA GATCTATGAT CCACACAAAA ACACAAAGAA 27960
TGATACGGAG AATACAACAA TAAATGGGGA TTAACAAGGG ACGCAACACA ATGACCCGAA 28020
GGTAATAAAG TTTTACAGCA CCAATTACAA GCAACAGGTA ATGGAGTATA TTTCCCAATG 28080
CGACGAGAAA GCCGAATGTC ATTCAGAACA GCATTGCATT TTATCTTCTC AAACCTCTTA 28140
AGGTGCAATT GTATAAAATA AGAATCCTTA ATGACAGTGA TGAATTGAGG AAAAGCAAAA 28200
ACAAAACTAG CAATGTCTTT GCTTGTAAGT TTCAAAAATA TCTTCATCCA AATCTCAGTC 28260
GGTAATTCAA CAAAAAATTC AGGGCCTAC CCAAAAATAA AAAACTCTTA CCCCTGTTAT 28320
TGTAAACAGC GAAAAGAAAA AATAACACAT CTCAGTGTCA TGTTTCTTAA ATTGTTCCCA 28380
CCATCGAGAT ACACAGAAAA ATTCAGAACA GCATTGCATT TTATCTTCTC AAACCTCTTA 28440
AAGCTCAGAC ATTCTAAGCC AAAATTTTT TGAGAACTGC AAAAACCCAG TTTTTATAAC 28500
AAAGCCTTAA TGTTTCTTA ACTGATTTAA CTGCCCTAAC AGGAACTCCA CATTCCGGCC 28560
ACCGCCACCC AGGGGACAAA TCTTGCCAAG AACTACAAGT CCATAAAACA ACATCCTGCA 28620
```

FIG. 1(A-9)

```
AATTATACCA AAGGTTTCTA TGGTCGACAC AATTACAACC TGACCTAAAA GGTGAATAAA 28680
GCAGTAAATA AGGATGAGTT AAACAGGCCA CACAATGTCC AGAATGTAAA AAATGCTTTG 28740
TTTGGCACCA ACCAGACCAC AGCTGAAGCA AAGGAAAATT GTAGCGAACA CATTCTTCTC 28800
GTAATCTGTT TAACACAGAA CAACATTCAA TTCTGGCAAA CCTCTTTAAA AAATGTTTTC 28860
TGAAATATTT CTTTAAAATG ACAGTTTGCA ACTCTGGAAA ACACAAAATA AAAGCCGCAA 28920
TATCTCTACT GCTTAAATAT AAAAATATCA TTGTCCAAAT TTCTACTGGT AAAACTGAAA 28980
GCATCTTCTT CCTATTAAAA AAAGAAAAGT GTTTCAAAT TATATTAGAC TCTAACCAAA 29040
AAAATTCAAA TACTTTTCCT TTATAATGTA CATTAAGAAT AAAAATATAC TCACCGTTTA 29100
AAAGTAGAAC TTAACAGTAT AATATAAATA CAAGTGAGCT GAACAACGAC AGCCGATTTC 29160
AGCCGGAGCA AAATTAAAAA GAATAAAAGG ATCAAACCAA CACGTAGGAC AGTCTACTCC 29220
AAAACAGTAA CGGCAGTATG ACACAGAAGG AGAGGAACTA AGTCCAGGAA ACTTCGCCCG 29280
GTGCGATAAA AAGTAACGCC GCCGGAAAGC AGTTGAATAC AAAAGAGGTA AAAATTCACG 29340
AAAAACAGAA GCAAAAACTA CTAAATCTGC TATTGGCAAA TAAAGAAAAA TTTCAAACCA 29400
TATTTCCAAA GGAAGAAAAG CAATCATACC GTAGAAGAAC CTGAAGGCGA CCGCAAACGT 29460
GCTCCCGTAC CACAACGTCA CACGCCACAC CCACTGGGAA AACCCACACG CCCCGCCTCT 29520
GTGCAACGTT ATATATATGA ATAG                                      29544
```

FIG. 1(A-10)

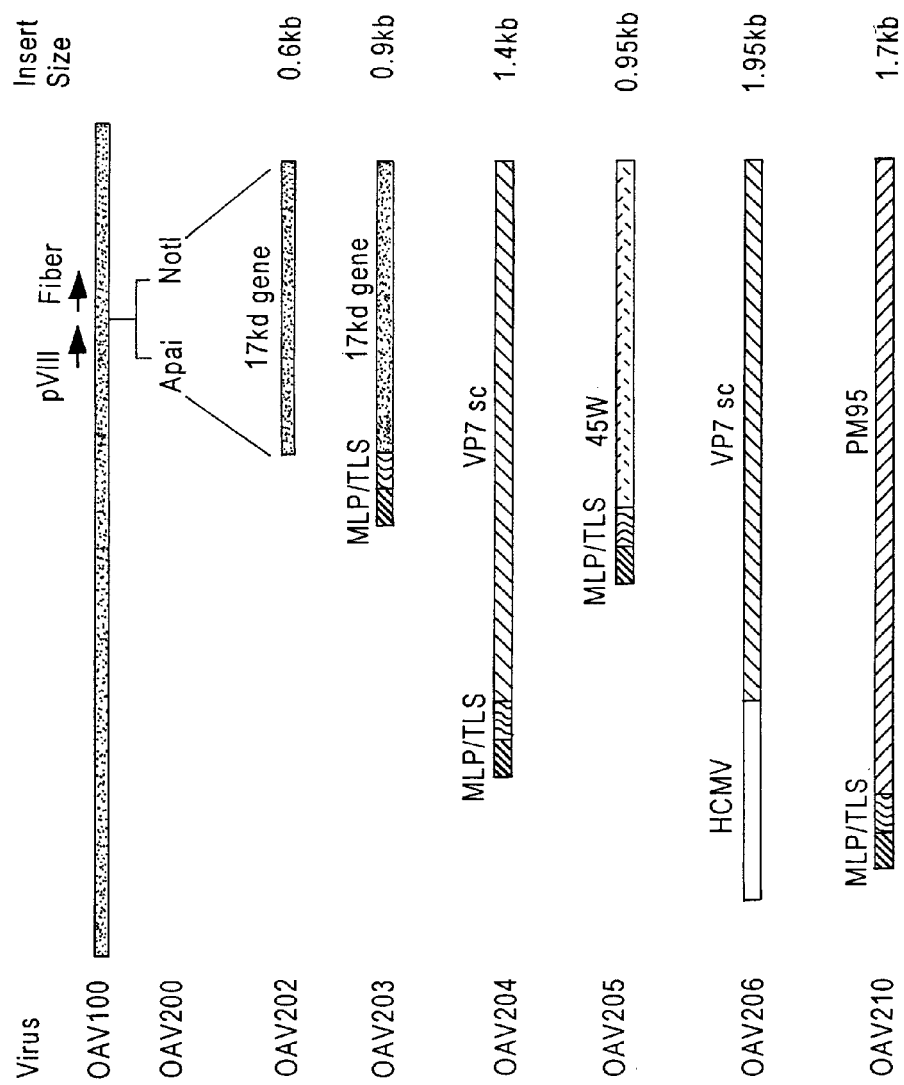

KpnI site (with 3' terminal sequence)

```
CTATTCATATATATAACGTTGCACAGAGGCGGGGCGTGTGGCTTTTTTATTGTTTATTGT
CATGGAATTTACAAAGAAGTAAGTTGTTGGATCTTTATTCACAATTCTTTTAACAATGAC
TTTTTTACTTATTACATTTTTCATCTTTTTTACTTCACATGATATTTTACTTAAATTTTG
TACATACAAGCCAAAATTCGCATAAAATGTCTTACTTTAAAAAGTTAAATTTTTTTTTA
ACGCATAAATGGACGTACAGCAGCAATTGGAATAGCAGGAAGGGCCATTGTAAAGTGTGT
TCCTGCTGATGCCGCTGCAGAAAGGATAGATGCTATCGTACGCATAAACCCCCCTCCTAT
TTGTTCATCTGCTGCTTTTATTATATCTTCTGCCAATCTAGGTGATATTTGCTTTTGAAT
GCTGTTTCCAAAAGCTTGCATCATCGGATTTTCAATTAAATGGATTGGATTTGCAGAATT
TCCTAAAAAATAGCCCAACCCATCTAAAGCAGTTAAAAGTATTCTCCCTCCAGGAACCAC
AGATATAATTAAGCGGAGCAACCGAGAGGTTAAATTCCAGGGTCCTCCGAAGAGAGTATC
TAGGATCAGGCCAAGAAGTGAACCAAAAAGACTTGTAAGTAGAAGTTGTCTGATATGCTT
TGGAGAGGACTGTAAAAATTGCAAAACGGTATCTAATGACCATTTCTTCTTTACTTTTAC
ATCTGTATCATGTTCTCCATCAGAAGGTCTTATTGGGAAGTACCATTGGTCACGAGCATC
TTTGAAGACTTCTGTTTCTTGAAATTCTGTTTTCGGTAAGCGACTAGCAGTTATGGTATT
AGGAATATTGACGGTAATGTTATTCACATCTACAATTTCTGGAGGAATCCATCTTGCATA
GGATGAAATGGGTTTTGTGGTTCTTTCAATATATAATTGCGAGGAGGGTTTTTCCAAAA
TCTCTGAACATAAGTATTTTCTGATTTTGGCGGTTTTTTGCTTTTTCGCGCTCTTTTTCT
TGGCTTTGGTCTTTGAAATTTTTTCTTCCTTTTTCTGTAGGCTCCTCCTGCTAAAGCTGT
GTTATTTGTGACGTACATCCTGTTAGCTACACGATTTTCCCGGACTGCAAATTTTTTTGX
CAAATGGAAAAGAAATTGCTGAAACCTTCTATTAATCATATAAATTGTCAGTGGAATCAT
GAATCAGATAGTGCAGGATTTTTTCTTTTTGATACTGATAATTTATACTATTATGTATTG
GATCAAGTGTCTTGGATATGTTTAAGAGATATAACTCTTCATTGTGATCGCATGTGGTTA
GCGGTTTGTTTTTGTTTGTGCAAATCTAAATTTGATGTACACAATATTCTAGCGGGAGTA
CATGTTATGTAATGAAAATGACGTCGGGGATTGAATGGATTGAGCCTTATTTGACATTTT
TCTGTGATTTTTTTGCCTTATTAGGAAATAAATTTGTGGCGCCAGTACGATGGAGATTGG
AATGACTCCTGCATTTACAGAAAGGAATTTGTACTGTGTTTTGCTTGACTTTAATTAAG
ATGGTATCAGCAGATATTTAACCCAATATGGATTAAGCCAAATTTATGGGCTTTCTCTGA
TTTTTTAAAAAAAATGGCCTTTATTTATGCTAGCGACTTGGCGTTGTTAAATTCTTACAT
CCCTGGTAATGTTTGTAACAAACTTGATATCATCAAGAAAGATCTTCCTGAAGATTTTAC
CGTGTCTATGTTTTGTGTCTTAGTGTGTTGGCTTGCTTCTTTCTGTAAAGGTTCTAATTT
AGCTGAAACTCGCCAGAATTGTCACGCGGTAAGCAAATTTCTGGCACAACTATCAAAATT
AATAAAACCCTAATTTTTAGTTTGTAAAAATAGAATTCAAATTTTTAACGCCACAATGAC
TTCGGCGGAGTTTTCTGTTGAAATTTCCTTATGTTTCTAAGCCAATTGTTCCATGGCCTGC
TTCGGCATCTTCTAATAATTCATCGAGTCAGAATATTGACTTTCCTGTTCTTAAACCAGA
TCAAGATCCAATAGCCTTCTTTCAAACTAACAATACGGCTTACTTACAACCTGGAGCTAC
TTATTACTGGAAGTGTATCGAACTGTCAAAGCCTATTCACATTTACGGTCAAGGAGCTAG
AGTACAACTTGTCGGACCTGGACCTGTGTTTGTTTTCAACAGTGAAAGTGTTATTCCTGA
AGATTTTACGTCGTGTTTGAAAATATCAACTTTATTGAAGATGAATTTCCTATTAGAAG
TGGCCAGTTAAGTTTAGGACTTACAACTCACAGTGCTGTATGGTTTATCAATGTATGGAA
AACTTCAATAGTCAATTGTAACTTTAAAAATTTTAGGGGAGCGGCTCTTTGGTATTCAGA
TAATAGAAATTTTTGGAATGCGAGAAAATGGAATCAGCAGCATTTAGTTTCAAATTGTCG
TTTTAATGGTTGTAGAATTGGAATTTCTAATACTGGTTCATCTGAATATTCCATAGCCAG
TCAAAATCAATTTTATGATTGTCAAATCTGTTTTAATGTAACCGGGGGTAATTGGTCTAG
AAATAATAATGTTATTGTTAACTGTAGATGTGCTTATCTGCATGTTGGAGATAACATGTG
GTATGAAGGCCATTCCGAAAAATAATAATCCCGCTAAGGGTACTTTCTGCAATAACATAAT
TAACCATGCTGATAACGGAGGCAATGTCTGGCCTACTCAGTTTAAACTTACAGATGGATC
AACGATACAGTTAGCATCATTTATTTTGATGATAATCAAGAAATTCCACCTTGTTATAG
CGGTAATTTTCATTGGTTTGGAGATGTAAACATTGTAAATTTTTCTACCACAAAAATTGA
TAAATGGTGCATTACTGGATGTAATTTCTATGGTAATACACATGCAGCTAACGATGCTGG
TCAAGTTCAGGTTGCTGAAGCTGTAAAAGACAAAGTGTTTATTATTGGGTGTTCTGGTAA
TAATGTAACCATGAAAAATATTGTAGAAGGTAACATGACTCCAAAAATTGGTACAATAAA
GTAAAAAACTTTTTATTCAAAACAAAATGGATTTACATTTAAACGTTTTACATATTGATT
CTGCGTATAAGTTCTTTTTCTAAACACTCTTCTAATTTCCATACATGCTTGATAAAACAA
ACTTTGTAAATTCATAAATATAGGTTTGACTTGATCAGAAGGTGAATAATAGCTCCATCT
AAATGATTCGGTAATAGGAACATTATTATATATTAACCAGCTATATTTTGAGTTAACTCT
TGCATGATCCACTATATCTTTAAGTACAGGGATAAGTGCACTCGGAAATCCAAAAGAATA
GTTTTTAATAAATCTATTTATCTGTGAAGAATCAAGCTGCGGACTAATAACATGACATTT
```

FIG. 13(A-1)

```
TGATTGAATTTTTAAATCCTTAATATTTCCTCTATCATGACGCGGGTTCATATTATGTAA
AACTACTACAACAGTGTAACCATTACATTTGGCAAATCTATTAAAAATTTTTGACGGTAA
AGCATGAAAGAAAGAACTTATAGAATGACATGATCCCAATTGATTCATACATTCATCTAT
TATAATACAGATAGATCCTTCACTTGCAGCTCTGCAGAATATATTATCTGGATTATCAAT
ATTTAGATTAGTATCGGAAATAGCATCTTTGAAAGCTAATTGTATAAATTTTGGATTTAA
TGTTTTTGTTAGTGGATTAGAGAATGCATCGTAGTTTCCTTCAACACACTGTGCTTTCCA
CGCAATTTTTTCTTCTAATGGAACAGTACCTTTTTCTGGAGTTATGAAAAAAATTGTTTC
TGGTATTGGATCAATTAGTTTTTCCAGATATAATATTTCTTATAAATTGAGATTTTCCGCT
ACCTGTGGGTCCATATACAGTAACAATGAATGGTTGTAATCCGCAGTTTAAACTGGGTAT
ACAGCCATCTTTTAACAGATTGTGAGCCTCATTTACAGTTTTTTGATAATTTACAGCAAT
ATTGTGTAAATCAGTCATAAGTTGACCATGATACATACATTTATCAAAAACTTCTTGACT
TTCTGGAAATGGATTTCTGCAAATAGAAGGATCTATCTTTACAACATCATTTTTCCAATT
TAATGTGTCACTTAAAAATTTTCCCAAAAAGGATTTTCTGTCAATGGTTCTTGCGGTCTT
GGATTTGGGTGTCTCTTGTCGTACGGGTAAAGTAAGTATCCTTTCTTCCACTGGATCCCT
TTCCTCATCGTTTGATCCTTCCAAGGTCTCAGAATTCTGGTTAGTTGCTTCTCTACCACC
GTGAATGGTACATCGGTTCCACTTGCGGTTTGCAGTGTCTTTTTTAAACTTTTCCTCGAT
GTCTGAAACTCTTTCTGTGGTTGTTCTAATAAATTATAGTCAGTAAAACAATGTTTTAGA
ATTTCATAGTTTAAACAATTTTTAGCATGACCTTTGGCTCTTAATTTTCCTTCTCCAATA
AATTTACAGTTTTTACAAGTTATGTCTTTTAAAGCATATAATTTAGGAGCTAAAATACAT
GTTTCTGAACTGAATGCTTCAGCTCCGCAACGGTTACAAACAGTTTCGCATTCAACCAAC
CAAGTTAGACATGGATGTTTTTCATCAAAGATTAAATTTGAGTTATATTTTTAAGTCTA
TGTAATCCTTTTGATAACATGAGTTGGTGGCCCTTTTCTGTTAAGAATAACGAGTCTGTA
TCACCATAAATACTTTTTATCTCCCTTTCTATGTAAGGTTTACCCATATCTTCCCCATAT
AAAATTTCTGCCCACTCACTCATGAAAGCTCTGGTCCAAGCCAGCACAAAGGATGCTATC
TGAGTTGGATATCGGTTGTTCTTGATCCATTCTTCCTTATCCTCAATAGTTGTTAAAATT
AAATCATTACAATCAGCAGATAAAAAAGTTATAGGCTTAAAAGTCACGTGATCTTGATTT
CCTATAAAAAGTGGAAAATTAAAAATTTTCATTTGTGTCTTTGGAATCTTTGGGCGGCATT
TCAGGTAGGTTTGAAAAATACTGATTCCACTCAAATGAACGTTTTGGTAATGATTACTA
ATCACAGTTGTGTATGATGTAAATTTCAGCTGATCCATTTTCTAATCTTTTTTTATCTTTC
TCTTCAATATTTTCAGCAAACACTACTTTCTTTTTATCTATACGGGTAGCAAACGAACCA
TATAAAGCATTTGATAACAATTTACTTATACTTCGCTGAATCTTGTTGTTACTTTTACTT
GCTTTTTCTTTAGCCATAATATTTACTTTCACATATTTTTGACATAACGGTTTCCAGTCA
CTCCATACAGCATACATTTCAGAGCTTTTGATTATTTTGCATTTCCATCCTCTATTGTGT
AAGGTGATTAAATCGATAGAGGTCAGTACTTCATTTATCAATGTTTCATTTGACCAGCAT
AACTTTCCACTTTTTTTAGAACATAATGGAGGTAACACATCAAGATAATCTAATGATGGG
GGTTCACAATCGGCTACCACAATCATAGGTTTGATTGAATTGTCAAAATAATCTATTTTT
TCTTTTCTTTGTAGTAGTTCTTGAAAGTAATCTATTTGTGCATTGGCTTCAAAAGCATTT
AAAGTTTTTCCATATGGAAGTGGATGCGTTAAGGCACTAGCATACATTCCGCAGATATCA
TACACATATATTGCTTCTTCAAATATTCCTAAAAATGAAGGATAACATCTTCCTCCTCTT
AAACTCATTCTAACAAAATCATACATTTTTTCTGATGGAGCTTCCAAATTTCTTAGGAAT
TCAGAGGCATGATCTTCTTCATTATAAAAGATTTGTTTAAACAATGCTTGAGTATTACTA
CTAATTGTAGGACGTTGGAATATATTAAAAGAACACTCAAGCTTTAAAGATGTTGTACAG
AACTCTTGATAACCTTCTATAAGTTTTTCAACTAATTGAGCCGTAACTATAACATCATCA
ATACAATACTCCTTAGCTTCCTCTAATAAGTTGTATTTTTGGTTGTGTTTTGGTTTGTTT
TGTAAATATTCTTCAAATGAATTCCAATATTTTTGAACTGGATAACCATTGTTTTTCTTTT
TCATATTCTCCCAACATAAAAAAATCATTGATTGCCCTGTAAGGACAATAACCTTTGCTA
ACACTCAACTGATATGCAGTAGCAGCGTCTCTTAAAGAAGAGTGGGTTAACAAAAATGTA
TCCCTAACCATAAATTTTATACCTTGCCATTTCATATCTTCAAAATTAATAATTCCATTT
TTCCATCTTTCATAAGTTGTATGTGAAGGTTTCTTAAAGCAAGGATTTGGAAGAGATAAT
GTAATATCATTAAATAACAGTTTTCCAGCACGAGGCATAAAGCTTCTTGTCAGCTTAAAC
ATTGAAAGTTCTTCACTGTCTATTCCTTCTAATACATGACTTGCAAGTATGATTTCATCA
AAACCACAGATATTATGACCTACTACATATAATTCAATATATCTTGGTTCGCACTGTTTT
AATTTTTTTTCTTTATTTAAGACCATGATGTCTTCATATGATAAATTTGATTCAAGACCA
TGATTTTCACAAAACGTTGACCAGTATTTTTTAGCTACTGAAATTTGTAGCTCTGTTCTG
AATTTTTTAAAAGCTATGCCAATTTCATCTTCTTTTTTATTTAACATTACAAAACATTCT
CTGTTTACCCTCATAACCTATATCGGTAGCTATTTTAGAAGCAATTTTTATGAGTGATTTA
CATCCAATTAACTTAAAAACCAACAAGTAAGGAGTTAACTGTTTTCCATACAAAGAATGG
TAAGTATATGTTTCAATATCATAAACAATAAAAAGACGTTTTGCTTTTATGGCTCCAACT
GGATTAAATTTGATTTTTTCCCACCAGAGTTTTGTTTCATGGTGAATATTGTGATAATAG
AAGTCCCGTCTTCTGGATCAGCAGTTGTGTATATTACTATAAATTGTTCCGCAGAATTCA
CATTTATTCTGTTGTTTAACAGTTTTTATTAAATATATTTCTCCTTTTAAAATCAATAAT
TCTATTGGTAACAAATTTCCATTAAGAAATTTCTTCAGTCATCTTAAAAAATCTTTTGTTG
AACTTCCATATTTTTAAAGATACGGGGGTGTTAGAATCACAAAGTTTTAAAACATCTAAA
```

FIG. 13(A-2)

```
ACATTTTCTACTTTCTTGAAAGAATTTAATTTTAAACCCTGAATTGCAAAGTAATTATAA
AAACTTTTTTCAAAATTCTTGTAGTATATAATTTTTATATATGTATCCTCATATATTCCA
GTAATATAAGTAGTAGTTCTTTGCTTTATTATTGTCTTTGAAGCCATCTGTTTAAAGCCG
CTTCCCGTACTCGCTCAAAGCTTCTTAAAACAACTTCATTTGTACTATAGCCAACAATTC
CAGACAATTTTATTCTAAATGCTATTTCAACTGAATCTAAATCTGAAAAATCCGTGTTTA
CTTGGTTGATTACTTCTTCTATGCTCCCACTGTCTTCTACGAAGTCTATATCTTGAAGTA
ATTGGTCTCTTTCTTCTGGAGTTGAAAAAGAGTAAGATCTTTCATTAGCTTCTATAATTC
CTAAAAAATCACGAGTTATTCTGCTATATAGTTGTCTGAATGCTTGTGTTTCTCTATTAA
ACCAAACTCTAGTAAATATATCTTCTCCACTTTCATTTCTACCTCTTAATATAATTTGAA
CAAATTGGATTCCAATATTTCTGGCAGCTAACCTATTTTGCACTAAATTTAAGTATAAGT
AATATAGCGTGCTTGCCACATGCTCTAATATAAAGAAATACACTAACCATTTTTGAATAA
AATCATCAGTCAATCTATTTTCATTATAAAATCTAATAAGTAATTGAAAAAATTCACTTC
CGTAATTAAAAAAATTACTCCTTCTTGCTTCAGGAGTTAATTCTTCTTCTAAATTTTGAA
TTAAATCTACTATTGAAGCTATCACTTCATCATTAAATTCTTCCCTACTCAGATCGCTTG
AGCTCGGCTCGCGATCTGAAAATCCTTCATCTTCTATTTCAGGAACAGTAAGAGGAGAAC
TAGAAGTTTCTTCAACATTCCTTACCCTTTGGCGTCTATTAACAGGTAATCTATCAATAA
ATCTTCTGATTACATCACCCCTTGAACGTCTCATTATTTCAGTAATAGCTCTATAATTTT
CCCTAGGTCTTAATCTGAATGGTAATCCTACTCTTGTCCCTGACCTTAAAGTTAATGCTC
CACCATGCATCCCACCTTTTCCTAAAGTTAATACAGTTGCTAAATCTTTTAAATTAATTG
GATTTTCAGCTTCTGGAATTTCCAGCTGTGAAAATTCATCTATAAAAGCTCAATCCAGA
ATTCAGAAAAAGGTAAGTCTAATATACATTCACTATTATGCATGTTAGACAAAATTAAAA
ATTTACATAAAGCTTTTTTAATTTTACAAATTAACTTTATAAGGTAAGTATCCCTTTCTT
GCAAATTTAAAACCATAAAAGCTTGAGAAAAAAGGTTGATAAATGCTGCTGAAAAGATCTAT
TCTGATTTTGAGCTGAAATAGCGGAGCCAAAACCTTGCATGTCTGCAAGTTGCAGACTCG
CTAATATTCTATCCATTAAAACCGCGTTTTGAATTTGACTAATTGTTTGTGAAAAATTTT
CTACATTTTGAATTGCTCTCATATATGACCCAGTATTTATGGAGTATGAACAATCAGTTA
AAATTTGCCAGGTCATGCGTCTCTCAAAACTTATAGGTGAAAGATACAACTTATATGAAA
TGTTGCTGTAAGTCCGCTGATCAAACAGATACTGGTTTAAAACTCGCGCCACATAAAAT
ACCCAATTAATAAATTTGGTGGAGGTTCTCCTTCAAATGGTGGTTGTGAAGTAACAGGTG
CTCTTGGGCGTAAATCGAGTAATTGAGTCACTGGATAATTAAAAAATCGATTAGCCCATT
TTATTCCCCTTTCATGTATAGTCCTTGACCTGGCAATACTTCGATTATTAAGGTCAAGTG
TTAAACGTAAATATCGTAAGGTATGTTGACTTTGCCCAGTGAGTTGTTGCCATTGGTGAA
TCTGCAAGGCAAACAAAAAATTTATCTTATTACTGCAGATGCATCCTATTTTACAAAATT
TACGTTCATCATTGGAAACTCCAGACTTATCAAGCAACTCCCCGGGCACGTCAAATAAAA
ATGAAAAGATGAATTTGAACCAGCAGTTGGCATTTCTAGCAAACCATCTGATGAATTTA
ATATGAGACGATCTCAAAGAGATGATAATTTACCTAAAAGTCAGATACCAGTAGTAGATA
TACTACATGATAAAAATCCTAAAATGGCAGAAGAACGAGACTTAATGTATAAATCTTCTG
CTTGCATAAAACTTGATGATTCTAAACAATTAAAAACTGATATGTTCAGGCCGGATTTTG
CTGGAACTAGTCCAGCTCAAAGACACATAGAAGCCGCAGAGCTAAAGAGAAATGGATCTT
ATACTCGTAGTTTAGAACAATGGACACATGATTCTTTTATAAGTCATGTTAAACAATTAG
TTTCTAGACCATTTATATCTCTAGGTATTACATATTTGGATGATTTTTGCAGACTTATT
TAGATCATACTGAATCGTCTTCTTTAAACTTTCAACTGTTTACTTTAATAAATCACTGTT
CAGAAAATACTTTAAAACGGATTTTAAAACACATTTCTAAAAAAATGAAAAAATCAAT
ATGTAAATCAATGGTTGATTGATCTCATTACATGTATATATCTAATTATAAGAGATGAAC
AAAATGTTACAGAACAAGTTAATGCCCTTTTAGTAACTAGTAATCACTTAGCTTTACATT
TTGCAAAGAAAGCTACAGGTGGATTCTATCCTACAGCAGACAAGTTAGCGAAGACTCATA
TTTTTTTTCAAGAGAATAATTTTAGGAATACTTTCGCTAGCAGAAAGTATAGGTTGCTATA
CTGTGAATCCATATTGCAAAAATCCTTTGAAAAAGTCAAAAGTAGAAGTAGAACCAAGTG
ACGAAATGTATATGTTCAGCTTAAAAGGTGCACTTGAACATCCTGATTCCGACGAAGACG
AAGACAGTGGACTTCAAAATGAATAATTATCATAAATGGACTTCTAATGTTATAGATGCA
ATTCTATCAAACAAAGCTCTTTTAGCTATAAAAATTTTAAAAGTCAACCGTTTGCAAACA
AATTGAATGCTTTAGAATCAGCAGTTGTGCCTCCAAGAAAAGATGATACTCCTGAAATGA
TAGCAAATCTTTTAAAAGAATTAGTTGCTTTGGGAGCTATTCGCAGTGATGAAGTTGGCC
CATTATATTCTGACCTTCTTATCAGAGTTCACAAATATAATAGCTTGAATGTTCAATCAA
ATTTGCAAACTTTAACAGGAGACATTAAATCACTTCAATCCGATATAATTAGAAGTTCCG
ATATTCCCAATTAAGTAATCAAGTTGTTTTAAATACATTTTTAAATTCTTTGCCCTCAA
CTGTTACATTTGGACAACATAATTATGAAGCTTTTAAACAAACTCTAAGATTATTTGTTA
ATGAGACACCTAATATTACAGTTTTTAGATCAGGAAATGATACTTTAATTCAGGTTAACA
TAACAGGAATTCATACAATTAATTTGAATGATCATTTAAAAATTTAAAAAATTTTTGGG
GAATGATTATTAACAGGTGAATTTATTCCAGGTGATATTACAAGCAGACTAACAGCTAATA
CAAGAGTACTGCTTTATTTTCTTGCTCCTTTTACAAATGATAATACATTCACACCTGATA
CTTTTCTAGCTTTACTCATGAAATTATATAGATTGACAGTTTCTTCTGCTTTAGATTTTG
AAGAAGAAACTGAAGCTGAAGTAGAAAATGTAGCTCAACAAATAGGATCG
```

FIG 13(A-3)

```
ACTAGTGCAGATTTTACAAAGACTTTAGGATATCTATTAAAAAACAAAGAAGAATCATTT
TCGCCTCCCAAATCATTATCTCCTAGACAACTGGGTATTTTAAGGTTCATACAGAAAAGT
CTGGTAGATAAAATTGATAGAAATAATGAAGATCCATGGGATGCTTTAGAAACTTTATCT
TATTCATTTTCTCCGTCATTTTATGAGGCCAATGGGCCTTTTATTAGACGGTTAATAACT
TATATGGAATTTGCCTTACGTAATTCTCCTACTTACTTCAGAGAAATTTACTCCAACAAA
TATTGGATACCACCCAATTCATTTTGGACTCAAAATTATGCAGACTTTTTTTCGGAAAAG
AAAGAAAAACAAAATTTCGAAACATTTGAACCGCGGGAACTTCCTTTACAAATCTCTGAG
GAAGAAGCTGTCCCGCATACAGAAGATTTTCAGTCAGCCATCTCGCCCTCTATGGGCCAA
ACTTCACTCCCTGCTCCTTCTGTGTCAGAATACAGTAGCGTGCCTCGGTCAGCTTTTTAC
CCTCTCAGAGAACGTATCCAAGAGAGCATTTCAAAGGCAGTCATCCCTCCTTTGACAGGC
TATGTCGGAAAACAAATAGGTGAAACTATTTTCCCTGGTAGTGGAGATCTTGTAGCACCC
GCTGCGTCTTTAGTTGCAGCACAATTGGTTGATTCAAGGTTTAATAACAGAAGACAAAGA
TTGAAAGACGCAGCCAGAAAGCGTCACCGCTATGTTAGAGAGATGCATAATATTTCTGAT
AAAGAGTCAAATGCTTCTAATGATACGGTAATATCACCTTTGATTGGACATGGTTCGCGC
ACTGAAAATCGTTTTGAATATTTGAGACCTAAAGGTGGAAATTATTTATACTAATAAAAA
TCATAACAGACCTGACGGGCGGTCATCCTTTTTTATTAGATGCAGAAATTTGTACCTCCA
CCACGAATCCTTGCTCCAACAGACGGTAGAAACAGTATTACTTATACGCCTCTGGCACCA
CTGCAAGATACAACAAAAGTATTCTTTATTGACAATAAGTCTTCGGACATTGAAAGTTTA
AACTTTACTAATAATCACAGTAACTTTTTTACAAATATTATTCAAAATGCTGATTTGGCA
GCGGATGAAGCAGCAACGCAAGATATTAAACTGGATGAAAGATCTAGATGGGGCGGTGAA
CTGAAAACTTTTATAAAAACAAATTGCCCCAATGTTTCAGAATTTTTTAACAGTAATAGC
TTTCTAGCCAGATTAATGGTAGATAAAACTGATCCAGAACATCCTAAATACGAATGGGTA
CAAATTACAATTCCTGAAGGCAATTACACTGGAAGCGAACTTATAGATCAACTTAACAAT
GGTATTTTAAACAATTACTTAGAAGTGGGACGCCAAAAAGGAGTAGAAATTGAAGACATA
GGAGTAAAATTTGATACAAGAGATTTTTCACTTGGATATGATCCTGAAACGGGACTAATT
ACTCCAGGAAAATATACATATAAAGCTTTTCATCCAGATATTATCTTGCTACCTGAATGT
GGCGTAGATTTTACATATTCTAGAATTAATAATATGTTAGGTATAAGAGAGATTTCCA
TATACTAAAGGATTTCAAATTTTATACAGTGATTTGACGAAGGGAAATATCTCTCCATTA
CTGAATTTAAATAACTATCCTCATTCTATCGAACCTGTAATGCAAGACGAAAATGGAGTT
AGCTATAATGTAGAAAAAATAAGTGACAATCCCCCCAGATGGCAAACAAAGTACAGATCT
TGGACTTTAAGTTATAAAAATAATGGAGGAGCTAAAGCCCTAACTGTACTAACTGTTCCG
GACATAACAGGAGGATTAGGTCAAATTTATTGGTCAATGCCAGATACTTTTAAAGCACCT
ATTACTTTTACTAACAATACTACAAAGCCAGAAACACTTCCAATTGTTGGATTACATATG
TTTCCTTTAAAAGCAGGGTTAGTTCATAATATAAATGCGGTTTATTCTCAACTTTTGGAA
CAAATTACAAATACAACTCAAGTATTCAATAGATTTCCTAAAAATGCTATACTAATGCAA
CCACCTTACAGCACCGTAACATGGATAAGTGAAAATGTCCCCTTTGTTGCAGATCACGGG
ATTCAGCCATTAAAAAACAGCCTTACAGGTGTACAAAGAGTTACTATAACAGACGACAGA
AGGAGATCTTGTCCATACATACAGAAATCTTTGGCGACTGTTGTCCCTAAAGTACTTTCA
AGTGCTACACTTCAGTAACAATCTGGCTGATATCTCTGGGCCTTATCCTCCTGGAACCGT
TATGTCTATTTTAGTTAGTCCCTCTGATAATACCGGGTGGGGTATTGGAACATCAAGTAT
GAGGGCTACTGGCTTGAAATTTTCTAAAAAACAACCTGTTAGAGTGCGACCTTATTACAG
AGCTCAGTGGGGACAGCTTAATGCTCGTACTTCACTTGAGAAACTAAAAACCAAATTGAA
ATATTATGAAAAATTGTACAGGGACAGACTAAAAAGAAAAACAGTTGTTCCAAAGAAAAA
GAGGTCACCTACATCTCCTGCGGATCGACTTAAAAAATATCTTAAAGCTGTCAGTCAAAT
CAAAGCTTTCAATAGAGCTAGAAGAGCAGCCCAATAAATATTATTTTTCACTTGCAGATG
AAGGTAGTTCACGTGCTTAAATCTCCTCATCGTCGAAGACATACACGTCGTTACAAAAAA
CTAAAAAAAATCAATCTATCTCCATACATTTTACCTAAAGAATTGCAAGGCGGTTTTTTA
CCAGCTCTCATTCCTATCATAGCAGCCGCAATTAGCGCAGCCCCTGCTATAGCTGGAACT
GTAATAGCTGCTAAAAATGCTAATCGTTCTTAAAAATTTAGAAAACTTTTTTTTTAACAGA
TCACATGGCTTTTTCAAGATTAGCTCCCCATTGCGGCTTAACACCTGTTTATGGCCACAC
CGTTGGAATCTGTGATATGAGAGGAGGTTTCAGCTGGTCTAGTTTGGGAAATTCTTTTAC
TTCTGGTTTAAGAAACATAGGTTCATTTATATCAAATACTGCTCAAAAATAGGTCAATC
ACAAGGATTTCAGCAAGCCAAACAAGGTCTACTGCAATCAAATGTTTTAGAAAATGCAGG
ACAATTAGCAGGTCAAACTTTAAATACTTTGGTAGATATTGGAAGATTAAAGGTAGAGAA
AGATCTAGAAAAATTGAAACAAAAAGTTATAGGGAACGACCAACAAATTACTCAAGAACA
ATTAGCTCAACTAATAGCCAGCTTAAAACCAAAGATGAAATGTTTGTAAAGCAATCAGA
AAAATTGTTGAACCTATGAGACCAGAAATTAAATCTAGCCAAATGCCTGTAGAAATGTC
TTTTTTATGATTCTGTAAGTGATGAACCAATCATAAAAACCAAAGAAGTTAGCCCTCCTTC
ATTTTCATCTGAATCTTCACATTCATATTCTCACCCAAGAAAAAGAAAACGCGTATCCGG
TTGGGGTGCATTTTTGGATAACATGACTGGAGATGGAGTAAATTTTAATACAAGAAGATA
TTGTTATTAAAAACACTTTTTATTTACAGATGGAGCCACAGCGTGAATTTTTTCACATTG
CGGGTAGAAATGCAAGGGAATACTTGTCTGAAAATCTGGTACAATTCATCTCTGCCACTC
AAAGTTTTTTTAATCTTGGAGAAAAATTTAGAGATCCTTTTGTAGCTCCATCGACGGGTG
```

FIG. 13(A-4)

```
TAACTACTGACCGTTCTCAGAAACTTCAACTTCGTATAGTTCCGATTCAAACTGAGGACA
ATGAAAACTTTTACAAAACTAGATTTACTTTAAATGTAGGAGATAACAGAGTTGCAGATC
TTGGAAGTGCATATTTTGACATTGAAGGAGTTATTGATAGAGGACCTACTTTTAAACCTT
ATGGAGGGACAGCTTATAATCCATTAGCCCCAAAATCAGCTTTTCCCAATGCAGCTTTTA
TGGATACTGATGAAGCTACAACAATTTATATTGCTCAACTCCCTAATGCTTATAATGCTC
AAAACAAAGGTGTAGAAGAAGCAATTCGAGTAGAAGCAAACACTACTACTCCTAATCCTC
AATCAGGAGAATATGCTACTTATGACTCTGCCAAATTTAATCCAGAAACTACTGGTGCTT
CTGGAAGGCTTTTAGGAATTAATAGCTTAGGAGATCTTTTTCCGGCTTATGGATCTTATT
GTAGACCTCAATCAGCAGATGGTAACATTTCAACTGCACCCATAACTAAAGTCTATCTAA
ACACTACTGCTACAGATGACAGGGTCAGTGGAGTTACTGCAGTTGACACCGCAACCAGAT
TGCATCCAGATGCTCATTATATTGAATATACTGATGAAGCCAAAGCTACAGCTATAGGAA
ATCGCCCAAATTATATTGGTTTCCGAGACAATTTTATTGGACTCATGTTCTACAATAATG
GTTCTAATGCAGGAACATTTTCCAGCCAAACACAACAACTTAATGTTGTTTTAGACTTGA
ATGACAGAAACAGTGAACTAAGCTATCAATATCTAATAGCAGATCTGACAGATAGGTATA
GATATTTTGCACTTTGGAACCAAGCAGTTGATAGTTACGACCAGTATGTCAGAATTTTGC
ATAATGAAGGATATGAAGAAGCCCTCCGGCCTTATCATTTCCTTCTCAAGGTATCCAA
AATTATTTCATGCCTACTGCGGCAGGTAATGCGATGACAGTAGACACGGGTAGAAATACT
GCAGCAAAAACAGATAACACCAAGGCTTTTATAGGATATGGCAACATGCCATCTTTGGAA
ATGAATCTGACAGCAAATCTACAACGTACATTTTTGTGGTCTAATGTAGCAATGTATCTG
CCAGATAGGCTGAAAACAACACCACCCAACATACTACCTGATGACACCAACTCTTAC
GGATATATAAATGGAAGGGTCCCTCTAGCAAACATAATAGATACATGGACTAACATTGGG
GCTAGGTGGTCATTAGATGTTATGGATACTGTAAATCCATTTAATCACCACAGAAATTCA
GGACTAAAGTATAGGTCACAACTGTTAGGAAATGGAAGATATTGCAGATTTCACATTCAA
GTACCTCAAAAATTTTTTCCTATAAAAAATCTTTTGTTGCTGCCAGGAACATATAATTAT
GAATGGTACTTTAGAAA
GGATCCCAACATGGTTTTTCAGTCTACTTTAGGTAACGACCTTAGAGCAGATGGCGCAAC
TATTACATACACCAACATAAATTTATATGTTTCATTTTTCCCTATGAATTATGAAACAGT
AAGTGAACTTGAATTGATGTTGCGTAATGCTACTAATGATCAAAACTTTGCAGATTATTT
GGGTGCGGTAACTAATCTTTATCAAATCCCAGCTAATACAAATACTGTAGTAGTGAACGT
ACCAGATAGATCTTGGGGTGCTTTCAGAGGATGGAGTTTCAATAGAATTAAAGCTTCAGA
AACACCTATGATAGGAGCAACAAAAGATCCAAATTTTACTTATTCAGGATCTATACCGCT
ACTAGATGGTACTTTCTATTTAACACACACTTTTCAACGAGTTTCTATTCAGTGGGATTC
TAGCGTTCCATGGCCAGGAGATGATAGGCTTTTGATTCCAAATTGGTTTGAAATTAAGAG
AGATCCTAATATGGACGCAGAAGGTTATACTATGAGTCAAAGTACTATCACAAAAGATTT
TTATTTGGTACAAATGGCTGCTAATTATAATCAACTTATCAAGGTTATAAATTGCCAGT
ACATTCTAAATATTATGGATTTTTAGAAAATTTTCAACCTATGAGTCGCCAAGTACCAAT
TTATGGTAATGGCACTTATGATTTATATACTGCTTATATTACAAACCAAAGAACCATGCA
AATTTGGAATAATAGTGGTTTAGAATCTAAAACTTCAAATCCTCCTATGTTATCCAACAC
TGGTCATCTTTATGTAGCTAACTGGCCATACCCTTTGATTGGACCAAATGCTATTGAAAA
CCAACAAACTGAAAGGAAATTTTTGTGTGATAAGTATATGTGGCAGATACCATTTTCTAG
TAATTTTTTGAATATGGGTAATTTAACAGATTTAGGGCAAAGTGTTTTGTACACTAATTC
TAGTCATTCACTTAATATGGTTTTTACTGTGGATAGTATGCCTGAAACAACTTATCTAAT
GCTTTTATTTGGTGTTTTCGACCAAGTTGTTATTAATCAACCAACAAGAAGTGGAATAAG
TGTAGCTTATTTGCGCCTTCCTTTTTCAGCTGGTAGTGCAGCAACATGAGCGGCACATCC
GAAAGTGAGCTGAAAAATCTGATTTCATCATTACATTTAAATAATGGATTTTTGGGCATT
TTTGATTGCAGATTTCCAGGTTTTCTGCAAAAATCTAAAATTCAAACTGCTATTATTAAT
ACAGGTCCCAGAGAACAAGGCGGAATACACTGGATAACATTAGCATTAGAACCCATTTCT
TATAAGCTATTTATATTTGATCCACTCGGATGGAAAGACACTCAATTAATTAAATTTTAT
AATTTTTCACTAAATTCTCTTATTAAAAGGTCGGCCTTAAATAACTCAGACAGATGTATT
ACAGTAGAAAGAAATACTCAAAGTGTTCAATGTACCTGTGCGGGATCGTGCGGCTTGTTT
TGTATATTTTTCTTATACTGTTTTCACTTTTATAAACAAAATGTATTTAAAAGTTGGCTT
TTTCAAAAATTAAACGGTTCAACCCCTTCTCTGATCCCATCTGAACCACATCTATTACAT
GAAAACCAGACATTTCTTTATGATTTTTTAAATGCAAAAAGTGTTTATTTTCGAAAAAAT
TATAGAACATTTATTGAAAATACTAAGACTGGATTAATAAAAACACATTAATTGTATTCT
TGCTTTTTGACGTTTTCATTAGTCTTCATCTTCATCTTCTTCTTCACTGCTAGATTCCAA
GATGGTTTTTTTTTTCTTTGATGGAGTAGGCTCTTCAATAGTTCCAAAAGGATTCATATC
AGAATCCTCTTCTATGTTAGGCAACATAGTATTTTTAACCTGGAATGACTGATTCCACTT
AAATTGAGAAAACTGAATTGGAATGTTATTTCCCATACATTCATTCCAAAATTTACGCAC
AAGAGTTAAACACTGTAACATATCTGGCAAGCTAATTTTCATCTCACAAAATTTTCCATT
ATTACGTCTCAAGTTGTATTGATAGTTACAACATTGAAACACAAAACAGCAGGGAATGT
AACTGCTGCGGCCTGAACTCTATTAACATCCTGAACATCAATTCCTTCCACTCCAGATAT
AGAAAATGGAGTTATTTTAGGGAGTTGTTTTCCTATTGTTTGTTTGCCACCATAATTACA
TTCACACTGACCCAATATAAAAAGCATATTTCCGACTTTAGCTTTCGGAAACACAGCTTT
```

FIG. 13(A-5)

```
TGTAGTTTCAATGGCATTTTGCATAGCCAGCAAGGCCTTCTTTTCATCTGAAAAGTTAAG
ACCACAACTGCGAGGAGAACATTGCCCAAAACGCTGATGGGCATCCTCAGCACATAACAC
GTAATGTTCCTGAACTATTTTTACTACTTGTTTATTCATACGCCCATTACTAAGAACACC
CCTCCCTTCCTTTAGGGCTTGCACCCCTGCTTCCGATGTTGGAGGCATTTCAATTTCATT
CACCCTTTTAAACATGAAGTCACCATGAAAACATCTAGGACGGTCCTCCTCCCAATCATG
ATACCACAAATAACAACCAGAAGCATTAAAGTTTGGAATCAAGTCAATTTGCTTACAAAT
TGCACTATATAGCATTCTACCTCCTACAGTAGCCATAGATTTACTGCTACTATAAGTCAA
ATTTATAATTTTCATCTTTTTCATGTACTGAGCAAATAATTTTTCACAATCTCCTTCTTC
AGGATGAAACTTCATTTGACTGGTATCAACTTTAACACACTCTCCAAATTTAGCTAAAAT
TTCGAGCGCCGCTTGAACTTTATTCTGAAATTCTTCTGTAGTAGATTTTCTCTTCTTGAT
AGATTTAGTAACTTTTTTAGAAGACATTATGTTAGTTTTTTTCTCGTTGTAGGATGGCTG
AAAAAAATATGGGAGAGTCAGAGAAGGGTTTGAACGAAGAAGAATTTAACTCTATTCTAT
CAAAACATCTGGAAAGACAAATTAAAATCTGTAAAGCGTTAACATCAAAATTATCGAACT
GGAATATTGGAACATTGTTAGAAAACTTGTTATTTTGTCCTGATGAAAGACAATCATCAG
GTGATCCCGACCCAAAACTAAACTTTTATCCGCCTTTTTTAATTCCGGAATGTCTTGCAT
TGCACTATCCATTTTTTCTAACAACTCCTATTCCGCTATCATGCAAAGCGAACAAAATAG
GAACTAACACTTACCGAAAATGGATGAACAATCAAGTCCTGGATTTACAAATACCTTCCT
TGGAAAATTGCAAATGGGATGATAGCTTGGGAAATGTAGATTTAATTGAAGAGCTTAAAG
AGAACCAAAAACTTGTTTAGTAAAACAAGACCATGAAAGAAATATATGGTTTAAATCAA
AATGCAAACAACTTCAAAGTTTCAGCTATCCCTCACTCAGTCTGCCCCCAGTTTTACAAC
AAGTTTTAATTGAATCTCTTATCGGCATTAGTCAGGATCCTAATAACTTTGACAAAAATT
ACGAACCTGCAATAACTCTAGAAAAACTACAACATGTAAACTGTGATCAAGATTTAAAAC
AAGTTCAACAAAAAGTATCTTCAGCCGCTACATACGGAATACTTTTGAAATGCATTCAGA
CTTTATTCAGTGACAAATTATTCATTCAAAACTGCCAGGAATCATTACATTACACCTTTA
ACCATGGTTATGTAAAATTACTTCAATTTTTGACAAATGTCAGTTTAAGCGAATTTGTAA
CTTTCCATGGTTTAACACACAGGAACAGACTCAATAATCCGCAGCAACATACACAATTGG
CAACCGAAGACAAAATAGACTATATCATAGATACAGTGTATTTATTTTTGGTATTTACGT
GGCAGACAGCAATGGATATTTGGAATCAAACATTAGATGATAAAACAATAAATATAATTA
AAGAGGAATTAAACCAAAATTTTGAGAAAATTGTCAAAGCTGAATCAGTTGATGAAGTTT
CTGAAATTTTAAAGTCTATTATTTTCCCTGAACTCATGCTGCGAGCTTTTTGTTCTAATT
TACCTGATTTTATAAATCAGAGTCAGATATCAAATTTTAGAAACTTTATCTGCATTAAAT
CCGGCATACCGCAGTCAATTTGCCCCCTATTACCTTCAGATCTAATTCCTTTAACTTTCC
TAGAAAGTCATCCAATACTCTGGAGTCATGTAATGTTACTAAATCTTGCTTCATTTCTAG
TAAACCAAGGCAATTATTTGCATGAACCCGAAAAACCTTTAAATATTTCATCAGTTTACT
GTAATTGTAATTTATGCTCTCCGCAAAGAATGCCATGTTACAATAGCAGTTTGATGCAAG
AAATACTAACCATTGATAAATTCGAGTTCACAAACTCTGATAAAACAAAACAGCTAAAAC
TGACCCTCCAAACTTTTGCTAATGCCTATCTTAACAAAATTTAACTCAGCAGAATTCTACC
ATGACCAAGTTTTATTCTACAAAAACTGTAAAAGTAAATTTTCTAACCAATTAACAGCTT
GTGTAATAAAAGACGAAAATTATTGGCTAAAATAGCAGAAATTCAAATAACGCGGGAAA
AAGAACTCTTAAAAAGAGGAAAAGGAATTTATTTGGATCCAGAAACAGGAGAAATCTTAA
ACAATGGAGAAGCCATATCATCCTCTGAAAACTTCCAAAGGCAAAGAACTAGCTATGCTC
TACCATCAAATGAAGGAGAGCGAGCTGGATGGGAAGCCGATGAGCGAAGAAGACGAAGGA
GAAGTGAGTGAGGATGAAACAGAGACAACAATTCCAAAGAAAATGAAGTTTACAAGTAAG
TAAGCTCTAAATTTTTATATTAAAAACTGAATTTTTTTAGACAAAATTATTTTAAATTA
AATCTTTATAGCTAGCAGTTGATCTTTGTTCGTTTTTCAGAAAACTCAAGTGTTCAGTC
ATATCAAGTTCACTTGCCTCTGAAACACGAAATTGCGGAAATTCTAGAAAAAATTAGACT
AGAATCTAAAAAATATCCAGGAAAAGTTTATCAAATAAGAAATAGAACTCCAGCAAGTAT
TACAAAACGATACCTGTATGAAAGAGATCTGAAGAAACTGTTCCAGTATCTAGAAGACGC
AAAGAAGCTTTACGCTAAGTACCAAAGCTGAGGCTTTATAGTTTTAAATTTTCCGCCAT
GGCTCAACCAGTGACGCCTTACGTCTGGAAATACCAACCAGAAACAGGATATACTGCTGG
AGCCCATCAAAATTATAACACTGTTATCAACTGGTTGCATGCCAATCCACAAATGTTTGC
CAGAATTCAACATATAAACACCGCACGCAATGTTATGGACAAATTCCGCTCTGATTTGAC
CCGAGATGACATCGCGGTTAACATCAACAACTGGCCTGCAGAGGATTTAATGCAACCTCC
TAATTTTCCTTACATTCCTGCGACCTCTAAATCCGCTTCAACCATAAATGACTGGTTGGC
TACCACTCAAGGAATTCAACTCAGTGGAACTAGTGAACTAAACGGGTGGGGATCTAACCG
CCTGACTTCCTATCCGGATATTCCACCCATTTAAAGTATGAAAGGCCTGGTCAACAACT
TCAAGGCCAAGGACTTTTTAAGCAAGAAAATATTCATTTATTTTACGAATCTCCGCGCCT
CCCTCGCTCTGGAGGATTAACTCCCCAACAATTTGTAAAAGAATTTCCGCCTGTTGTTTA
TAATAACCCCTTCTCAGAATCTATGAGTGTATTTCCGAAAGAATTTAGTCCTTTGTTTAA
CCCTTCAGAATCTTTGAAAAAAACATCCAGTCAAACTTTACAATATAAATAAAAAACTTC
TATTCATCTTTATACTTACACTAAAGCATCGCGTTTATTTTCGTCGCCATAAAAATATAT
CAAAGACCCGTAATTCTCTAACTTTAAATCATTTTTTGAACTAATCTTAATCCATTTAAA
TGTAGGAATTAATATATCAGAAACCAGTAACAAGCCAGAATTAAAATATACTTGTGTCAT
```

FIG. 13(A-6)

```
TTTTACAGATGAAGCGAGCACGCTGGGACCCGGTTTATCCCTTTTCTGAAGAGAGACTGG
TTCCTCTGCCTCCTTTTATTGAAGCCGGAAAAGGGCTAAAAAGCGAAGGGTTGATCTTAT
CTTTAAACTTTACTGATCCTATCACTATAAATCAAACCGGTTTCTTAACTGTAAAATTGG
GAGATGGAATATTCATAAACGGAGAGGGTGGCCTATCAAGCACTGCTCCAAAAGTCAAAG
TTCCCCTGACTGTCTCAGATGAAACATTGCAACTGCTATTAAGTAATTCTCTAACAACTG
AGTCAGACTCTTTAGCTTTAAAACAACCGCAACTTCCCCTAAAAATAAATGATGAGGGGA
GTTTAGTATTGAACTTAAATACTCCTTTAAATCTACAAAATGAGAGATTGAGTTTAAATG
TTTCAAATCCACTAAAGATAGCGGCAGATTCTTTAACTATAAACTTAAAGGAACCCCTAG
GATTGCAAAATGAAAGTTTGGGCTTAAATCTAAGTGATCCTATGAATATAACTCCAGAAG
GAAATTTAGGTATTAAATTGAAAAATCCTATGAAAGTTGAAGAAAGTTCTTTAGCCTTAA
ACTATAAGAATCCTCTCGCCATTAGTAATGATGCGTTAAGTATAAACATTGCGAATCCAT
TAACTGTTAATACAAGCGGATCTCTAGGAATATCTTATTCTACTCCCTTACGAATTTCAA
ATAATGCTTTATCATTATTTATAGGAAAACCTTTAGGATTAGGAACTGACGGCTCTTTAA
CTGTAAATTTAACTAGGCCTCTGGTATGTCGTCAGAACACTTTGGCCATAAACTACTCAG
CCCCACTAGTGTCATTGCAAGACAATCTTACTTTAAGTTATGCTCAACCATTAACTGTAA
GCGATAATTCTTTAAGATTGTCTCTAAATTCTCCACTAAACACAAATAGTGATGGAAAAC
TTAGTGTAAACTATTCTAATCCTTTAGTTGTGACTGACTCTAATCTTACCCTCAGTGTTA
AAAAACCTGTAATGATTAACAACACAGGTAATGTTGACTTAAGCTTTACAGCTCCCATAA
AATTAAATGATGCAGAACAGTTGACTTTAGAAACCACTGAGCCCTTGGAAGTGGCCGATA
ACGCTCTAAAACTGAAACTTGGAAAAGGCTTAACTGTTAGTAATAATGCTTTAACCTTAA
ACCTTGGAAACGGTTTGACTTTCCAACAAGGTCTTTTACAAATTAAAACTAATAGCTCTG
TAGGGTTTAATGCTTCTGGGGAATTATCAACAGCTACAAAGCAGGGAACCATAACCGTTA
ACTTTCTAAGCACAACTCCTATAGCTTTTGGGTGGCAAATAATACCTACTACTGTAGCTT
TCATTTATATTTTATCAGGAACACAATTTACTCCTCAATCCCCAGTAACTTCTTTAGGTT
TTCAACCCCCACAAGACTTTTTGGATTTCTTCGTTTTAAGTCCGTTTGTTACATCTGTAA
CTCAAATTGTGGGAAATGATGTTAAGGTTATTGGCCTAACTATTTCTAAAAACCAATCTA
CCATAACTATGAAATTTACTTCTCCCTTAGCTGAAAATGTACCAGTTAGTATGTTTACAG
CACATCAATTCAGACAATGAATATTTTAAAAATTCTTTATTAAAGAGTAATCTTTTTACA
TACCGTTCTTGACATAATGTGCCTCTATAATTAACAAATCTAAGCAAGCAAGGTTGATCA
TTGGAATCTATAGAAGCATAACTCTTCCAATAAGCATAATCATATGGCGGTAAATGAAAA
CCCCTTAAATCTACCATATTCATCTTTAAGTGTACAGTATCTAACAGGTTTTTACAATCT
TGCACTTCTGGACTTTTAAAAACAAACAGTACTTTCATAGGACAACAATTGTAACGGTTA
TAATCTGTTACAATTTTACTTATTTCTTCTTCCAATGGCAAAGCATTCCAAAGTCTTGTT
ATAAGTACTGTAAAATCATCAAATGAATAACATAACACATTTGTACAACAATTGGTCCAA
GGTAAAAAAACAGGCACACGAACATGAACTTTTTTTAAAATTAACATCAGTGTCTGTTTT
AAACTTTGACATTGCAAAGAATTTGGCTGCAAGCAATGACAATGAAATTGATTTTGCTGA
CAAGGTAAGTCACACAAATACAACTTTAACAGCCTAAATATAACAACATTAATGTAACTT
TCCAAGACTTTAAAACTAACAAACGGTATATCACAATAAAAAGATGATGAATCCCTTCG
CAACACATAATGGAGTTCATGCTACATCCAAAGATGGTTCCGACAAACCTCTGTAAATTA
AAGAACAACAATACAACATACGAAGAAAATTAAAACGTTTTTCAAAACGAGATATACATT
GCTGCAAAGTATCTGAACATTTACATTTTATACTTATAAGCTCACAAGTTTCAGAAAATG
TAATTCGTTTAACAGTTTGATATGAATACCATTTTGAAGAAAAT
CATCTTCCATCACTCCAGAAAATAAAAAAT
AGAAATGAGTTTTGTG
CATTTGTGAAGCTCCCAGAAACATTAACGGACAXGCAAATCCAAGTATTACAACAAACACG
AACAGTCTTAACGTTTCGTTCAGAAAACAAAGTAACAGGCATATGATTAAAGCAAGACAA
TAAAACACTTTTGGCAGCTAAACATTGCAAAGATCCAGGTGAATTACAATGACAATGATA
ATAAAACTTATAAGCCATATCGGCCCTCTTGCAAAACGAATCAGCTTTTTGGCTTATAGG
AAAATAACAAAAAAACTGATTATATATGAATGGAGTTAATATCTTCTTCAAATTATACAC
ACGAATAGCAGAACCAAGACGACCACGCCCAACACAGGTAAATATTTCAAGTCCATGACT
AGGAACAGATGGTTTCTCACAAGCAACAACTTTGATTTGCTTATCCATCACTGCCAATCA
GGCTTAATAGGAAAAGAAGAAAAATAATTTTCCAATAATAACGAAAGAAATTCCACGTT
TCATCCTGTACATTACTAGTCACAAATACAACCTCCGCTATCAAAGATTCCCTATCATTT
AAAACTCCCACCAAATTGTCCAGTCTACCTCAAAAAAGCCAGTTCCATATTTTCAAAA
TTTGCCCATTTTAAATAATCCAAAGCATCAAATTCAGGAAACAAATCTTTCTGAGCTAAA
ACATATACAGTTTTATCGCCATTAAATCTAAAGCCATCCTAAATGGACCTCTAGCCCAG
TAGTTTAAGTACCGGGAAGAGACTATACAATATACTTGATATTGATGTCTGTTAAGTGGT
GATAAAAAAGAAAGTAATTCAGAATTAGGATAAAGCATTCTCCCATGTTGATTCATCTAC
AAAAAACAAAAAAATTATAAGGTTCATAGAAAACCTACTATTTAACAAATCTATAAAAAT
GCATTAAAAAGTTACCTTGAATATAAATTCAGATCACCTAAAAAACGAAAAAAAATAACA
TTTATGTTAGTAAATGATAGTCTTTAAAAATTAGAAAAGAATCAAGTCGCTTTTATACTT
ACAAACTCCAAATAAATTCTGTAACCAAGAGAAAAATTGTAACCTAAAAGGTAAAGAAGA
```

FIG. 13(A-7)

```
ACATTATAAGATTAAAACCACTCTAAAATCTGAAAAGCATTATGAAAAATTCTGATAGCT
GCAACTTACTAGTCTTCTCCAAATGTTGCAGGCATTTCAAAAAATCAAGAGGAAAACCGG
AGTTTATAAAGTAGTAGTCTGATTATATCTGAAAAAGTTTAACTTCCTTTTCAACCCAAC
CCAGTCCAATAAAAATTCCAACCTTAACTTCTTTCCTGCTAAAACTCCATAAAAGTCCAAT
TACCACTTGACTTTTATTTAACCTCAATTATGTTACATGTTATTCTACCCATAAAAACTT
GATGACCAAGAACTGACCTTTCCCATGTTTTCTGAAATAACAAAAATGTTGATTTAAAG
ATTTTTAACTACCCAAAAAAACCCGCTCTCATGATTTTTTCTTATATAAACAGGATACAAA
AGAACTGGCAAAGATATTCCATCATACTTCTCCAACTGTCAAAACATACCACTTAACCTC
TCCCATGTTTTTTCCCTTTTGCACAAACAGGATATAAAAAATATTTTTGCCACAATGTTT
TTCCTTTTACTCAACTGCCAGAATAAAAATGAACAGCTTAACCTTTTTCCCTCTTAACCC
ATTGCGTTCCTCTAAGAAAAAAATTATCCCGCCCAATATGCTAAAGGCTTCTCCCGCCAA
AACAGCTCAACTTAAAATCTCTCATGAATAAAACCCAGAGAAAATTTCCAGTAATAAAAA
TTAATAACCGTGAAGTACTAGATCTAATAATGATATTTTGAACTCATAAAAATCCACCAT
CCATGTAATGTTACAAACACTTTTTTATTGAGTTTTTTCTTACAACTGCATTACATACAG
GCCAAGCATCAAACTTTCTTCTGTATTTCTTCCTAGACCACAAAATTACAGACTTATATT
TCTGCCACAAATCTCTATGATCTTTACAGTAACACTTACATTTAAATGGGGAATACAGCA
GCAAATAAGGATGAGTTAAACATGCGATACAATGACCAGAAGGAAGATAATACAATACAT
CACACCAAAATGAAGGTACAGACAACATCGCATGAAATCTTAAATGTGATTTTACAATAA
ATTTCTGCAGCAGCTTACAATCTATATTAGCAAACCGTTTTATATACAAACATAAAAACT
TGGAACTTTTCACCAACTCAATCATGTTATTATAACACATTACAAATTTTGCTATATCTT
TATTTGTCAAATAACAAAATATCTCAATCCACAGCTCATCTGGCAGCAAACTTCGCAAAT
CCATGACCTGTAAAAGATACAACAGAAAACAGAAAATTAATGCCATTCAATAACATAAAA
AATACAGTCAAATCACATACTTTTTCTCACTTACAAAACTTTGTGAGCAGGCCTCCAAAA
CAAACTTCAGAAAATGGATGCATACAAGAACATTCTCCTCTCAAAAAATTGCTTTAACTGA
ATGCGGCATTTTGCACCTCCAGAAAAATGCAGTCCATTGAGAGGCTCTTCTCTTAAAACA
CAGAAATGCTTCTGCAAAATCTGTAAAGAAACTAACAACTTCCAAATTCCAATCATCATG
CATTGCAAAGAAGGACATTCAACAGCAAAGGATCGTGATGAGCCAATAAAGCTTTACTG
TATGACTCATTTTCATGAATTACAGTCTGTAACTTACTATAATGCATTTTAAGCTCTGCT
TCACAAATTAATAATGCTAATTTCTTTAAGCAGCTCAAAGAAAACTCATCAGGACAACGG
CATTTAAGAAAGCAACAAAATGATTTCTTAAAATACATTTTTCCAGCATGATGAACAATA
AAAAATTTCAACGTTAAACAATGCAAAAATGCATTTTTATGCACAGTGAAAGTAATTTTT
TCAGCTGAAGCTAAATCACAGCCTATTTTATTACATGATTTTGTATGCTCCAAAAGAGCT
TGTTTTAATTGCTTCAAATCCATCTTCTTACATTTTTTCTTTTTATAAACACCAGAACC
GCATTCAGGCCAATTCCAGTTATTGTTTAAATTTGCTACAGAAACTGCAGACCACAAAAC
CACATCCTCTAAATCAACCCACAAAGATCTATGATCCACACAAAAACACAAAGAATGATA
CGGAGAATACAACAATAAATGGGGATTAACAAGGGACGCAACACAATGACCCGAAGGTAA
TAAAGTTTTACAGCACCAATTACAAGCAACAGGTAATGGAGTATATTTCCCAATGCGACG
AGAAAGCCGAATGTCATTCAGAACAGCATTGCATTTTATCTTCTCAAACCTCTTAAGGTG
CAATTGTATAAAATAAGAATCCTTAATGACAGTGATGAATTGAGGAAAAGCAAAACAAA
ACTAGCAATGTCTTTGCTTGTAAGTTTCAAAAATATCTTCATCCAAATCTCAGTCGGTAA
TTCAACAAAAATTCAGGCGCCTACAAAATTAATCAGACTAATTTAATATCATCTTGTAA
ACAGCGAAAAGAAAAATAACACACCCAAAATAAAAAACTCTTACCCCTGTTATCCATC
GAGATACACAGAAAATTCAGAACACTCAGTGTCATGTTTCTTAAATTGTTCCCAAAGCT
CAGACATTCTAAGCCAAAATTTTTGAGAACTGCAAAAACCCAGTTTTTATAACAAAGC
CTTAATGTTTTCTTAACTGATTTAACTGCCCTAACAGGAACTCCACATTCCGGCCACCGC
CACCCAGGGGACAAATCTTGCCAAGAACTACAAGTCCATAAAACAACATCCTGCAAATTA
TACCAAAGGTTTCTATGGTCGACACAATTACAACCTGACCTAAAAGGTGAATAAAGCAGT
AAATAAGGATGAGTTAAACAGGCCACACAATGTCCAGAATGTAAAAAATGCTTTGTTTGG
CACCAACCAGACCACAGCTGAAGCAAAGGAAAATTGTAGCGAACACATTCTTCTCGTAAT
CTGTTTAACACAGAACAACATTCAATTCTGGCAAACCTCTTTAAAAAATGTTTTCTGAAA
TATTTCTTTAAAATGACAGTTTGCAACTCTGGAAAACACAAAATAAAAGCCGCAATATCT
CTACTGCTTAAATATAAAAATATCATTGTCCAAATTTCTACTGGTAAAACTGAAAGCATC
TTCTTCCTATTAAAAAAAGAAAAGTGTTTTCAAATTATATTAGACTCTAACCAAAAAAAT
TCAAATACTTTTCCTTTATAATGTACATTAAGAATAAAAATATACTCACCGTTTAAAAGT
AGAACTTAACAGTATAATATAAATACAAGTGAGCTGAACAACGACAGCCGATTTCAGCCG
GAGCAAAATTAAAAAGAATAAAAGGATCAAACCAACACGTAGGACAGTCTACTCCAAAAC
AGTAACGGCAGTATGACACAGAAGGAGAGGAACTAAGTCCAGGAAACTTCGCCCGGTGCG
ATAAAAAGTAACGCCGCCGGAAAGCAGTTGAATACAAAAGAGGTAAAAATTCACGAAAAA
CAGAAGCAAAAACTACTAAATCTGCTATTGGCAAATAAAGAAAAATTTCAAACCATATTT
CCAAAGGAAGAAAAGCAATCATACCGTAGAAGAACCTGAAGGCGACCGCAAACGTGCTCC
CGTACCACAACGTCACACGCCACACCCACTGGGAAAACCCACACGCCCCGCCTCTGTGCA
ACGTTATATATATGAATAG
```

FIG. 13(A-8)

end OAV287/start Bluescribe sequence

```
GTACCCTTTGTTCCCTTTAGTGAGGGTTAA
TTCCGAGCTTGGCGTAATCATGGTCATAGCTGTTTCCTGTGTGAAATTGTTATCCGCTCA
CAATTCCACACAACATACGAGCCGGAAGCATAAAGTGTAAAGCCTGGGGTGCCTAATGAG
TGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGC
GCTCTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTCAGA
GGTGGCGAAACCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTGTAGGTCGTTC
GCTCCAAGCTGGGCTGTGTGCACGAACCCCCGTTCAGCCCGACCGCTGCGCCTTATCCG
GTAACTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGATC
CTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCA
GTGAGGCACCTATCTCAGCGATCTGTCTATTTCGTTCATCCATAGTTGCCTGACTCCCCG
TCGTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTTATGGCAGCAC
TGCATAATTCTCTTACTGTCATGCCATCCGTAAGATGCTTTTCTGTGACTGGTGAGTACT
CAACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCA
CTCGTGCACCCAACTGATCTTCAGCATCTTTTACTTTCACCAGCGTTTCTGGGTGAGCAA
AAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACATTTCCCC
GAAAAGTGCCACCTGACGTCTAAGAAACCATTATTATCATGACATTAACCTATAAAAATA
GGCGTATCACGAGGCCCTTTCGTCTCGCGCGTTTCGGTGATGACGGTGAAAACCTCTGAC
ACATGCAGCTCCCGGAGACGGTCACAGCTTGTCTGTAAGCGGATGCCGGGAGCAGACAAG
CCCGTCAGGGCGCGTCAGCGGGTGTTGGCGGGTGTCGGGGCTGGCTTAACTATGCGGCAT
CAGAGCAGATTGTACTGAGAGTGCACCATATGCGGTGTGAAATACCGCACAGATGCGTAA
GGAGAAAATACCGCATCAGGAAATTGTAAACGTTAATATTTTGTTAAAATTCGCGTTAAA
TTTTTGTTAAATCAGCTCATTTTTTAACCAATAGGCCGAAATCGGCAAAATCCCTTATAA
ATCAAAAGAATAGACCGAGATAGGGTTGAGTGTTGTTCCAGTTTGGAACAAGAGTCCACT
ATTAAAGAACGTGGACTCCAACGTCAAAGGGCGAAAAACCGTCTATCAGGGCGATGGCCC
ACTACGTGAACCATCACCCTAATCAAGTTTTTTGGGGTCGAGGTGCCGTAAAGCACTAAA
TCGGAACCCTAAAGGGAGCCCCCGATTTAGAGCTTGACGGGGAAAGCCGGCGAACGTGGC
GAGAAAGGAAGGGAAGAAAGCGAAAGGAGCGGGCGCTAGGGCGCTGGCAAGTGTAGCGGT
CACGCTGCGCGTAACCACCACACCCGCCGCGCTTAATGCGCCGCTACAGGGCGCGTCGCG
CCATTCGCCATTCAGGCTGCGCAACTGTTGGGAAGGGCGATCGGTGCGGGCCTCTTCGCT
ATTACGCCAGCTGGCGAAAGGGGGATGTGCTGCAAGGCGATTAAGTTGGGTAACGCCAGG
GTTTTCCCAGTCACGACGTTGTAAAACGACGGCCAGTGAATTGTAATACGACTCACTATA
GGGCGAATTCGAGCTCGGTAC'    end of Bluescribe sequences
                KpnI site with 5' base
```

DNA ENCODING OVINE ADENOVIRUS (OAV287) AND ITS USE AS A VIRAL VECTOR

This application is a Continuation-In-Part Application of Ser. No. 08/776,274, filed Jan. 24, 1997, (abandoned) as the National Phase of PCT Application No. PCT/AU95/00453, filed Jul. 26, 1995 and claiming priority to Australian Application No. PM7101, filed Jul. 26, 1994.

TECHNICAL FIELD

The present invention relates to a new full length genomic clone derived from a benign adenovirus (OAV287) isolated from sheep in Australia. The present invention also relates to new viral vectors derived from the benign ovine adenovirus and also relates to the use of these vectors for the delivery and expression of nucleic acid sequences encoding functional RNA molecules or polypeptides to animals.

BACKGROUND OF THE INVENTION

Diseases caused by infectious agents and parasite infestations cause health problems and production losses in domestic animals but for many infectious agents no vaccine exists. Consequently, there are major research efforts worldwide to develop new vaccines which can protect against disease.

While some protective antigens from infectious agents and parasites have been identified, their successful use as vaccines requires the development of systems which can effectively deliver the antigen to the host. A variety of recombinant gene expression vectors derived principally from the pox virus family have been employed as these are generally of low pathogenicity. Expression of the foreign protein following infection by the recombinant viral vector may stimulate a protective immune response in the host.

However, no viral vector has all the attributes desirable for all situations. Some vectors are better suited to particular tasks than others because of their biological properties. For example, it has often proved difficult to stimulate an effective mucosal immune response which can protect against disease. In humans, adenoviruses have been given orally to vaccinate against respiratory disease (1). As this involves protection at mucosal surfaces adenoviruses clearly have potential in this regard. Human adenovirus vectors have also been used to deliver genes to muscle (2) and other tissues. Although adenoviruses do not generally integrate their DNA into the cellular genome, nevertheless, the DNA persists and long term protein expression is observed. Expression of an appropriate antigen from such cells can generate a systemic immune response which may be protective against the homologous disease causing agent.

Known adenovirus genomes are linear double-stranded DNA molecules which have an inverted terminal repeat sequence (ITR) at each end and a protein covalently bound to the 5'-terminal C residue (3). The genome sequence and structure has now been completely determined for human adenoviruses types 2, 5, 12 and 40 and partially for numerous others, including some animal isolates (see Genebank and EMBL Nucleic Acid databases). Human adenovirus type 2 was the first genome to be sequenced but broadly speaking its genome arrangement is conserved among other characterized adenoviruses i.e. early regions E1–E4 and the structural protein homologues can be recognized in similar locations in the genome. In particular, the E1A/E1B region is located at the left hand end of the genome and region E4 is always located at the right hand end of the genome. Early region E3 is always located between the genes for structural proteins pVIII and fiber, although its size and complexity varies between species e.g. from 3 kb with at least 10 open reading frames in human adenoviruses to approximately 0.7 kb with only two significant open reading frames in murine adenovirus (4, 5). E3 is a key region for the construction of recombinant viruses as it is non-essential for replication in vitro (6). The late, L region is expressed from the major late promoter, MLP and complex splicing generates families of mRNAs which code for most of the structural viral proteins. Proteins IVa2 and IX appear to have their own promoters.

Although there are some human viral vectors available for medical use there are few animal viral vectors suitable for use in veterinary applications. In order to obtain a more suitable animal viral vector the present inventors have purified an ovine adenovirus (OAV287) isolated from sheep in Western Australia. This ovine adenovirus is serologically related to bovine adenovirus type 7 but is genetically distinct from the bovine adenoviruses and other Australian ovine isolates, as shown by comparisons between the ovine and bovine adenoviruses, based on restriction enzyme profiles (8). The genome arrangement of the virus according to the present invention varies significantly from all other known adenoviruses. The adenoviral DNA molecule of the present invention is suitable for use in viral vectors capable of expressing a variety of polypeptides when used for veterinary applications.

SUMMARY OF THE INVENTION

According to a first aspect, the present invention consists in an isolated DNA molecule comprising a nucleic acid sequence encoding the genome of ovine adenovirus (OAV287) substantially as shown in FIG. 1 (SEQ ID NO:1) or a functionally equivalent nucleic acid sequence. Preferably, the nucleic acid sequence encoding the genome of the adenovirus is substantially as shown in FIG. 1.

In a further preferred embodiment of the first aspect of the present invention, the DNA molecule comprises a nucleic acid sequence encoding the genome of ovine adenovirus (OAV287) wherein a portion of the adenoviral genome not essential for the maintenance or viability of the native adenovirus deleted or altered.

In a second aspect, the present invention consists in a DNA molecule including at least a fifteen nucleic acid base sequence being substantially unique to the ovine adenovirus (OAV287) nucleic acid sequence shown in FIG. 1. In a preferred embodiment of the second aspect of the present invention, the at least fifteen nucleic acid base sequence encodes a functional element of ovine adenovirus (OAV287). Preferably, the functional element is selected from the group consisting of promoter, gene, inverted terminal repeat, viral packaging signal and RNA processing signal. The inverted terminal repeat of ovine adenovirus (OAV287) comprises the first 46 nucleic acid bases from the 5' end of each strand of the double stranded DNA genome of the virus.

In a third aspect, the present invention consists in a plasmid including the DNA molecule of the first or second aspects of the present invention. Preferably, the plasmid includes the DNA molecule of the first aspect of the present invention wherein the nucleic acid sequence encoding the adenoviral genome is linked to a nucleic acid sequence encoding an origin of replication and a further nucleic acid encoding a marker. Preferably, the nucleic acid sequence encoding the marker encodes for resistance to an antimicrobial agent. More preferably the antimicrobial agent is ampicillin.

In a further preferred embodiment of the third aspect of the present invention, sequences encoding inverted terminal repeats of the adenovirus are joined.

In a fourth aspect, the present invention consists in a viral vector comprising the DNA molecule of the first aspect of the present invention and at least one nucleic acid sequence encoding a non-adenoviral polypeptide or polypeptides.

Preferably, nucleic acid sequence encoding the non-adenoviral polypeptide or polypeptides is derived from bacteria, viruses, parasites or eukaryotes. More preferably, the non-adenoviral polypeptide is rotavirus VP7sc antigen, the parasite polypeptide is *Trichostrongylus colubriformis* 17 kD antigen, the *Taenia ovis* 45 W antigen or the PM95 antigen from *Lucilia cuprina*.

In another form, the present invention consists in a viral vector comprising the DNA molecule of the first aspect of the present invention and at least one nucleic acid sequence encoding a functional RNA molecule. It will be appreciated by one skilled in the art that a functional RNA molecule can include a messenger RNA molecule, an antisense RNA molecule or a ribozyme.

In a fifth aspect, the present invention consists in a method of delivering a DNA molecule having a nucleic acid sequence encoding a non-adenoviral polypeptide or polypeptides to a target cell comprising infecting the target cell with a viral vector according to the fourth aspect of the present invention such that the DNA molecule encoding the polypeptide or polypeptides is expressed and the polypeptide or polypeptides is produced by the target cell.

In a sixth aspect, the present invention consists in a method for delivering a DNA molecule having a nucleic acid sequence encoding a non-adenoviral polypeptide or polypeptides to an animal comprising administering to the animal a viral vector according to the fourth aspect of the present invention such that the viral vector infects at least one cell of the animal and the infected cell expresses the DNA molecule encoding the polypeptide or polypeptides and produces the polypeptide or polypeptides. Preferably the animal is a grazing animal and more preferably the grazing animal is a sheep.

In another form, the present invention consists in a method for delivering a DNA molecule having a nucleic acid sequence encoding a functional RNA molecule to an animal comprising administering to the animal a viral vector of the fourth aspect of the present invention having a nucleic acid sequence encoding a functional RNA molecule such that the viral vector infects at least one cell of the animal and the infected cell expresses the DNA molecule encoding the functional RNA molecule and produces the functional RNA molecule.

As used herein the term "functionally equivalent nucleic acid sequence" is intended to cover minor variations in the ovine adenovirus (OAV287) DNA molecule which, due to degeneracy in the DNA code, does not result in the molecule encoding different viral polypeptides. Further, this term is intended to cover alterations in the DNA code which lead to changes in the encoded polypeptides, but in which such changes do not substantially affect the biological activities of these viral polypeptides.

As used herein the term "functional element" is intended to cover nucleic acid sequences that encode promoters, genes, inverted terminal repeats, viral packaging signals and RNA processing signals. It will be appreciated by one skilled in the art that unique sequences from ovine adenovirus (OAV287) that encode these functional elements may be useful in other systems including plasmids and non-ovine adenoviral vectors.

In order that the nature of the present invention may be more clearly understood preferred forms thereof will be described with reference to the following examples and the accompanying drawings.

BRIEF DESCRIPTION OF THE DRAWINGS

FIG. 1 is the nucleic acid sequence of the OAV287 genome beginning at base 1 of the left-hand ITR (SEQ ID NO:1).

FIG. 10 shows a summary of recombinant viruses which have been rescued from the corresponding infectious plasmids and the gene expression cassettes they carry. Cassettes were inserted into the OAV genome between the pVIII and fibre genes as indicated.

FIG. 13 is the nucleotide sequence of a plasmid containing a modified OAV287 genome which begins at base 1 of the left hand ITR and continues through to the end of the OAV287 sequence (29,574). (SEQ ID NO. 3). The positions of changes in the sequence (in comparison to the sequence illustrated in FIG. 1) are indicated by bold letters offset in larger font than the surrounding letters; actual nucleotide additions to the sequence are indicated by a letter representing a nucleotide (A,G,C or T) and the deletion of a nucleotide from the corresponding sequence set forth in FIG. 1 is indicated by an X (in bold and of larger font). Nucleotides 1–29,574 represent OAV87 sequence; nucleotides 29,575–32,7454 represent Bluescribe plasmid sequence

DESCRIPTION OF THE INVENTION

Methods

Growth and Purification of OAV287

Figure 2:
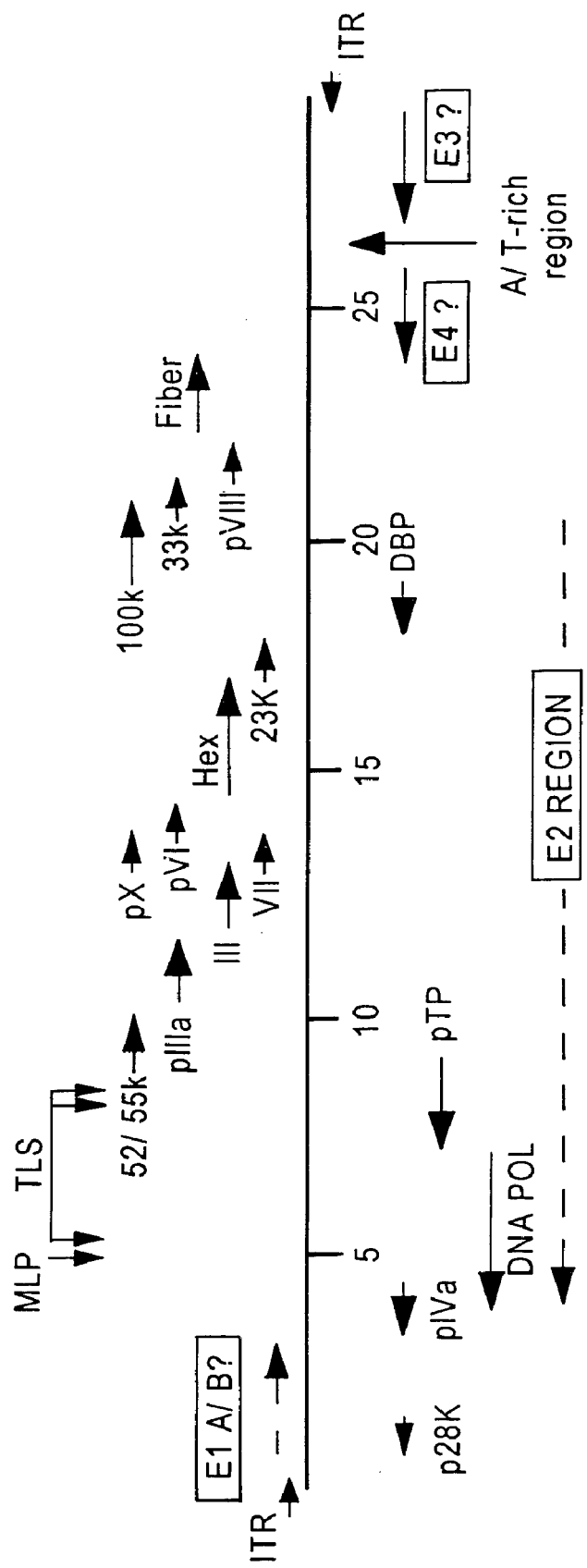
FIG. 2 shows the arrangement of OAV287 genes based on homologies detected with Ad2. Regions with question marks are tentative identifications because of the lack of obvious homology.

The virus, isolated from sheep in 1985, was obtained from R. L. Peet, Animal Health Laboratory, Department of Agriculture, Western Australia. The virus isolate was grown in sheep foetal lung cells (line CSL503) and twice plaque-purified under solid overlay before stocks were prepared. Virus was purified from CSL503 cells as described previously (18, 22). DNA was extracted from the virus by digestion with proteinase K (23).

Cloning of Genome Fragments

Molecular techniques for manipulation, modification and transformation of plasmid DNA which were used in the work described below are described in (9) and similar publications. OAV287 DNA was digested with various restriction endonucleases including BamHI, SphI, SmaI and SalI to deduce the location of these sites (18).

The adenovirus genome has a protein covalently linked to each end of the linear dsDNA (24). The BamHI A and D fragments of approximately 8 kb and 4 kb, respectively, were identified as the terminal genomic fragments because their migration into agarose gels was dependent on the pre-digestion of viral DNA with proteinase K. The internal BamHI fragments B, C, E and F, estimated at 6.2, 5.1, 3.4 and 1.1 kb in size respectively, were separated on an agarose gel, recovered and cloned into BamHI-digested pUC13 using standard ligation and transformation procedures (9). To clone the terminal BamHI A and D fragments, viral DNA (10 μg) was digested with proteinase K (50 μg/ml in 10 mM Tris/HCL, pH8.0, containing 1 mM EDTA and 0.5% SDS) at 65° C. for 60 min to remove the terminal protein. The DNA was extracted twice with phenol/chloroform, once with ether and recovered by ethanol precipitation. The 3'ends (of unknown sequence) were then digested exonucleolytically with $T_4$ DNA polymerase (5 units, Toyobo, Tokyo, Japan) in the presence of dATP (100 μM) in buffer containing Tris HCL (50 mM), pH8.0, $MgCl_2$ (7 mM), 2-mercaptoethanol (7 mM) and BSA (10 μg/ml) for 15 min at 37° C. The DNA was again purified by phenol extraction and ethanol precipitation described above. To remove the single-stranded terminal regions and create blunt ends the DNA was digested with 1 unit of mung bean nuclease (Pharmacia, North Ryde, Australia) for 10 min at 37° C. in buffer containing Na acetate (30 mM), pH4.6, NaCl (50 mM) and $ZnCl_2$ (1 mM) before extraction with phenol/chloroform and recovery by ethanol precipitation. Finally the DNA was digested with BamHI (Pharmacia) and the fragments were separated by electrophoresis in low-melting-point agarose. The BamHI A and D fragments were excised, recovered by NACS column chromatography (BRL, Gaithersburg, Md) and ligated with BamHI/HincII-cut plasmid Bluescribe M13+ (Stratagene, La Jolla, Calif.) prior to transformation into *E. coli* JM109. Positive clones carrying fragments of the expected size were identified, restriction digested and confirmed as correct by nucleotide sequencing and comparison with partial sequence determined directly from genomic DNA. This revealed that three 3'-terminal nucleotides were removed during the cloning procedure.

When used herein "high stringency" refers to conditions that:

(i) employ low ionic strength and high temperature for washing after hybridization, for example, 0.1×SSC and 0.1% (w/v) SDS at 50° C.; and (ii) employ during hybridization conditions such that the hybridization temperature is 25° C. lower than the duplex melting temperature of the hybridizing polynucleotides, for example 1.5×SSPE, 10% (w/v) polyethylene glycol 6000 (Amasino, 1986), 7% (w/v) SDS (Church, 1984), 0.25 mg/ml fragmented herring sperm DNA at 65° C.; or for example, 0.5 M sodium phosphate, pH 7.2. 5 mM EDTA, 7% (w/v) SDS (Church, 1984) and 0.5% (w/v) BLOTTO (Johnson, 1984; Reed, 1985) at 70° C.; or (iv) (iii) employ during hybridization a denaturing agent such as formamide (Casey, 1977), for example, 50% (w/v) formamide with 5×SSC, 50 mM sodium phosphate (pH 6.5) and 5×Denhardt's solution (Denhardt, 1996) at 42° C.; or employ, for example, 50% (w/v) formamide, 5×SSC, 50 mM sodium phosphate (pH6.8), 0.1% (w/v) sodium pyrophosphate, 5×SSC Denhardt's solution (Denhardt, 1996), sonicated salmon sperm DNA (50 μg/ml) and 10% dextran sulphate (WahL, 1979) at 42° C. See generally references Meinkoth, 1984; Reed, 1991; Dyson, 1991.

Nucleotide Sequencing of the OAV287 Genome

The complete sequence of the OAV287 genome was determined by sequencing the BamHI fragments A–F using the Sanger method (25) and various kits provided by commercial suppliers. Nested deletions were constructed for the five largest fragments using a double-stranded nested deletion kit (Pharmacia). These were sequenced using standard primers. Based on newly determined sequence other nucleotide primers were synthesised using a DNA synthesizer (AB1, Model 391). In this way both strands of the entire genome and the junctions between the fragments were sequenced.

Mutagenesis of the OAV287 Genome

For the construction of a full length OAV287 clone and subsequent modification of it to create plasmids such as pOAV200 and pOAV600 certain mutations were required. A relevant portion of the genome was subcloned into Bluescribe (Stratagene, La Jolla, Calif.) or a similar plasmid which allowed rescue of single stranded DNA. Later it became possible to use dsDNA for mutagenesis. Oligonucleotides of the desired sequence were synthesized, phosphorylated and used as primers as described by the manufacturers of Muta-gene Phagemid (Biorad Labs, Calif.) or Altered sites II (Promega, Wis.) mutagenesis kits. Mutations were generally identified by digestion with the appropriate restriction enzyme or by nucleotide sequencing, or both. Genome fragments containing introduced mutations were subcloned to create larger plasmids such as pOAV200 using appropriate unique restriction sites.

Construction of a Full-Length Genomic Clone of OAV287

The terminal BamHI A and D fragments (cloned in Bluescribe M13$^+$) were each modified by mutagenesis to add the nucleotides lost during cloning and a KpnI site. The last base of the KpnI site incorporated the C at the 5' end of each genomic ITR sequence. This produced plasmids pAK and pDK (FIG. 6).

The left hand approximately 21.5 kb of the genome was constructed from the BamHI D and B fragments and the SphI A fragment of approximately 13 kb. The genomic BamHI B fragment cloned in pUC13 was modified by mutagenesis (GCATGC to GCATCC) to remove the SphI site at position 8287 producing pUC13B. The modified fragment was released by BamHI digestion and cloned into pDK which had been cut with BamHI and dephosphorylated. Colonies carrying the recombinant plasmid pDBM (FIG. 6) were identified by screening with an oligonucleotide which spanned the BamHI B/D junction. The SphI A fragment (approximately 13 kb) was cloned into the SphI site of pSELECT (Promega) to form PSESPH. This fragment contains a SmaI site near its left hand end which is common to PDBM. The KpnI/SmaI fragment from pDBM was subcloned into pSESPH which had also been cut with KpnI/SmaI to produce pSELLH, a plasmid based on pSELECT which now contained the left-hand approximately 21.5 kb of OAV287 DNA.

Figure 6:
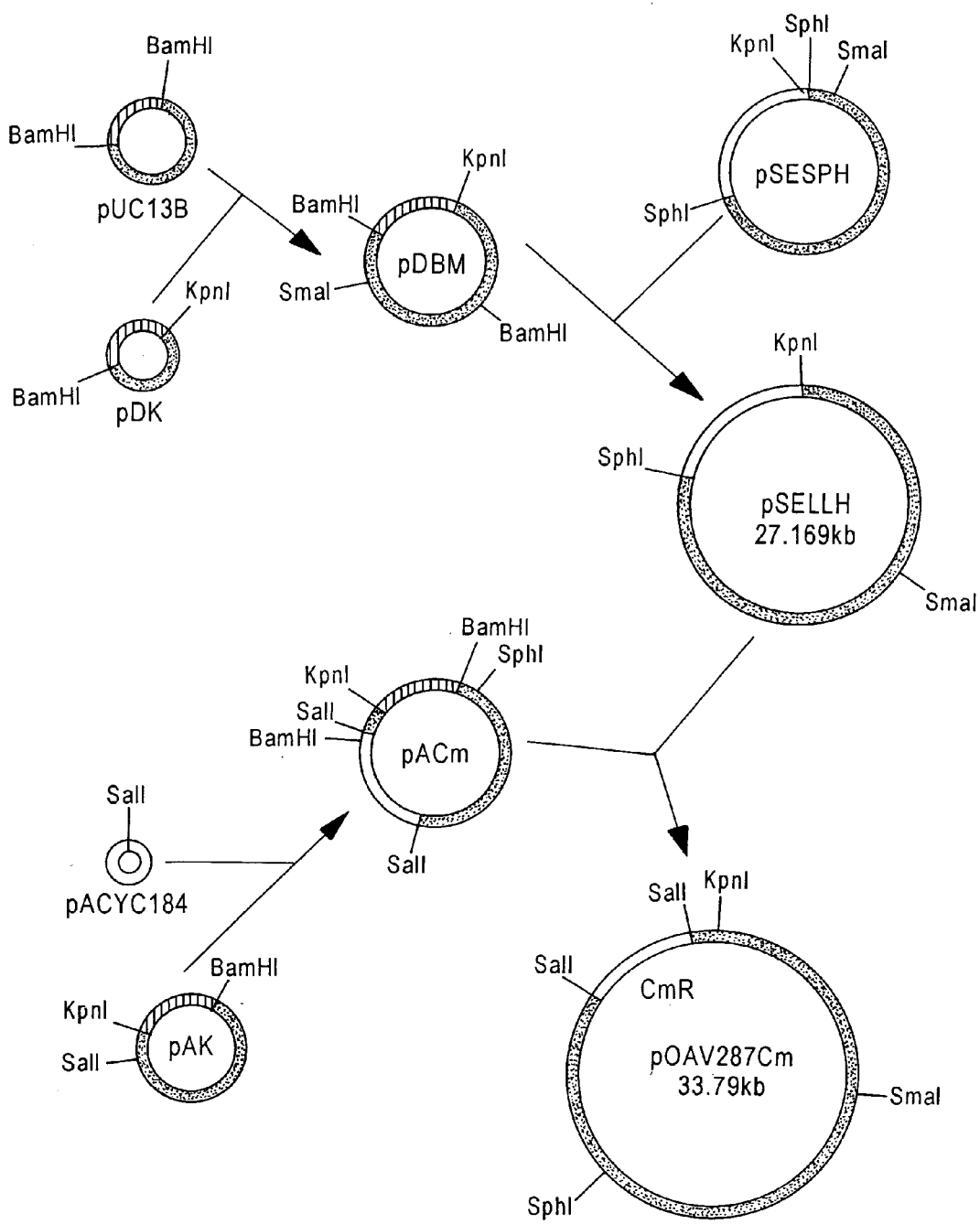
FIG. 6 is a scheme describing the construction of a plasmid (pOAV287Cm) containing a full-length clone of the OAV287 genome with pACYC184 sequences inserted in the SalI site. Filled in regions show OAV287 sequences. Cross-hatched sequences are derived from plasmids pUC13 or Bluescribe M13+ ($Amp^R$), stippled regions from pSELECT ($Tet^R$) and open regions from pACYC184($Cm^R$). Only the key restriction sites used for plasmid construction are indicated.
Figure 7:
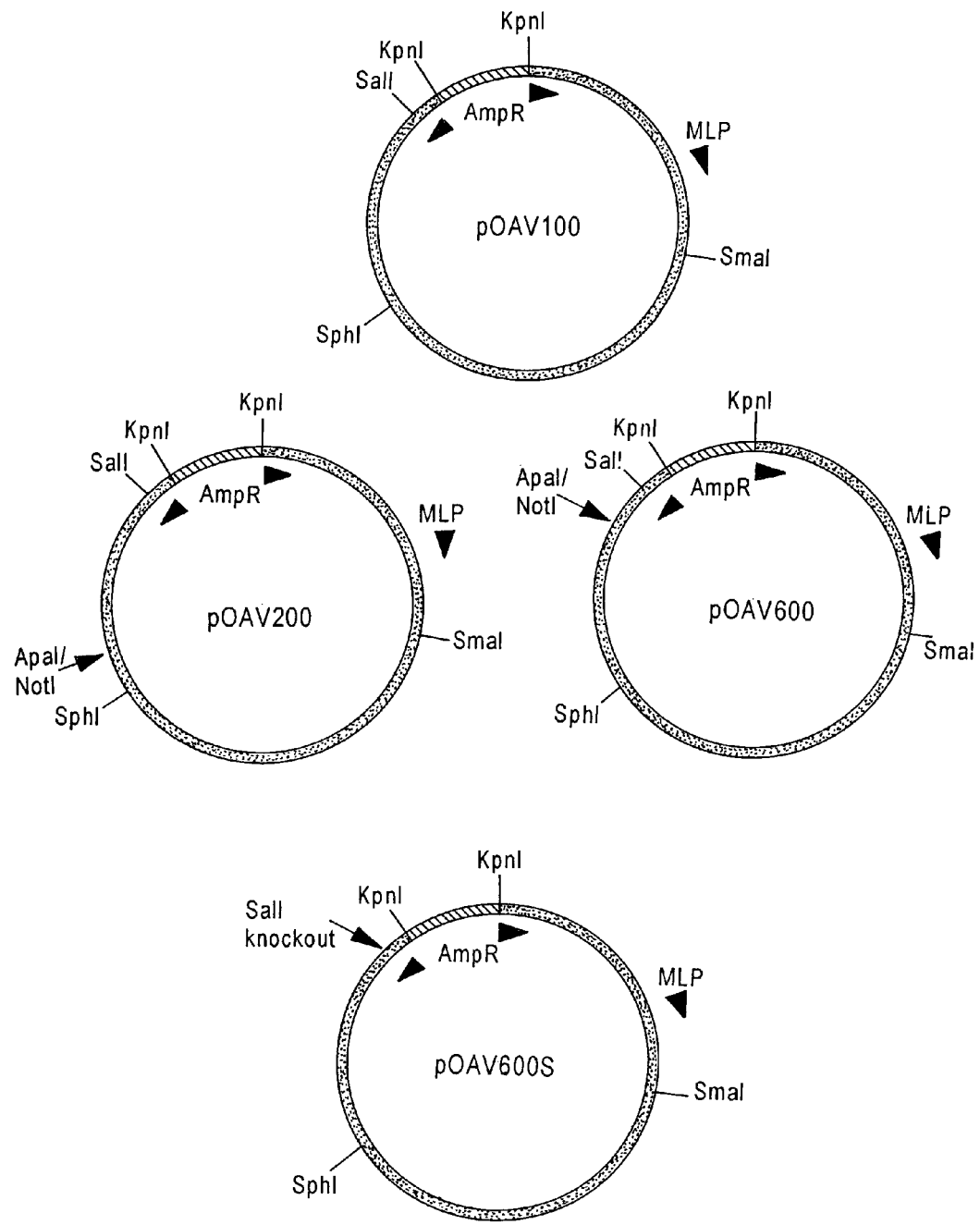
FIG. 7 shows a map of the plasmids pOAV100, pOAV200, pOAV600 and pOAV600S. Arrowheads indicate the ITRs and the approximate location of the major late promoter (MLP). The mutated SalI site and sites at which the ApaI/NotI polylinker sequences were inserted are indicated. Light hatching signifies modified Bluescribe sequences inserted in the KpnI site. Linear, infectious genomes (dark hatching) are released by digestion with KpnI.
Figure 8A:
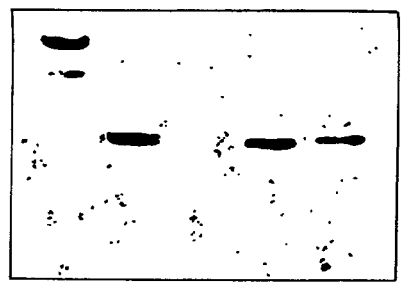
FIG. 8 shows the results of screening ovine adenoviruses OAV100 and OAV200 rescued by transfection of recombinant plasmids pOAV100 and pOAV200 into CSL503 cells. Portions of the genome spanning (A) the mutated SphI site in OAV100 and (B) the ApaI/EcoRV/NotI polylinker insertion site in OAV200 were amplified by PCR together with the corresponding regions from wild-type OAV287. The products were digested with SphI (A, lanes 3 & 5) and ApaI, EcoRV or NotI (B, lanes 3–5, and 8–10, respectively). (U) indicates undigested samples.
Figure 8B:
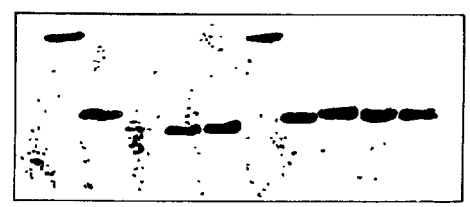

The right-hand end of the genome was constructed from pAK which contains the right-hand approximately 8.6 kb of the genome and overlaps the SphI A fragment. pAK was cut with SalI and ligated with SalI-cut pACYC184, a plasmid of 4.24 kb which contains a gene encoding chioramphenicol (Cm) resistance and an origin for DNA replication, to form a pACm (FIG. 6). This plasmid was cut with SphI and KpnI to produce the right-hand genomic fragment incorporating the pACYC184 sequences. This was ligated with the left-hand KpnI/SphI fragment of approximately 21.5 kb prepared from pSELLH to produce the final plasmid pOAV287Cm (FIG. 6). This plasmid replicates stably in *E. coli* and therefore removes the need to propagate the virus to obtain genomic DNA for further study. The recombinant genome in plasmid pOAV287Cm differs from the wild-type viral genome by the single point mutation in the SphI site (base 8287), by the presence of pACYC184 sequences in the SalI site and by the addition of a GTAC sequence between the ITRS. However, insertion of pACYC184 sequences in the SalI site disrupts two significant open reading frames whose functions. are unknown. If either of the gene products was essential for replication, then pOAV287Cm could not produce infectious virus following transfection. To circumvent this potential problem pOAV287Cm was modified further. First, plasmid Bluescribe M13—(Stratagene, La Jolla, Calif.) was cut with HindIII and end-filled. The linear plasmid was then cut with SmaI, blunt-end ligated and transformed. The resulting plasmid contained an ampicillin resistance gene and origin of replication and lacked SalI and SphI sites but retained a unique KpnI site. This plasmid was cut with KpnI and ligated with KpnI-cut pOAV287Cm. Plasmids which were doubly resistant to ampicillin and chloramphenicol were selected and grown. One of these was cut with SalI to release the pACYC184 sequences, religated and transformed. The resulting plasmid pOAV100 contained the AmpR gene and replication Ori inserted in the KpnI site between the ITR's of the genome (FIG. 7). This plasmid replicated stably in *E. coli* strain Jm109 when maintained in the presence ampicillin (200 μg/ml). Large quantities of plasmid were grown for transfection studies.

Transfection of DNA and Virus Rescue

Figure 9:
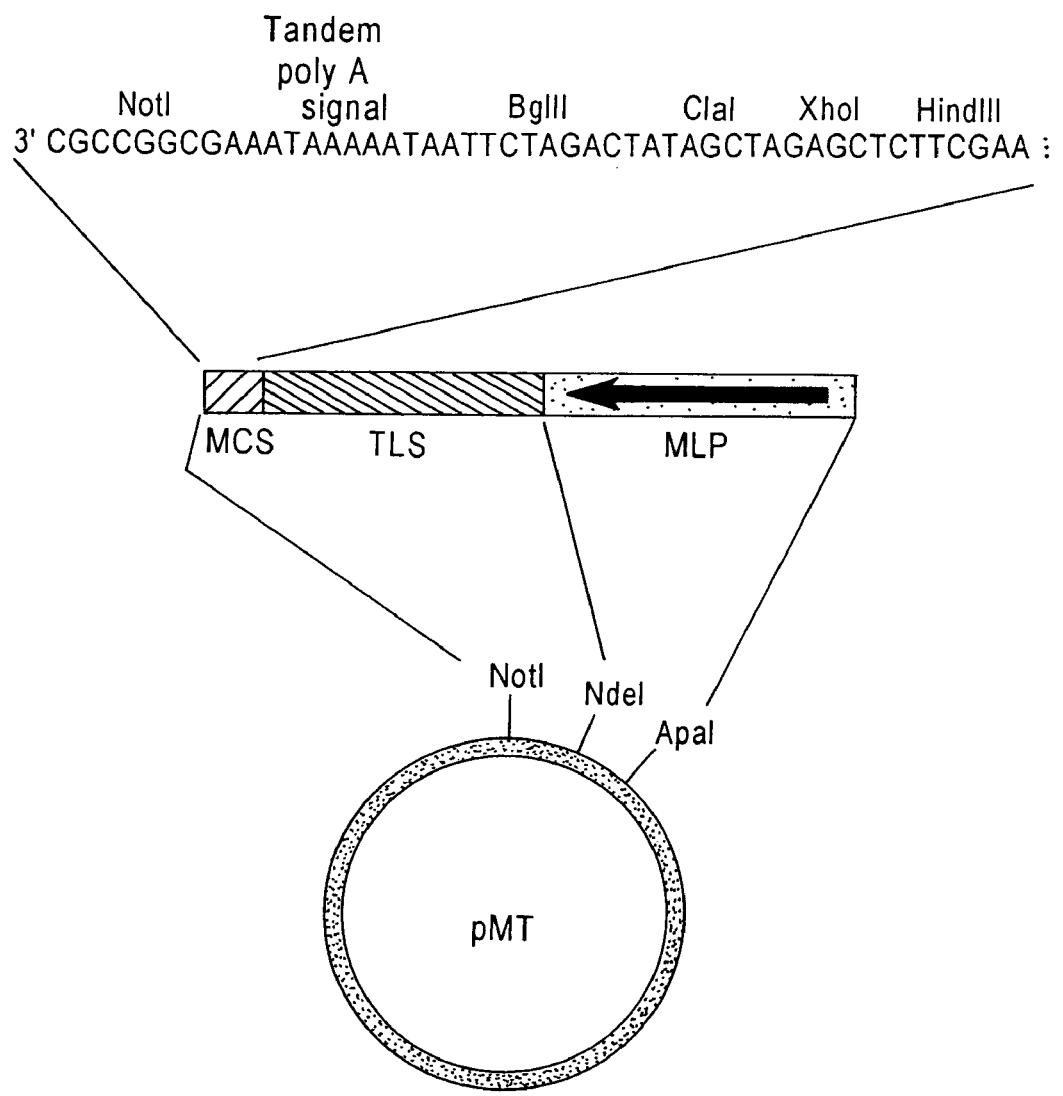
FIG. 9 is a map of a plasmid pMT used for the assembly of gene expression cassettes. Fragments containing the OAV287 major late promoter and tripartite leader sequences are linked and precede a multiple cloning site (SEQ ID NO:2) for the insertion of genes of interest. A tandem polyadenylation signal (AATAAA) follows.
Figure 11A:
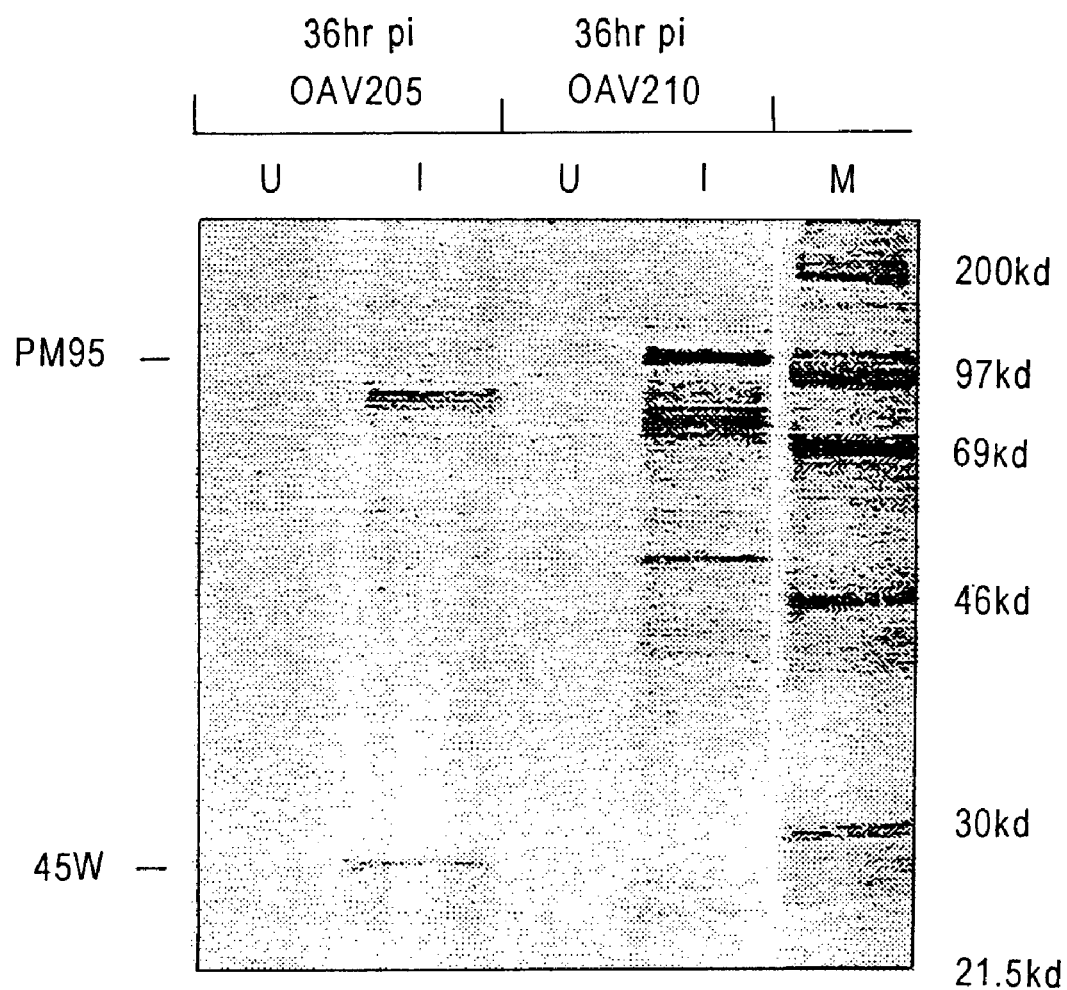
FIG. 11 shows the expression of (A) the *T. ovis* 45W and *L. cuprina* PM9S antigens in CSL503 cells following infection of these cells with OAV205 and OAV210 viruses, respectively and (B) VP7sc expression in CSL503 and bovine nasal turbinate cells following infection with virus OAV204. (I) Infected cells (U) Uninfected cells. (M) indicates marker proteins of the sizes shown.
Figure 11B:
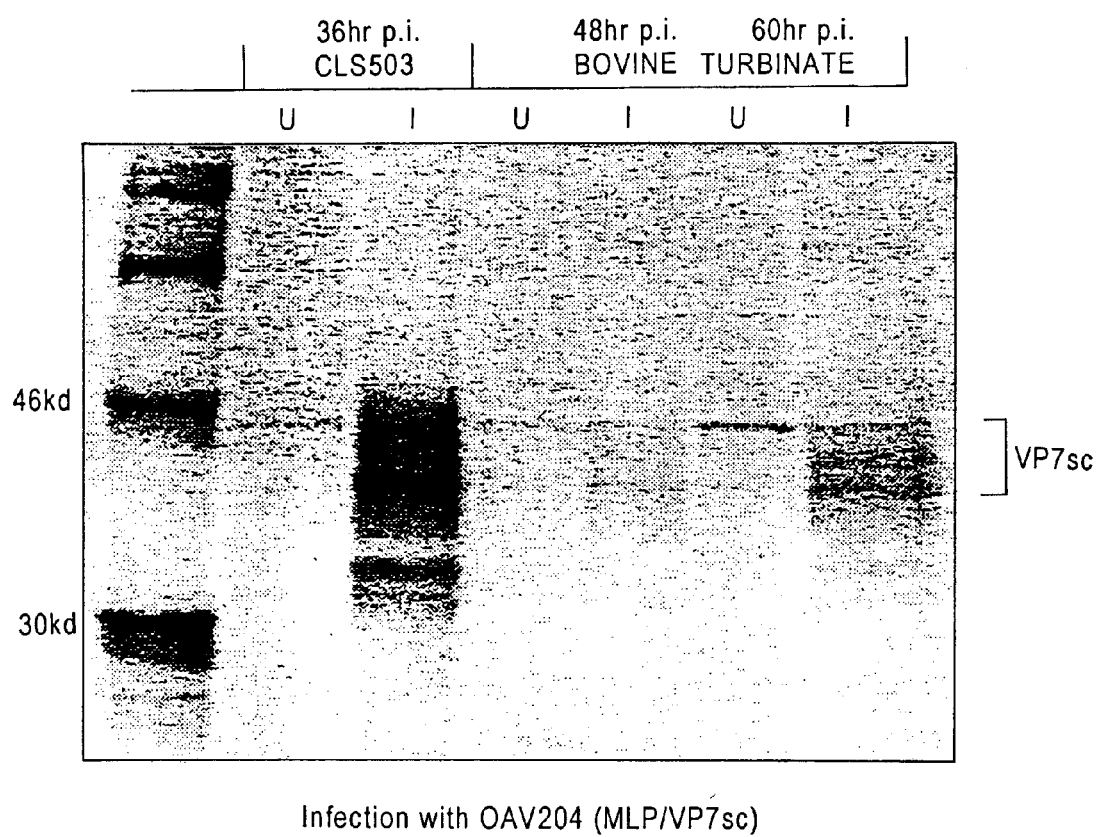
Figure 12A:
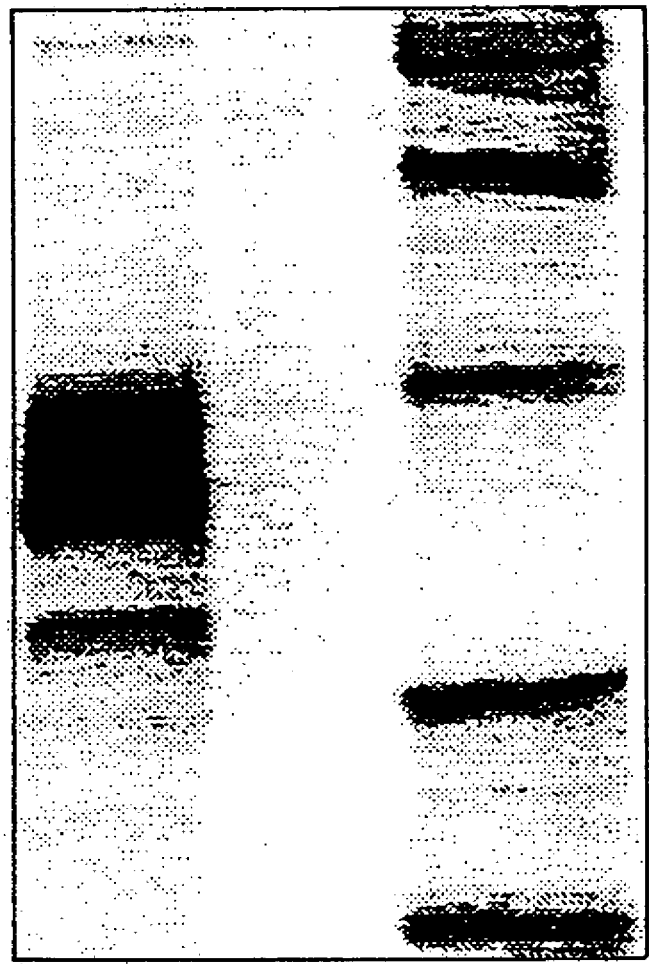
FIG. 12 shows expression of VP7sc in (A) CSL503 cells and (B) rabbit kidney and bovine nasal turbinate cells following infection with OAV206 virus. (I) Infected cells. (U) uninfected cells. (M) indicates marker proteins of the sizes shown.
Figure 12B:
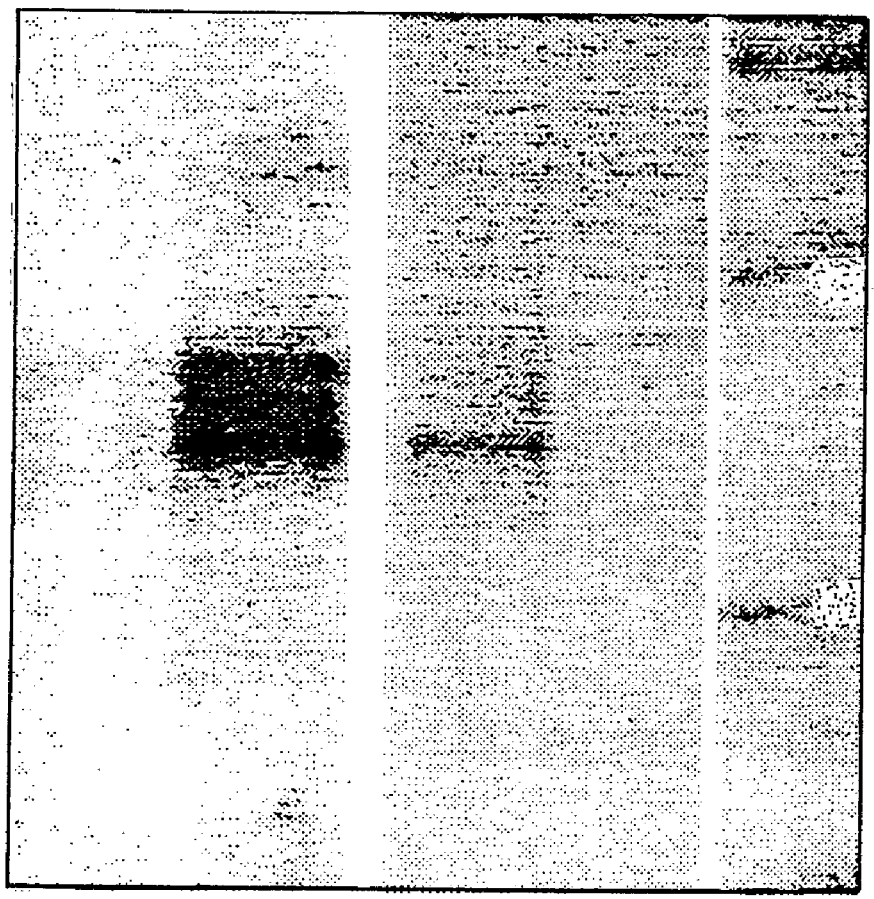

To determine whether the recombinant genomic clone was infectious, pOAV100 was cut with KpnI to release the linear viral genome and DNA was transfected into CSL503 sheep foetal lung cells using lipofectamine (GibcoBRL). Solution (A) containing plasmid DNA (2–10 μg) and 300 μl EMEM (containing hepes+glutamine), but lacking foetal calf serum (FCS) and solution (B) containing lipofectamine (10 μl)+300 μl EMEM (containing hepes+glutamine), but lacking FCS were combined, mixed gently and incubated for 45 minutes at room temperature. Subconfluent CSL503 cells in a 60 mm petri dish were rinsed with 3 ml EMEM (plus hepes and glutamine) lacking FCS. EMEM (plus hepes and glutamine) but lacking FCS (2.4 ml) was added to the mixture of solutions A and B, mixed gently and added to the rinsed CSL503 cells. Cells were incubated for 5 hours at 37° C. in 5% $CO_2$. The incubation medium was changed using complete EMEM plus FCS (10%) and cells were incubated at 37° C. in 5% $CO_2$ until virus plaques or cytopathic effect was visible (7–15 days).

To confirm that viruses rescued from transfection of pOAV100 and pOAV200 were derived from those plasmids a portion of the genome of wild-type OAV287, OAV100 and OAV200 viruses was amplified by PCR. For OAV100 a primer pair spanning the region of the mutated SphI site at bases 8287–8292 was used. For OAV200 the primer pair spanned the insertion site for the ApaI/NotI polylinker between the pVIII and fiber genes. Wild-type OAV287 DNA was amplified as a control in each case. DNA amplified from wild-type OAV287 was cut with SphI whereas the DNA amplified from OAV100 was not (FIG. 8A). Similarly OAV200 DNA was cut with ApaI, EcoRV and NotI whereas OAV287 DNA was not (FIG. 8B). Other viruses were similarly characterised by restriction enzyme digestion. Identification of MLP/TLS elements and Construction of pMT OAV287 TLS elements were identified as follows and as described (17). mRNAs present in OAV287-infected CSL503 cells were copied into cDNA by reverse transcription using primers complementary to the IIIa or fiber genes. A primer thought to fall within TLS exon 1 was then paired with each cDNA primer for PCR. DNA was successfully amplified, cloned and sequenced. This identified TLS exons 2 and 3 (which correspond to bases 8083–8145 and 8350–8412 of FIG. 1, respectively) and the 3' boundary of TLS exon 1 which occurs at base 5044 of FIG. 1. A second PCR strategy was then used to obtain MLP and TLS fragments suitable for assembly into pMT. The region in FIG. 1 between nucleotides 4861 and 5023, thought to contain the MLP was amplified by PCR using a plus sense primer which added an ApaI sequence at the 5' end and a 3' minus sense primer which introduced an NdeI site by point mutation at base 5012. Similarly, the TLS was amplified using a plus sense primer which introduced the NdeI site at base 5012 and a minus sense primer which was complementary to bases 8396–8412 and which added a HindIII site at the 3' end of the PCR product. The PCR fragments were digested with ApaI/NdeI and NdeI/HindIII, respectively and the fragments were cloned into Bluescript SK+ (Stratagene) cut with ApaI/HindIII. The resulting plasmid was then digested with HindIII/NotI and a synthetic oligonucleotide with HindIII/NotI termini and the sequence shown in FIG. 9 was cloned to produce plasmid pMT. Genes of interest were then cloned into convenient restriction sites in the NCS. Gene expression cassettes were subcloned as ApaI/NotI fragments into pOAV200 or rescued into infectious virus.

Infection of Cells and Expression of Antigens

CSL503 and other cells were infected with viruses at a multiplicity of infection of 20pfu/cell as described previously (21). Infection was allowed to proceed for 24–60 hr. Cells were then incubated in methionine-free medium in the presence of $^{35}$S-methionine to label newly synthesized proteins. The protein of interest was recovered from cell lysates by immunoprecipitation using a specific antiserum against the expressed protein (21). Recovered proteins were analysed by polyacrylamide gel electrophoresis and detected by autoradiography or using a phophorimager (Molecular Dynamics).

Results

To characterise the genome in molecular terms, BamHI restriction fragments representing the entire OAV287 genome were cloned into various plasmids and sequenced using methods described in Sambrook (9) and similar publications. Sequences were determined on both strands by using nested sets of deletion mutants together with synthetic oligonucleotide primers which were synthesized from newly determined sequences.

The viral sequence of 29,544 nucleotides (FIG. 1) is considerably shorter (by approximately 6.5 kb) than the sequence for human adenoviruses but many genes encoding structural proteins are identified by their homology with their Ad2 homologues (FIG. 2). It is clear, however, that the ovine adenovirus genome shows major structural and sequence variations compared with all other adenoviruses studied to date (FIG. 2), in the regions encoding both structural and non-structural proteins. In particular, (a) the reading frames tentatively identified as forming the E1A/B regions are named principally on the basis of their location in the genome. Very limited homology can be detected between the 44.5 kD open reading frame (orf) and the large T E1B protein of other adenoviruses. Homology in the putative E1A region of OAV287 has not so far been detected;

(b) in other adenoviruses the E4 region is normally located at the right-hand end of the genome. the OAV287 E4? region is tentatively identified based only on the presence of a protein sequence motif HCHC . . . PGSLQC (SEQ ID NO. 4) which is found in 18.8 kD and 30.85 kD orfs in this region. Identical or very similar motifs are found in the E4 34 kD protein of human Ad2 and Ad40 and mouse adenovirues.

Figure 3:
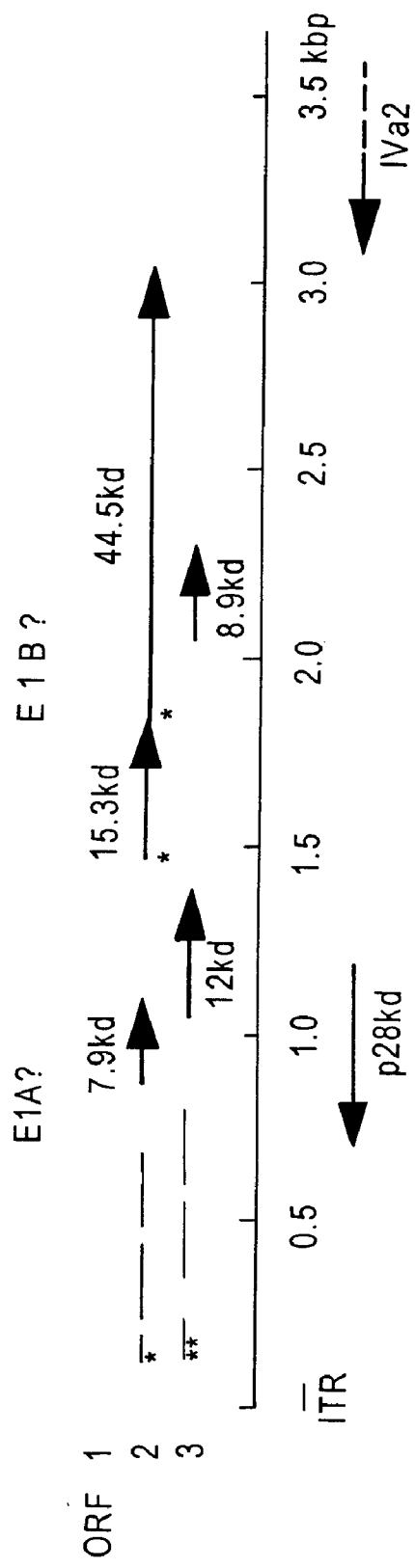
FIG. 3 indicates the major open reading frames in the proposed E1 region of OAV287. Asterisks show the location of possible initiation codons. A previously unidentified gene (p28 kD) which codes for a processed structural protein is encoded on the complementary strand.
Figure 4:
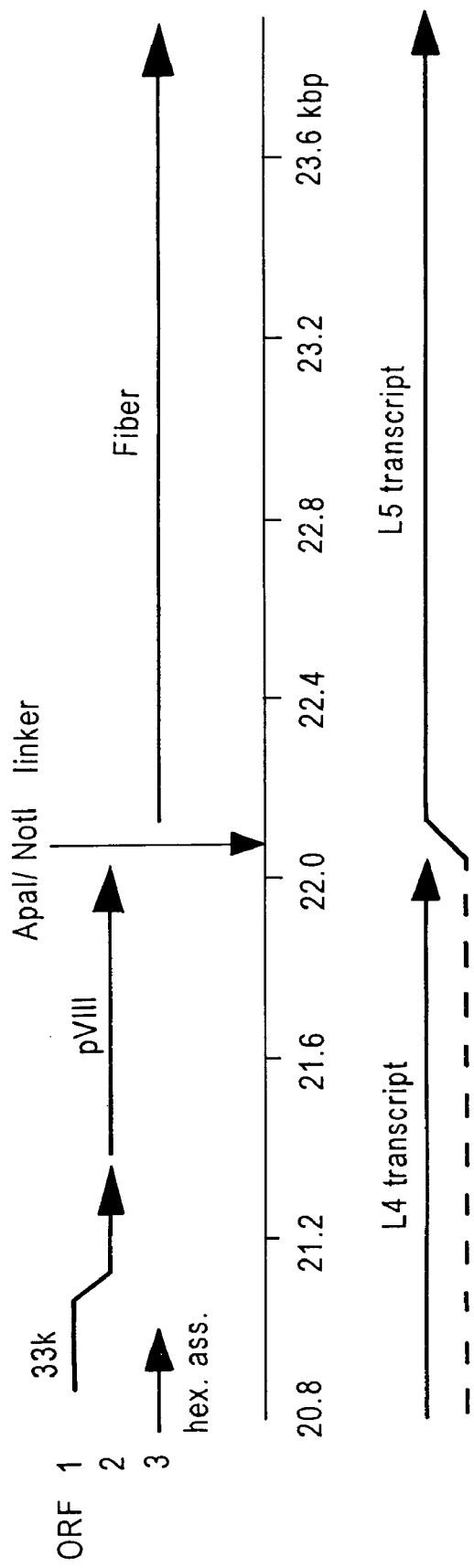
FIG. 4 shows open reading frames in the region of the OAV287 expected to contain E3. However, E3 is missing as the gap between the pVIII and fiber genes is only 197 nucleotides. The site at which the ApaI/NotI polylinker was later inserted is indicated.
Figure 5:
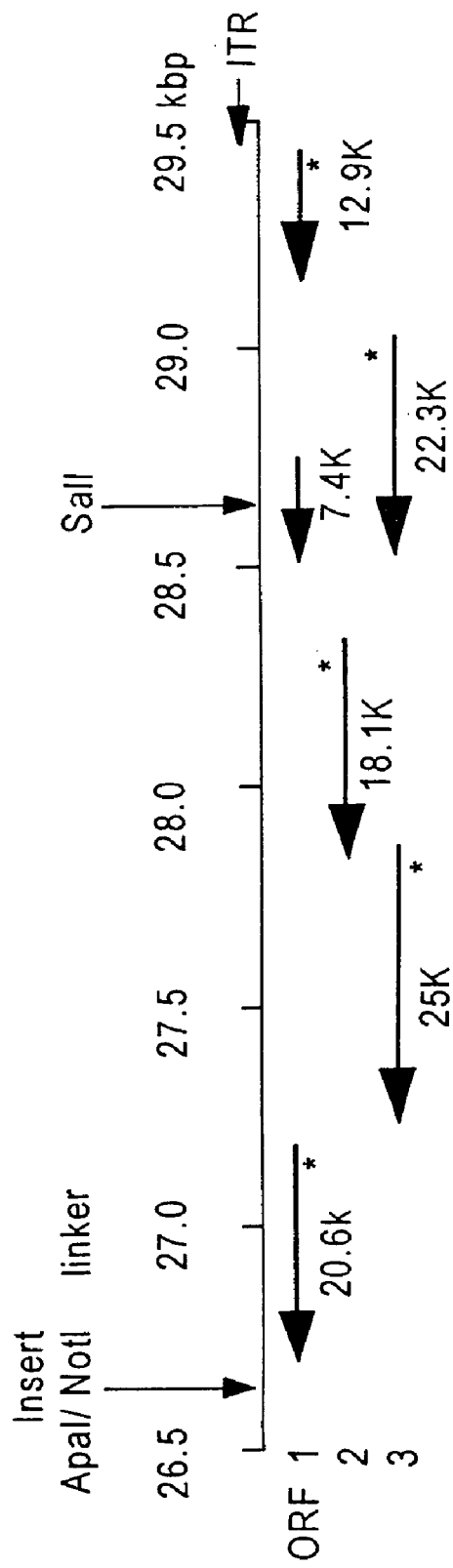
FIG. 5 shows the major open reading frames in the probable E3 region of OAV287. Asterisks show the location of potential initiation codons. The SalI site which was modified by end-filling and re-ligation and the alternative site at which a polylinker sequence was later inserted into the genome without loss of infectivity is indicated.

(c) the distance between the end of pVIII and the beginning of fiber, which in other viruses defines the E3 region, is only 197 nucleotides (FIG. 4). The E3 region equivalent, if it exists in ovine adenovirus, may consist of the cluster of open reading frames which are present in the right to left orientation on the complementary DNA strand, at the right-hand end of the genome (FIGS. 2 and 5). However, these sequences show no detectable homology with any other adenovirus and the functions of these proteins cannot be deduced from such comparisons;

(d) there is a region of approximately 1 kb which lies between E3? and E4? which has a very high A/T content (70.2%) (FIG. 1). As there are no open reading frames encoding greater than approximately 30 amino acids in length on either DNA strand it is unlikely that the region codes for any proteins, unless mRNAs are generated by very complex splicing events. This region has no known equivalent in any other adenovirus;

(e) other differences are apparent in the structural proteins of the virus. OAV287 lacks homologues of Ad2 proteins V and IX. However, OAV287 has a completely new gene coding for p28 kD which is located on the complementary strand of the E1A? region (FIG. 2 and 3). This is a structural protein with an apparent size of 28 kD by SDS PAGE which, according to N-terminal sequencing data, is cleaved from a larger precursor. No homology between this protein and others in the databases has been detected;

(f) in most other genomes the VA RNA genes are located between the Terminal protein and the 52/55 k genes. In OAV287 there is no room for them as the reading frames overlap.

These differences serve to emphasize the unique character of the OAV287 isolate compared with other human and animal adenoviruses. In addition, since the OAV287 non-structural regions show little or no homology with equivalent regions in other adenoviruses, sequence comparisons do not reveal the identity of likely non-essential regions of the genome. Moreover the viral DNA cannot easily be manipulated to test for dispensable sequences.

The present inventors have produced a plasmid containing a full length infectious copy of an ovine adenovirus genome in which the ITR sequences are linked by a short sequence which creates a unique restriction enzyme site. A plasmid containing a full length infectious copy of an ovine adenovirus genome linked to a bacterial origin for DNA replication and a marker gene has been produced. Partial clones of OAV287 genomic DNA were specifically modified and initially linked to a gene encoding antibiotic resistance and origin of replication inserted into the unique SalI site of the genome (FIG. 6 and see Methods). Such a plasmid can be grown in bacteria and more easily manipulated.

The circular genome clone differs from the naturally occurring circles that occur in Ad5-infected cells (10) and that might exist in OVA2887-infected cells in that the] 46 base pair ITRs are joined by a GATC linker. Together with the last and first nucleotides of the genome (G and C, respectively, see FIG. 1), this sequence forms a unique KpnI site when the ITRs are joined head to tail. Other sites such as EcoRI, BamHI, SalI, KasI, etc. which have recognition sequences beginning with G and ending with Care suitable if they are uniqueas the 3' and 5' terminal nucleotides of other adenovirus genomes are G and C, respectively. A plasmid with a sutable antibiotics resistance gene e.g. amp$^R$ and origin of replication can be inserted at the unique site or elsewhere in the genome to form a plasmid which can be propagated in bacteria. Plasmids propagated in the presence of 200 µg/ml ampicillin in $E.$ $coil$ strains JM109 and DM5-alpha retain the KpnI sites and inserted sequences, indicating that the OAV287 ITR sequences are stable when linked in this manner. This approach may therefore be used to engineer other adenovirus g nomes. If desired the GATC linker sequence can be removed and the authentic termini regenerated prior to transfection by digestion with KpnI (or ether appropriate enzyme) and incubation with T4 DNA polymerase to create blunt ends (9).

A method for generating linear infectious genomes from circular plasmids involved digesting the circular plasmid containing the full length copy of the OAV287 genome with restriction enzyme KpnI to generate a genome with the authentic 5' nucleotide dCMP. The linear DNA is then introduced into CSL503 cells using lipofectamine as the transfecting reagent.

To develop a viral genome as a vector it is essential to identify region(s) of the genome which are non-essential for function. These regions can be then substituted or deleted to make room for foreign DNA (11, 12), or they may be the site for insertion of foreign DNA. In the human adenovirus genome DNA has been substituted or inserted into the E1 and E3 regions (13, 14, 15) and at the extreme right-hand end of the genome between E4 and ITR, usually with the concomitant deletion of non-essential regions to facilitate packaging of the genome (16). Adenoviruses will package genomes up to ~6% larger than the wild-type, probably due to physical constraints dictated by the capsid structure (11).

Non-essential sites in the OAV287 genome were identified by insertion of a polylinker sequence containing ApaI and NotI restriction sites. This linker was introduced into the genome copy in pOAV100 between nucleotides 22,139 and 22,130 of FIG. 1 by site directed mutagenesis to create plasmid pOAV200 (FIG. 7). This corresponds to a site located in the intergenic region between genes for the pVIII and fiber proteins which was chosen because it avoids disruption of RNA processing signals in the region. A transcription termination site for the L4 family of RNAs maps 26 nucleotides upstream and the splice junction between the tripartite leader sequences and fiber mRNA maps 144 nucleotides downstream of the insertion site, respectively (17). Transfection of pOAV200 into CSL503 cells resulted in the rescue of virus OAV200. The second site at which the polylinker was inserted was located between bases 26,645 and 26,646 of FIG. 1. This created plasmid pOAV600 (FIG. 7). This insertion site corresponds to the right hand end of the A/T-rich region (FIG. 2) whose function and precise boundaries are unknown. The site was chosen as it is six nucleotides to the left of the transcription termination point for RNAs transcribed from right to left from the E3? region (FIG. 2). This was determined by sequencing cloned RT-PCR-amplified cDNAs derived from the region using methods similar to those described for the pVIII/fiber region (17). Transfection of pOAV600 into CSL503 cells yielded virus OAV600.

The above insertion strategy identified two regions of the genome which can be interrupted and created sites for subcloning gene expression cassettes.

A further non-essential site was identified using the unique SalI site located at bases 28644–28649 of FIG. 1. The site was cut with SalI, end-filled and religated to disrupt the reading frames which spanned the site. A plasmid pOAV600S (FIG. 7), which had lost the site was identified by digestion with SalI. When pOAV600S was transfected into CSL503 cells, virus OAV600S was recovered. The loss of the SalI site in this virus was confirmed by digesting the viral genome with SalI. As the SalI site falls within two significant open reading frames (which extend on the complementary strand between bases 28457 and 29014 and between 28511 and 28699), which were disrupted by end-filling and religation, the gene products derived from the reading frames are probably also dispensable. This group of reading frames may therefore constitute the E3 region of OAV287 as no other gene products in any adenovirus are dispensable for replication, in vitro. This implies that it should be possible to delete the whole region labelled as E3? in FIG. 2. In addition, in other experiments a 1 kb NdeI fragment was deleted from the region marked as E4? in FIG. 2. This deletion disrupted several reading frames in the region. No virus has been rescued from a such a plasmid, suggesting that it is not dispensable and accordingly, it may be E4.

Many viruses replicate incompletely in heterologous hosts, often entering cells but being unable to produce mature virus particles because of a block in the replication cycle. In the context of recombinant viral vectors, this represents a desirable safety feature, provided that replication is not blocked before appropriate and effective expression of the foreign gene occurs. OAV287 does not replicate productively in heterologous cell types (18), the only exception so far being bovine nasal turbinate cells in which viral titres are significantly reduced compared with the CSL503 cells. Recombinant forms of OAV287 have been constructed to determine whether expression of a reporter gene under the control of an appropriate promoter occurs.

Foreign gene expression requires that the gene be functionally linked to a promoter. This may be a viral promoter inherent in the genome, or a foreign promoter subcloned together with the gene of interest into a suitable site. The promoter driving gene expression must function in CSL503 and preferably a range of other cell types. In this work an OAV287 genomic promoter was used initially. Subsequently an heterologous promoter was also used. In adenoviruses, expression of the structural proteins is driven by the major late promoter (MLP). Families of RNA transcripts derived from the MLP contain a common sequence element, the tripartite leader sequence (TLS) at their 5' ends. The present inventors have identified those nucleotides in the OAV287 genome which comprise the TLS by using RT-PCR amplification of late mRNA transcripts present in OAV287-infected cells and sequencing of cloned cDNAs (17). A candidate MLP was expected to be present just to the left of TLS exon 1 (FIG. 2). The MLP and TLS elements were subcloned using PCR techniques into a separate plasmid pMT (FIG. 9) and linked with genes of interest. These promoter/gene cassettes were subcloned as ApaI/NotI fragments into the polylinker ApaI/NotI sites of pOAV200. Using this strategy plasmids pOAV203, pOAV204, pOAV205 and pOAV210 were constructed. These incorporate genes encoding a 17 kD soluble protein from *T. colubriformis*, a rotavirus VP7sc gene (19), the 45W antigen from *Taenia ovis* (20) and a membrane protein (PM95) from *Lucilia cuprina*, respectively. Plasmid pOAV202, contained the 17 kD antigen but lacked the MLP/TLS elements. These plasmids were transfected into CSL503 cells and rescued as viruses OAV202, OAV203, OAV204, OAV205 and OAV210, respectively (FIG. 10).

The human cytomegalovirus immediate early IE94 promoter plus enhancer, which functions in a range of human and animal cell types (21), was also linked to the rotavirus VP7sc antigen gene. This cassette was assembled by replacing the MLP/TLS elements in pMT/VP7sc with the HCMV enhancer-promoter region. The cassette was inserted in pOAV200 to create pOAV206. pOAV206 was transfected into CSL503 cells and virus OAV206 was rescued (FIG. 10).

CSL503 and other cells were infected with the viruses described above and at various times postinfection the cells were radiolabelled with $^{35}$S-methionine. Proteins of interest were recovered from cell lysates by immunoprecipitation using an appropriate antiserum. Recovered proteins were analysed by polyacrylamide gel electrophoresis and detected by autoradiography.

When virus OAV202 was used, no expression of the *T. coulbriformis* 17 kD antigen was observed by immunofluorescence. As this virus lacks the MLP/TLS elements and carries only the 17 kD gene this result demonstrates that there is no viral promoter upstream or adjacent to the insertion point between the pVIII and fiber genes which is capable of driving gene expression. As the E3 region is also missing from this site there is no requirement for a nearby promoter. This situation contrasts with observations made using a human Ad5 E3 recombinant (21). In this case a promoterless gene inserted 3' proximal to the pVIII gene was expressed, probably from the adjacent E3 promoter or the upstream MLP (15, 21). This result further emphasizes the unique nature of the OAV287 genome. Recombinant OAV287 viruses carrying the MLP/TLS elements were tested for expression in CSL503 cells. With OAV204, expression was easily detected in infected, but not in uninfected cells at 24 hr post-infection (FIG. 11A). Simiarly, when viruses OAV205, and OAV210 were tested, gene products of 24 kD and approximately 95 kD, respectively were detected (FIG. 11B). Therefore it is clear that MLP/TLS elements contain the necessary information to drive gene expression in the homologous cell line under replication-permissive conditions. However, when OAV204 was tested in a heterologous rabbit kidney cell line in which the virus does not replicate productively, no VP7sc expression was observed. Some replication occurs in bovine nasal turbinate cells, although to a lower titre than in CSL503 cells. In the latter cells, expression of VP7sc was detected following infection with OAV204 (FIG. 11B).

Virus OAV206 containing the HCMV enhancer/promoter element linked to the VP7sc gene was used to examine the function of a heterologous promoter in the context of the OAV287 genome. CSL503 cells infected with this virus readily expressed VP7sc antigen at 24–48hr post infection (FIG. 12A). With this virus VP7sc expression was also observed in the non-permissive rabbit kidney cell line and in bovine nasal turbinate cells (FIG. 12B). These results suggest that the HCMV or a similar constitutive promoter may be preferred over the MLP to drive gene expression in OAV recombinants in non-permissive cells.

One recombinant virus was also administered to sheep. Five sheep were vaccinated intraconjunctivally and intranasally with $0.7\times10^8$ pfu of OAV203. At three days post-inoculation virus was recovered from the nasal swab of one sheep and from the conjunctival swabs of two sheep and confirmed as the recombinant virus by PCR analysis. Animals showed no obvious ill effects from such vaccination.

The viral vectors of the present invention can be used for the delivery and expression of therapeutic genes in grazing animals. In species which are not normally infected by ovine adenoviruses the lack of pre-existing immunity should allow efficient infection, gene delivery and expression. The genes may encode vaccine antigens, molecules which promote growth in production animals, molecules which modify production traits by manipulating hormone responses and other biologically active or therapeutic molecules. The virus does not replicate productively in many non-ovine cells but the use of heterologous promoters allows the delivery and expression of genes while minimising the possibility of virus spread to a non-target host. As the DNA of adenovirus vectors can persist in cells in an unintegrated form, with the appropriate choice of promoter, expression over a prolonged period can be achieved.

REFERENCES

1. R. B. Couch, et al., *Am Rev Resp Dis* 88, 394–403 (1963).
2. T. Ragot, et al., *Nature* 361, 647–650 (1993).
3. M. S. Horwitz, in *Virology* B. N. Fields, D. M. Knipe, Eds. (Raven Press, New York, 1990) pp. 1679–1721.
4. W. S. M. Wold, L. R. Gooding, *Virology* 184, 1–8 (1991).
5. K. S. Raviprakash, A. Grunhaus, M. A. El Kholy, M. S. Horwitz, *J Virol* 63, 5455–5458 (1989).
6. A. M. Lewis, et al., *J Virol* 11, 655–664 (1973).
7. R. L. Peet, W. Coackley, D. A. Purcell, C. W. Robartson, B. M. Micke, *Aust Vet J* 60, 307–308 (1983).
8. M. Benko, A. Bartha, G. Wadell, *Intervirol* 29, 346350 (1988).
9. J. Sambrook, E. F. Fritsch, T. Maniatis, Eds., *Molecular Cloning: A Laboratory Manual* (Cold Spring Harbor Laboratory Press, Cold Spring Harbor, 1989).
10. F. L. Graham, *EMBO J* 3, 2917–2922 (1984).
11. F. L. Graham, L. Prevec, in *Methods in Molecular Biology* E. J. Murray, J. M. Walker, Eds. (Humana Press, Clifton, N.J., 1991), vol. 7, pp. 1–19.
12. F. L. Graham, L. Prevec, in *Vaccines: New approaches to immunological problems* R. W. Ellis, Ed. (Butterworth-Heinemann, Stoneham, Mass., 1992) pp. 363–390.
13. M. Levrero, et al., *GENE* (*Amst*) 101, 195–202 (1991).
14. J. E. Morin, et al., *Proc. Nati. Acad. Sci. USA* 84, 4626–4630 (1987).
15. G. W. Both, et al., *Virology* 193, 940–950 (1993).
16. P. K. Chanda, et al., *Virology* 175, 535–547 (1990).
17. S. V. Vrati, D. B. Boyle, R. Kockerhans, G. W. Both, *Virology* 209, In press, (1995).
18. D. B. Boyle, et al., *Vet Microbiol* 41, 281–291 (1994).
19. M. E. Andrew, et al., *J Virol* 64, 4776–4783 (1990).
20. K. S. Johnson, et al., *Nature* 338, 585–587 (1989).
21. Z. Z. Xu, V. Krougliak, L. Prevec, F. L. Graham, G. W. Both, *J gen Virol* In Press, (1995).
22. S. H. Larsen, H. D, *Virology* 82, 182–195 (1977).
23. E. Nakano, D. Panicali, E. Paoletti, *Proc Natl Acad Sci USA* 79, 1593–1596 (1982).
24. D. M. K. Rekosh, W. C. Russell, A. J. D. Bellet, A. J. Robinson, *Cell* 11, 283–295 (1977).
25. F. Sanger, S. Nicklen, A. R. Coulson, *Proc Natl Acad Sci USA* 74, 5463–5467 (1977).

It will be appreciated by persons skilled in the art that numerous variations and/or modifications may be made to the invention as shown in the specific embodiments without departing from the spirit or scope of the invention as broadly described. The present embodiments are, therefore, to be considered in all aspects as illustrative and non-restrictive.

The invention claimed is:

1. An isolated DNA molecule comprising nucleotides 1–29,574 of SEQ ID NO. 3 or an isolated DNA molecule that hybridizes to the complement of nucleotides 1–29,574 of SEQ ID NO. 3 under high stringency and which is capable of replicating autonomously as an adenovirus in sheep cells.

2. The isolated DNA molecule of claim 1, wherein the DNA molecule specifically hybridizes to the complement of nucleotides 1–29,574 of SEQ ID NO. 3 and shares at least 90% identity therewith.

3. The isolated DNA molecule of claim 1, wherein the molecule is identical to nucleotides 1–29,574 of SEQ ID NO. 3, except for differences in nucleotide sequences encoding viral polypeptides that do not alter the amino acid sequences encoded by SEQ ID NO: 3.

4. An isolated DNA molecule comprising the OAV287 inverted terminal repeat consisting of nucleotides 1 through 46 of SEQ ID NO. 3.

5. An isolated DNA molecule comprising a nucleotide sequence identical to nucleotides 1–29,574 of SEQ ID NO: 3 except for a deletion or alteration in all or part of the open reading frame that spans a unique SalI site at nucleotides 28673–28678 of SEQ ID NO: 3.

6. A plasmid comprising a bacterial origin of replication and a first nucleotide sequence as set forth in nucleotides 1–29,574 of SEQ ID NO. 3 or a second nucleotide sequence that specifically hybridizes to the complement of nucleotides 1–29,574 of SEQ ID NO. 3 under high stringency conditions and which is capable of replicating autonomously as an adenovirus in sheep cells.

7. The plasmid of claim 6 wherein the second nucleotide sequence hybridizes to the complement of nucleotides 1–29,574 of SEQ ID NO. 3 and shares at least 90% identity therewith.

8. The plasmid of claim 6 or 7 wherein a third nucleotide sequence encoding a non-adenovirus polypeptide is inserted into the first or second nucleotide sequence in a region that is non-essential for replication of the adenoviral genome in sheep cells.

9. The plasmid of claim 8 wherein the inverted terminal repeats of the first nucleotide sequence are linked together or the inverted terminal repeats of the second nucleotide sequence are linked together.

10. The plasmid of claim 8 wherein the third nucleotide sequence encodes resistance to an antimicrobial agent.

11. An adenoviral vector which is capable of replicating autonomously as an adenovirus in sheep cells comprising (1) a first nucleotide sequence having the sequence as set forth in nucleotides 1–29,574 of SEQ ID NO. 3 or a second nucleotide sequence that specifically hybridizes to the complement of nucleotides 1–29,574 of SEQ ID NO. 3 under high stringency conditions and (2) a third nucleotide sequence encoding at least one non-adenoviral polypeptide, wherein said third nucleotide sequence is inserted into the first or second nucleotide sequence in a region that is non-essential to replication of the adenoviral genome in sheep cells.

12. The adenoviral vector of claim 11, wherein the second nucleotide sequence specifically hybridizes to the complement of nucleotides 1–29,574 of SEQ ID NO. 3 and shares at least 90% identity therewith.

13. The adenoviral vector of claim 11 or 12, wherein the non-adenoviral polypeptide is a bacterial, viral, parasite or eucaryotic polypeptide.

14. The adenoviral vector of claim 13, wherein the non-adenoviral polypeptide is selected from rotavirus VP7sc antigen, *Trichostrongylus colubriformis* 17 kD antigen, *Taenia ovis* 45W antigen and *Lucila cuprina* PM95 antigen.

15. An adenoviral vector which is capable of replicating autonomously as an adenovirus in sheep cells, comprising (1) a first nucleotide sequenceas set forth in SEQ ID NO. 3 or a second nucleotide sequence that specifically hybridizes to the complement of nucleotides 1–29,574 of SEQ ID NO. 3 under high stringency conditions; and (2) a third nucleotide sequence encoding an RNA molecule, wherein said third nucleotide sequence is inserted into the first or second nucleotide sequence in a region that is non-essential to replication of the adenoviral genome in sheep cells.

16. The adenoviral vector of claim 15, wherein the RNA molecule is an antisense RNA molecule or ribozyme.

17. A plasmid comprising a DNA molecule having the nucleotide sequence as set forth in SEQ ID NO. 3.

18. A plasmid comprising a DNA molecule having a first nucleotide sequence that specifically hybridizes to nucleotides 1–29574 of SEQ ID NO. 3 under high stringency and a second nucleotide sequence encoding a bacterial origin of replication, wherein the first nucleotide sequence comprises ovine adenovirus inverted terminal repeat sequences that are linked by a third nucleotide sequence which contains at least one unique restriction enzyme site that is not present in the first nucleotide sequence, wherein said third nucleotide sequence is inserted into the first or second nucleotide sequence in a region that is non-essential to replication of the first sequence as an adenovirus in sheep cells, and wherein the first nucleotide sequence is capable of replicating autonomously as an adenovirus in sheep cells.

19. A plasmid comprising the DNA molecule of claim 5.

20. A vector comprising the DNA molecule of claim 5.

* * * * *

SEQUENCE LISTING

<160> NUMBER OF SEQ ID NOS: 4

<210> SEQ ID NO 1
<211> LENGTH: 29544
<212> TYPE: DNA
<213> ORGANISM: Ovine adenovirus

<400> SEQUENCE: 1

```
ctattcatat atataacgtt gcacagaggc ggggcgtgtg ggttttttat tgtttattgt      60
catggaattt acaaagaagt aagttgttgg atctttattc acaattcttt taacaatgac     120 tttttttactt attacatttt tcatcttttt tacttcacat gatattttac ttaaattttg     180
tacatacaag ccaaaattcg cataaaatgt cttactttaa aaagttaaat ttttttttta     240
acgcataaat ggacgtacag cagcaattgg aatagcagga agggccattg taaagtgtgt     300
tcctgctgat gccgctgcag aaaggataga tgctatcgta cgcataaacc cccctcctat     360
ttgttcatct gctgctttta ttatatcttc tgccaatcta ggtgatattt gcttttgaat     420
gctgtttcca aaagcttgca tcatcggatt ttcaattaaa tggattggat ttgcagaatt     480
tcctaaaaaa tagcccaacc catctaaagc agttaaaagt attctccctc caggaaccac     540
agatataatt aagcggagca accgagaggt taaattccag ggtcctccga agagagtatc     600
taggatcagg ccaagaagtg aaccaaaaag acttgtaagt agaagttgtc tgatatgctt     660
tggagaggac tgtaaaaatt gcaaaacggt atcaatgac catttcttct ttacttttac     720
atctgtatca tgttctccat cagaaggtct tattgggaag taccattggt cacgagcatc     780
tttgaagact tctgtttctt gaaattctgt tttcggtaag cgactagcag ttatggtatt     840
aggaatattg acggtaatgt tattcacatc tacaatttct ggaggaatcc atcttgcata     900
ggatgaaatg ggttttgtgg gttctttcaa tatataattg cgaggagggt ttttccaaaa     960
tctctgaaca taagtatttt ctgattttgg cggttttttg cttttttcgcg ctcttttttct   1020 tggctttggt ctttgaaatt ttttcttcct ttttctgtag gctcctcctg ctaaagctgt    1080
gttatttgtg acgtacatcc tgttagctac acgatttttcc cggactgcaa attttttttgc   1140 caaatggaaa agaaattgct gaaaccttct attaatcata taaattgtca gtggaatcat    1200
gaatcagata gtgcaggatt ttttcttttt gatactgata atttatacta ttatgtattg    1260
gatcaagtgt cttggatatg tttaagagat ataactcttc attgtgatcg catgtggtta    1320
gcggtttgtt tttgtttgtg caaatctaaa tttgatgtac acaatattct agcgggagta    1380
catgttatgt aatgaaaatg acgtcgggga ttgaatggat tgagccttat ttgacatttt    1440
tctgtgattt ttttgcctta ttaggaaata aatttgtggc gccagtacga tggagattgg    1500
aatgactcct gcatttacag aaaggaattt gtactgtgtt ttgcttgact ttaatttaag    1560
atggtatcag cagatattta acccaatatg gattaagcca aatttatggg ctttctctga    1620
ttttttaaaa aaaatggcct ttatttatgc tagcgacttg gcgttgttaa attcttacat    1680
ccctggtaat gtttgtaaca aacttgatat catcaagaaa gatcttcctg aagatttttac    1740 cgtgtctatg ttttgtgtct tagtgtgttg gcttgcttct ttctgtaaag gttctaatttt    1800 agctgaaact cgccagaatt gtcacgcggt aagcaaattt ctggcacaac tatcaaaatt    1860
aataaaaccc taattttttag tttgtaaaaa tagaattcaa attttttaacg ccacaatgac    1920 ttcggcggag ttttctgttg aatttcctta tgtttctaag ccaattgttc catggcctgc    1980
ttcggcatct tctaataatt catcgagtca gaatattgac tttcctgttc ttaaaccaga    2040
```

-continued

```
tcaagatcca atagccttct ttcaaactaa caatacggct tacttacaac ctggagctac   2100
ttattactgg aagtgtatcg aactgtcaaa gcctattcac atttacggtc aaggagctac   2160
agtacaactt gtcggacctg gacctgtgtt tgttttcaac agtgaaagtg ttattcctga   2220
agatttttac gtcgtgtttg aaaatatcaa ctttattgaa gatgaatttc ctattagaag   2280
tggccagtta agtttaggac ttacaactca cagtgctgta tggtttatca atgtatggaa   2340
aacttcaata gtcaattgta actttaaaaa ttttagggga gcggctcttt ggtattcaga   2400
taatagaaat ttttgaaatg cgagaaaatg gaatcagcag catttagttt caaattgtcg   2460
ttttaatggt tgtagaattg gaatttctaa tactggttca tctgaatatt ccatagccag   2520
tcaaaatcaa ttttatgatt gtcaaatctg ttttaatgta accgggggta attggtctag   2580
aaataataat gttattgtta actgtagatg tgcttatctg catgttggag ataacatgtg   2640
gtatgaaggc cattccgaaa ataataatcc cgctaagggt actttctgca ataacataat   2700
taaccatgct gataacggag gcaatgtctg gcctactcag tttaaactta cagatggatc   2760
aacgatacag ttagcatcat tttattttga tgataatcaa gaaattccac cttgttatag   2820
cggtaatttt cattggtttg gagatgtaaa cattgtaaat ttttctacca caaaaattga   2880
taaatggtgc attactggat gtaatttcta tggtaataca catgcagcta acgatgctgg   2940
tcaagttcag gttgctgaag ctgtaaaaga caaagtgttt attattgggt gttctggtaa   3000
taatgtaacc atgaaaaata ttgtagaagg taacatgact ccaaaaattg gtacaataaa   3060
gtaaaaaact ttttattcaa aacaaatatgg atttacattt aaacgtttta catattgatt   3120
ctgcgtataa gttctttttc taaacactct tctaatttcc atacatgctt gataaaacaa   3180
actttgtaaa ttcataaata taggtttgac ttgatcagaa ggtgaataat agctccatct   3240
aaatgattcg gtaataggaa cattattata tattaaccag ctatattttg agttaactct   3300
tgcatgatcc actatatctt taagtacagg gataagtgca ctcggaaatc caaaagaata   3360 gttttttaata aatctatta tctgtgaaga atcaagctgc ggactaataa catgacattt   3420
tgattgaatt tttaaatcct taatatttcc tctatcatga cgcgggttca tattatgtaa   3480
aactactaca acagtgtaac cattacattt ggcaaatcta ttaaaaattt ttgacggtaa   3540
agcatgaaag aaagaactta tagaatgaca tgatcccaat tgattcatac attcatctat   3600
tataatacag atagatcctt cacttgcagc tctgcagaat atattatctg gattatcaat   3660
atttagatta gtatcggaaa tagcatcttt gaaagctaat tgtataaatt ttggatttaa   3720 tgttttttgtt agtggattag agaatgcatc gtagtttcct tcaacacact gtgctttcca   3780
cgcaattttt tcttctaatg gaacagtacc tttttctgga gttatgaaaa aaattgtttc   3840
tggtattgga tcaattagtt ttccagatat aatatttctt ataaattgag attttccgct   3900
acctgtgggt ccatatacag taacaatgaa tggttgtaat ccgcagttta aactgggtat   3960
acagccatct tttaacagat tgtgagcctc atttacagtt ttttgataat ttacagcaat   4020
attgtgtaaa tcagtcataa gttgaccatg atacatacat ttatcaaaaa cttcttgact   4080
ttctggaaat ggatttctgc aaatagaagg atctatcttt acaacatcat ttttccaatt   4140
taatgtgtca cttaaaaatt ttcccaaaaa ggattttctg tcaatggttc ttgcggtctt   4200
ggatttgggt gtctcttgtc gtacgggtaa agtaagtatc ctttcttcca ctggatccct   4260
ttcctcatcg tttgatcctt ccaaggtctc agaattctgg ttagttgctt ctctaccacc   4320
gtgaatggta catcggttcc acttgcggtt tgcagtgtct ttttttaaact tttcctcgat   4380
```

```
gtctgaaact ctttctgtgg ttgttctaat aaattatagt cagtaaaaca atgttttaga   4440
atttcatagt ttaaacaatt tttagcatga cctttggctc ttaattttcc ttctccaata   4500
aatttacagt ttttcaagt tatgtctttt aaagcatata atttaggagc taaaatacat   4560
gtttctgaac tgaatgcttc agctccgcaa cggttacaaa cagtttcgca ttcaaccaac   4620
caagttagac atggatgttt ttcatcaaag attaaatttg agttatattt tttaagtcta   4680
tgtaatcctt ttgataacat gagttggtgg ccctttctg ttaagaataa cgagtctgta   4740
tcaccataaa tacttttat ctcccttct atgtaaggtt tacccatatc ttccccatat   4800
aaaatttctg cccactcact catgaaagct ctggtccaag ccagcacaaa ggatgctatc   4860
tgagttggat atcggttgtt cttgatccat tcttccttat cctcaatagt tgttaaaatt   4920
aaatcattac aatcagcaga taaaaaagtt ataggcttaa aagtcacgtg atcttgattt   4980
cctataaaaa gtggaaaatt aaatttttca tttgtgtctt tggaatcttt gggcggcatt   5040
tcaggtaggt tgaaaaata ctgattccac tcaaatgaac gttttggtaa tgatttacta   5100
atcacagttg tgtatgatgt aatttcagct gatccatttt ctaatctttt tttatctttc   5160
tcttcaatat tttcagcaaa cactactttc tttttatcta tacgggtagc aaacgaacca   5220
tataaagcat ttgataacaa tttacttata cttcgctgaa tcttgttgtt acttttactt   5280
gcttttcctt tagccataat atttactttc acatattttt gacataacgg tttccagtca   5340
ctccatacag catacatttc agagcttttg attattttgc atttccatcc tctattgtgt   5400
aaggtgatta aatcgataga ggtcagtact tcatttatca atgtttcatt tgaccagcat   5460
aactttccac ttttttaga acataatgga ggtaacacat caagataatc taatgatggg   5520
ggttcacaat cggctaccac aatcataggt ttgattgaat tgtcaaaata atctattttt   5580
tcttttcttt gtagtagttc ttgaaagtaa tctatttgtg cattggcttc aaaagcattt   5640
aaagtttttc catatggaag tggatgcgtt aaggcactag catacattcc gcagatatca   5700
tacacatata ttgcttcttc aaatattcct aaaaatgaag gataacatct tcctcctctt   5760
aaactcattc taacaaaatc atacattttt tctgatggag cttccaaatt tcttaggaat   5820
tcagagggat gatcttcttc attataaaag atttgtttaa acaatgcttg agtattacta   5880
ctaattgtag gacgttggaa tatattaaaa gaacactcaa gctttaaaga tgttgtacag   5940
aactcttgat aaccttctat aagttttca actaattgag ccgtaactat aacatcatca   6000
atacaatact ccttagcttc ctctaataag ttgtattttt ggttgtgttt tggtttgttt   6060
tgtaaatatt cttcaaatga attccaatat ttttgaactg gataaccatt gttttctttt   6120
tcatattctc ccaacataaa aaaatcattg attgccctgt aaggacaata acctttgcta   6180
acactcaact gatatgcagt agcagcgtct cttaaagaag agtgggttaa caaaaatgta   6240
tccctaacca taaattttat accttgccat ttcatatctt caaaattaat aattccattt   6300
ttccatcttt cataagttgt atgtgaaggt ttcttaaagc aaggatttgg aagagataat   6360
gtaatatcat taaataacag ttttccagca cgaggcataa agcttcttgt cagcttaaac   6420
attgaaagtt cttcactgtc tattccttct aatacatgac ttgcaagtat gatttcatca   6480
aaaccacaga tattatgacc tactacatat aattcaatat atcttggttc gcactgtttt   6540 aattttttt ctttatttaa gaccatgatg tcttcatatg ataaatttga ttcaagacca   6600
tgattttcac aaaacgttga ccagtatttt ttagctactg aaatttgtag ctctgttctg   6660
aattttttaa aagctatgcc aatttcatct tcttttttat ttaacattac aaaacattct   6720
ctgtttacct cataacctat atcggtagct attttagaag caatttttat gagtgattta   6780
```

```
catccaatta acttaaaaac caacaagtaa ggagttaact gttttccata caaagaatgg    6840
taagtatatg tttcaatatc ataaacaata aaaagacgtt ttgcttttat ggctccaact    6900
ggattaaatt tgattttttc ccaccagagt tttgtttcat ggtgaatatt gtgataatag    6960
aagtcccgtc ttctggatga gcagttgtgt atattactat aaattgttcc gcagaattca    7020
catttattct gttgtttaac agttttattt aaatatattt ctccttttaa atcaataat     7080 tctattggta acaaatttcc attaagaatt tcttcagtca tcttaaaaaa tcttttgttg    7140
aacttccata tttttaaaga tacggggggtg ttagaatcac aaagtttttaa aacatctaaa  7200 acatttctta ctttcttgaa agaatttaat tttaaaccct gaattgcaaa gtaattataa   7260 aaacttttttt caaaattctt gtagtatata aattttatat atgtatcctc atatattcca  7320
gtaatataag tagtagttct ttgctttatt attgtctttg aagccatctg tttaaagccg    7380
cttcccgtac tcgctcaaag cttcttaaaa caacttcatt tgtactatag ccaacaattc    7440
cagacaattt tattctaaat gctatttcaa ctgaatctaa atctgaaaaa tccgtgttta    7500
cttggttgat tacttcttct atgctcccac tgtcttctac gaagtctata tcttgaagta    7560
attggtctct ttcttctgga gttgaaaaag agtaagatct ttcattagct tctataattc    7620
ctaaaaaatc acgagttatt ctgctatata gttgtctgaa tgcttgtgtt tctctattaa    7680
accaaactct agtaaatata tcttctccat tttcatttct acctcttaat ataatttgaa    7740
caaattggat tccaatattt ctggcagcta acctattttg cactaaattt aagtataagt    7800
aatatagcgt gcttgccaca tgctctaata taaagaaata cactaaccat ttttgaataa    7860
aatcatcagt caatctattt tcattataaa atctaataag taattgaaaa aattcacttc    7920
cgtaattaaa aaaattactc cttcttgctt caggagttaa ttcttcttct aaattttgaa    7980
ttaaatctac tattgaagct atcacttcat cattaaattc ttccctactc agatcgcttg    8040
agctcggctc gcgatctgaa aatccttcat cttctatttc aggaacagta agaggagaac    8100
tagaagtttc ttcaacattc cttacccttt ggcgtctatt aacaggtaat ctatcaataa    8160
atcttctgat tacatcaccc cttgaacgtc tcattatttc agtaatagct ctataatttt    8220
ccctaggtct taatctgaat ggtaatccta ctcttgtccc tgaccttaaa gttaatgctc    8280
caccatgcat gccacctttt cctaaagtta atacagttgc taaatctttt aaattaattc    8340
gattttcagc ttctggaatt tccagctgtg aaaattcatc tataaaaagc tcaatccaga    8400
attcagaaaa aggtaagtct aatatacatt cactattatg catgttagac aaaattaaaa    8460
atttacataa agcttttttta attttacaaa ttaactttat aaggtaagta tccctttctt    8520
gcaaatttaa aaccataaaa gcttgagaaa aaggttgata atgctgctga aaagatctat    8580
tctgattttg agctgaaata gcggagccaa aaccttgcat gtctgcaagt tgcagactcc    8640
ctaatattct atccattaaa accgcgtttt gaatttgact aattgttttgt gaaaaatttt   8700 ctacattttg aattgctctc atatatgacc cagtatttat ggagtatgaa caatcagtta    8760
aaatttgcca ggtcatgcgt ctctcaaaac ttataggtga agatacaac ttatatgaaa     8820 tgttgctgta agtccgctga tcaaacagat actggtttaa aactcgcgcc acataaaaat    8880
acccaattaa taaatttggt ggaggttctc cttcaaatgg tggttgtgaa gtaacaggtc    8940
ctcttgggcg taaatcgagt aattgagtca ctggataatt aaaaaatcga ttagcccatt    9000
ttattcccct ttcatgtata gtccttgacc tggcaatact tcgattatta aggtcaagtg    9060
ttaaacgtaa atatcgtaag gtatgttgac tttgcccagt gagttgttgc cattggtgaa    9120
```

-continued

```
tctgcaaggc aaacaaaaaa tttatcttat tactgcagat gcatcctatt ttacaaaatt    9180
tacgttcatc attggaaact ccagacttat caagcaactc cccgggcacg tcaaataaaa    9240
atgaaaaaga tgaatttgaa ccagcagttg gcatttctag caaaccatct gatgaattta    9300
atatgagacg atctcaaaga gatgataatt tacctaaaag tcagatacca gtagtagata    9360
tactacatga taaaaatcct aaaatggcag aagaacgaga cttaatgtat aaatcttctg    9420
cttgcataaa acttgatgat tctaaacaat taaaaactga tatgttcagg ccggattttg    9480
ctggaactag tccagctcaa agacacatag aagccgcaga gctaaagaga atggatctt     9540
atactcgtag tttagaacaa tggacacatg attcttttat aagtcatgtt aaacaattac    9600
tttctagacc atttatatct ctaggtatta catatttgga tgattttttg cagacttatt    9660
tagatcatac tgaatcgtct tctttaaact ttcaactgtt tactttaata aatcactgtt    9720
cagaaaatac tttaaaacgg attttaaaac acatttctaa aaaaaatgaa aaaaatcaat    9780
atgtaaatca atggttgatt gatctcatta catgtatata tctaattata agagatgaac    9840
aaaatgttac agaacaagtt aatgcccttt tagtaactag taatcactta gctttacatt    9900
ttgcaaagaa agctacaggt ggattctatc ctacagcaga caagttagcg aagactcata    9960
tttttttcaa gagaataatt ttaggaatac tttcgctagc agaaagtata ggttgctata   10020
ctgtgaatcc atattgcaaa aatcctttga aaaagtcaaa agtagaagta gaaccaagtg   10080
acgaaatgta tatgttcagc ttaaaaggtg cacttgaaca tcctgattcc gacgaagacg   10140
aagacagtgg acttcaaaat gaataattat cataaatgga cttctaatgt tatagatgca   10200
attctatcaa acaaagctct tttagctata aaaattttaa aagtcaaccg tttgcaaaca   10260
aattgaatgc tttagaatca gcagttgtgc ctccaagaaa agatgatact cctgaaatga   10320
tagcaaatct tttaaaagaa ttagttgctt tgggagctat tcgcagtgat gaagttggcc   10380
cattatattc tgaccttctt atcagagttc acaaatataa tagcttgaat gttcaatcaa   10440
atttgcaaac tttaacagga gacattaaat cacttcaatc cgatataatt agaagttccg   10500
atattcccaa tttaagtaat caagttgttt taaatacatt tttaaattct ttgccctcaa   10560
ctgttacatt tggacaacat aattatgaag cttttaaaca aactctaaga ttatttgtta   10620
atgagacacc taatattaca gttttttagat caggaaatga tactttaatt caggttaaca   10680
taacaggaat tcatacaatt aatttgaatg atgcatttaa aaatttaaaa aattttgggg   10740
gaatagtatt aacaggtgaa tttattccag gtgatattac aagcagacta acagctaata   10800
caagagtact gctttatttt cttgctcctt ttacaaatga taatacattc acacctgata   10860
cttttctagc tttactcatg aaattatata gattgacagt ttcttctgct ttagattttg   10920
aagaagaaac tgaagctgaa gtagaaaatg tagctcaaca aataggatcc actagtgcag   10980
attttacaaa gacttaggga tatctattaa aaaacaaaga gaatcatttt tcgcctccca   11040
aatcattatc tcctagacaa ctgggtattt taaggttcat acagaaaagt ctggtagata   11100
aaattgatag aaataatgaa gatccatggg atgctttaga aactttatct tattcatttt   11160
ctccgtcatt ttatgaggcc aatgggcctt ttattagacg gttaataact tatatggaat   11220
ttgccttacg taattctcct acttacttca gagaaattta ctccaacaaa tattggatac   11280
cacccaattc attttggact caaaattatg cagacttttt ttcggaaaag aaagaaaaac   11340
aaaatttcga aacatttgaa ccgcgggaac ttccctttaca aatctctgag gaagaagctg   11400
tcccgcatac agaagatttt cagtcagcca tctcgccctc tatgggccaa acttcactcc   11460
ctgctccttc tgtgtcagaa tacagtagcg tgcctcggtc agcttttttac cctctcagag   11520
```

```
aacgtatcca agagagcatt tcaaaggcag tcatccctcc tttgacaggc tatgtcggaa    11580
aacaaatagg tgaaactatt ttccctggta gtggagatct tgtagcaccc gctgcgtctt    11640
tagttgcagc acaattggtt gattcaaggt ttaataacag aagacaaaga ttgaaagacg    11700
cagccagaaa gcgtcaccgc tatgttagag agatgcataa tatttctgat aaagagtcaa    11760
atgcttctaa tgatacggta atatcacctt tgattggaca tggttcgcgc actgaaaatc    11820
gttttgaata tttgagacct aaaggtggaa attatttata ctaataaaaa tcataacaga    11880
cctgacgggc ggtcatcctt ttttattaga tgcagaaatt tgtacctcca ccacgaatcc    11940
ttgctccaac agagggtaga aacagtatta cttatacgcc tctggcacca ctgcaagata    12000
caacaaaagt attctttatt gacaataagt cttcggacat tgaaagttta aactttacta    12060
ataatcacag taactttttt acaaatatta ttcaaaatgc tgatttggca gcggatgaag    12120
cagcaacgca agatattaaa ctggatgaaa gatctagatg gggcggtgaa ctgaaaactt    12180
ttataaaaac aaaattgcccc aatgtttcag aatttttaa cagtaatagc tttctagcca    12240
gattaatggt agataaaact gatccagaac atcctaaata cgaatgggta caaattacaa    12300
ttcctgaagg caattacact ggaagcgaac ttatagatca acttaacaat ggtattttaa    12360
acaattactt agaagtggga cgccaaaaag gagtagaaat tgaagacata ggagtaaaat    12420
ttgatacaag agatttttca cttggatatg atcctgaaac gggactaatt actccaggaa    12480
aatatacata taaagctttt catccagata ttatcttgct acctgaatgt ggcgtagatt    12540
ttacatattc tagaattaat aatatgttag gtataagaaa gagatttcca tatactaaag    12600
gatttcaaat tttatacagt gatttgacga agggaaatat ctctccatta ctgaatttaa    12660
ataactatcc tcattctatc gaacctgtaa tgcaagacga aaatggagtt agctataatg    12720
tagaaaaaat aagtgacaat ccccccagat ggcaaacaaa gtacagatct tggactttaa    12780
gttataaaaa taatggagga gctaaagccc taactgtact aactgttccg gacataacag    12840
gaggattagg tcaaatttat tggtcaatgc cagatacttt taaagcacct attactttta    12900
ctaacaatac tacaaagcca gaaacacttc caattgttgg attacatatg tttcctttaa    12960
aagcagggtt agttcataat ataaatgcgg tttattctca acttttggaa caaattacaa    13020
atacaactca gtattcaat agatttccta aaaatgctat actaatgcaa ccaccttaca    13080
gcaccgtaac atggataagt gaaaatgtcc cctttgttgc agatcacggg attcagccat    13140
taaaaaacag ccttacaggt gtacaaagag ttactataac agacgacaga aggagatctt    13200
gtccatacat acagaaatct ttggcgactg ttgtccctaa agtactttca agtgctacac    13260
ttcagtaaca atctggctga tatctctggg ccttatcctc ctggaaccgt tatgtctatt    13320
ttagttagtc cctctgataa taccgggtgg ggtattggaa catcaagtat gagggctact    13380
ggcttgaaat tttctaaaaa acaacctgtt agagtgcgac cttattacag agctcagtgg    13440
ggacagctta atgctcgtac ttcacttgag aaactaaaaa ccaaattgaa atattatgaa    13500
aaattgtaca gggacagact aaaaagaaaa acagttgttc aaagaaaaa gaggtcacct    13560 acatctcctg cggatcgact taaaaaatat cttaaagctg tcagtcaaat caaagctttc    13620
aatagagcta gaagagcagc ccaataaata ttattttca cttgcagatg aaggtagttc    13680
acgtgcttaa atctcctcat cgtcgaagac atacacgtcg ttacaaaaaa ctaaaaaaaa    13740
tcaatctatc tccatacatt ttacctaaag aattgcaagg cggtttttta ccagctctca    13800
ttcctatcat agcagccgca attagcgcag cccctgctat agctggaact gtaatagctg    13860
```

-continued

```
ctaaaaatgc taatcgttct taaaatttag aaaacttttt ttttaacaga tcacatggct    13920
ttttcaagat tagctcccca ttgcggctta acacctgttt atggccacac cgttggaatc    13980
tgtgatatga gaggaggttt cagctggtct agtttgggaa attcttttac ttctggttta    14040
agaaacatag gttcatttat atcaaatact gctcaaaaaa taggtcaatc acaaggattt    14100
cagcaagcca acaaggtct  actgcaatca aatgttttag aaaatgcagg acaattagca    14160
ggtcaaactt taaatacttt ggtagatatt ggaagattaa aggtagagaa agatctagaa    14220
aaattgaaac aaaaagttat agggaacgac caacaaatta ctcaagaaca attagctcaa    14280
ctaatagcca gcttaaaacc aaaagatgaa atgtttgtaa agcaatcaga aaaaattgtt    14340
gaacctatga gaccagaaat taaatctagc caaatgcctg tagaaatgtc tttttatgat    14400
tctgtaagtg atgaaccaat cataaaaacc aagaagtta  gccctccttc attttcatct    14460
gaatcttcac attcatattc tcacccaaga aaagaaaac  gcgtatccgg ttggggtgca    14520
ttttttggata acatgactgg agatggagta aatttaata  caagaagata ttgttattaa    14580
aaacactttt tatttacaga tggagccaca gcgtgaattt tttcacattg cgggtagaaa    14640
tgcaagggaa tacttgtctg aaaatctggt acaattcatc tctgccactc aaagtttttt    14700
taatcttgga gaaaaattta gagatccttt tgtagctcca tcgacgggtg taactactga    14760
ccgttctcag aaacttcaac ttcgtatagt tccgattcaa actgaggaca atgaaaactt    14820
ttacaaaact agatttactt taaatgtagg agataacaga gttgcagatc ttggaagtgc    14880
atattttgac attgaaggag ttattgatag aggacctact tttaaacctt atggagggac    14940
agcttataat ccattagccc caaaatcagc ttttcccaat gcagctttta tggatactga    15000
tgaagctaca acaatttata ttgctcaact ccctaatgct tataatgctc aaaacaaagg    15060
tgtagaagaa gcaattcgag tagaagcaaa cactactact cctaatcctc aatcaggaga    15120
atatgctact tatgactctg ccaaatttaa tccagaaact actggtgctt ctggaaggct    15180
tttaggaatt aatagcttag gagatctttt tccggcttat ggatcttatt gtagacctca    15240
atcagcagat ggtaacattt caactgcacc cataactaaa gtctatctaa acactactgc    15300
tacagatgac agggtcagtg gagttactgc agttgacacc gcaaccagat tgcatccaga    15360
tgctcattat attgaatata ctgatgaagc caaagctaca gctataggaa atcgcccaaa    15420
ttatattggt ttccgagaca attttattgg actcatgttc tacaataatg gttctaatgc    15480
aggaacattt tccagccaaa cacaacaact taatgttgtt ttagacttga atgacagaaa    15540
cagtgaacta agctatcaat atctaatagc agatctgaca gataggtata gatattttgc    15600
actttggaac caagcagttg atagttacga ccagtatgtc agaattttgc ataatgaagg    15660
atatgaagaa gcccctccgg ccttatcatt tccttctcaa ggtatccaaa attatttcat    15720
gcctactgcg gcaggtaatg cgatgacagt agacacgggt agaaatactg cagcaaaaac    15780
agataacacc aaggctttta taggatatgg caacatgcca tctttggaaa tgaatctgac    15840
agcaaatcta caacgtacat ttttgtggtc taatgtagca atgtatctgc cagataggct    15900
gaaaacaaca ccacccaaca taatctacc  tgatgacacc aactcttacg gatatataaa    15960
tggaagggtc cctctagcaa acataataga tacatggact aacattgggg ctaggtggtc    16020
attagatgtt atggatactg taaatccatt taatcaccac agaaattcag gactaaagta    16080
taggtcacaa ctgttaggaa atggaagata ttgcagattt cacattcaag tacctcaaaa    16140
attttttcct ataaaaaatc ttttgttgct gccaggaaca tataattatg aatggtactt    16200
tagaaaggat cccaacatgg ttttcagtc  tactttaggt aacgacctta gagcagatgg    16260
```

```
cgcaactatt acatacacca acataaattt atatgtttca ttttcccta tgaattatga    16320 aacagtaagt gaacttgaat tgatgttgcg taatgctact aatgatcaaa actttgcaga    16380
ttatttgggt gcggtaacta atctttatca aatcccagct aatacaaata ctgtagtagt    16440
gaacgtacca gatagatctt ggggtgcttt cagaggatgg agtttcaata gaattaaagc    16500
ttcagaaaca cctatgatag gagcaacaaa agatccaaat tttacttatt caggatctat    16560
accgctacta gatggtactt tctatttaac acacactttt caacgagttt ctattcagtg    16620
ggattctagc gttccatggc caggagatga taggcttttg attccaaatt ggtttgaaat    16680
taagagagat cctaatatgg acgcagaagg ttatactatg agtcaaagta ctatcacaaa    16740
agatttttat ttggtacaaa tggctgctaa ttataatcaa gcttatcaag gttataaatt    16800
gccagtacat tctaaatatt atggatttt agaaaatttt caacctatga gtcgccaagt    16860
accaatttat ggtaatggca cttatgattt atatactgct tatattacaa accaaagaac    16920
catgcaaatt tggaataata gtggtttaga atctaaaact tcaaatcctc ctatgttatc    16980
caacactggt catctttatg tagctaactg gccatacct ttgattggac caaatgctat    17040
tgaaaaccaa caaactgaaa ggaaattttt gtgtgataag tatatgtggc agataccatt    17100
ttctagtaat tttttgaata tgggtaattt aacagattta gggcaaagtg ttttgtacac    17160
taattctagt cattcactta atatggtttt tactgtggat agtatgcctg aaacaactta    17220
tctaatgctt ttatttggtg ttttcgacca agttgttatt aatcaaccaa caagaagtgg    17280
aataagtgta gcttatttgc gccttccttt ttcagctggt agtgcagcaa catgagcggc    17340
acatccgaaa gtgagctgaa aaatctgatt tcatcattac atttaaataa tggatttttg    17400 ggcattttg attgcagatt tccaggtttt ctgcaaaaat ctaaaattca aactgctatt    17460
attaatacag gtcccagaga acaaggcgga atacactgga taacattagc attagaaccc    17520
atttcttata agctatttat atttgatcca ctcggatgga agacactca attaattaaa    17580 ttttataatt tttcactaaa ttctcttatt aaaaggtcgg ccttaaataa ctcagacaga    17640 tgtattcag tagaaagaaa tactcaaagt gttcaatgta cctgtgcggg atcgtgcggc    17700
ttgttttgta tattttttctt atactgtttt cactttttata acaaaatgt atttaaagt    17760 tggcttttc aaaaattaaa cggttcaacc ccttctctga tcccatgtga accacatcta    17820
ttacatgaaa accagacatt tctttatgat tttttaaatg caaaaagtgt ttattttcga    17880
aaaaattata gaacatttat tgaaaatact aagactggat taataaaaac acattaattg    17940
tattcttgct ttttgacgtt ttcattagtc ttcatcttca tcttcttctt cactgctaga    18000
ttccaagatg gtttttttt tctttgatgg agtaggctct tcaatagttc caaaggatt    18060 catatcagaa tcctcttcta tgttaggcaa catagtattt ttaacctgga atgactgatt    18120
ccacttaaat tgagaaaact gaattggaat gttatttccc atacattcat tccaaaattt    18180
acgcacaaga gttaaacact gtaacatatc tggcaagcta attttcatct cacaaaattt    18240
tccattatta cgtctcaagt tgtattgata gttacaacat tgaaacacaa aaacagcagg    18300
gaatgtaact gctgcggcct gaactctatt aacatcctga acatcaattc cttccactcc    18360
agatatagaa aatggagtta ttttagggag ttgttttcct attgtttgtt tgccaccata    18420
attacattca cactgaccca atataaaaag catatttccg actttagctt tcggaaacac    18480
agcttttgta gtttcaatgg catttttgcat agccagcaag gccttctttt catctgaaaa    18540
gttaagacca caactgcgag gagaacattg cccaaaacgc tgatgggcat cctcagcaca    18600
```

```
taacacgtaa tgttcctgaa ctattttac tacttgttta ttcatacgcc cattactaag    18660
aacacccctc ccttccttta gggcttgcac ccctgcttcc gatgttggag gcatttcaat    18720
ttcattcacc cttttaaaca tgaagtcacc atgaaaacat ctaggacggt cctcctccca    18780
atcatgatac cacaaataac aaccagaagc attaaagttt ggaatcaagt caatttgctt    18840
acaaattgca ctatatagca ttctacctcc tacagtagcc atagatttac tgctactata    18900
agtcaaattt ataattttca tcttttttcat gtactgagca ataattttt cacaatctcc    18960
ttcttcagga tgaaacttca tttgactggt atcaactta cacactctc caaatttagc    19020
taaaatttcg agcgccgctt gaactttatt ctgaaattct tctgtagtag attttctctt    19080
cttgatagat ttagtaactt ttttagaaga cattatgtta gttttttct cgttgtagga    19140
tggctgaaaa aaatatggga gagtcagaga agggtttgaa cgaagaagaa tttaactcta    19200
ttctatcaaa acatctggaa agacaaatta aaatctgtaa agcgttaaca tcaaaattat    19260
cgaactggaa tattggaaca ttgttagaaa acttgttatt ttgtcctgat gaaagacaat    19320
catcaggtga tcccgaccca aaactaaact tttatccgcc tttttaatt ccggaatgtc    19380
ttgcattgca ctatccattt tttctaacaa ctcctattcc gctatcatgc aaagcgaaca    19440
aaataggaac taacacttac cgaaaatgga tgaacaatca agtcctggat ttacaaatac    19500
cttccttgga aaattgcaaa tgggatgata gcttgggaaa tgtagattta attgaagagc    19560
ttaaagagaa ccaaaaactt gttttagtaa acaagacca tgaaagaaat atatggttta    19620
aatcaaaatg caaacaactt caaagtttca gctatccctc actcagtctg cccccagttt    19680
tacaacaagt tttaattgaa tctcttatcg gcattagtca ggatcctaat aactttgaca    19740
aaaattacga acctgcaata actctagaaa aactacaaca tgtaaactgt gatcaagatt    19800
taaaacaagt tcaacaaaaa gtatcttcag ccgctacata cggaatactt tgaaatgca    19860
ttcagacttt attcagtgac aaattattca ttcaaaactg ccaggaatca ttacattaca    19920
cctttaacca tggttatgta aaattacttc aatttttgac aaatgtcagt ttaagcgaat    19980
ttgtaacttt ccatggttta acacacagga acagactcaa taatccgcag caacatacac    20040
aattggcaac cgaagacaaa atagactata tcatagatac agtgtattta tttttggtat    20100
ttacgtggca gacagcaatg gatatttgga atcaaacatt agatgataaa acaataaata    20160
taattaaaga ggaattaaac caaaattttg agaaaattgt caaagctgaa tcagttgatg    20220
aagtttctga aattttaaag tctattattt tccctgaact catgctgcga gcttttttgtt    20280
ctaatttacc tgatttttata aatcagagtc agatatcaaa ttttagaaac tttatctgca    20340
ttaaatccgg cataccgcag tcaatttgcc ccctattacc ttcagatcta attcctttaa    20400
ctttcctaga aagtcatcca atactctgga gtcatgtaat gttactaaat cttgcttcat    20460
ttctagtaaa ccaaggcaat tatttgcatg aacccgaaaa accttaaat atttcatcag    20520
tttactgtaa ttgtaattta tgctctccgc aaagaatgcc atgttacaat agcagtttga    20580
tgcaagaaat actaaccatt gataaattcg agttcacaaa ctctgataaa acaaaacagc    20640
taaaactgac cctccaaact tttgctaatg cctatcttaa caaatttaac tcagcagaat    20700
tctaccatga ccaagtttta ttctacaaaa actgtaaaag taattttct aaccaattaa    20760
cagcttgtgt aataaaagac gaaaattat tggctaaaat agcagaaatt caataacgc    20820
gggaaaaaga actcttaaaa agaggaaaag gaattttatt tggatccagaa acaggagaaa    20880
tcttaaacaa tggagaagcc atatcatcct ctgaaaactt ccaaaggcaa agaactagct    20940
atgctctacc atcaaatgaa ggagagcgag ctggatggga agccgatgag cgaagaagac    21000
```

```
gaaggagaag tgagtgagga tgaaacagag acaacaattc caaagaaaat gaagtttaca    21060
agtaagtaag ctctaaattt tttatattaa aaactgaatt tttttagaca aaattatttt    21120
aaattaaatc tttatagcta gcagttgatc tttgttcgtt tttcagaaaa ctcaagtgtt    21180
cagtcatatc aagttcactt gcctctgaaa cacgaaattg cggaaattct agaaaaaatt    21240
agactagaat ctaaaaaata tccaggaaaa gtttatcaaa taagaaatag aactccagca    21300
agtattacaa aacgatacct gtatgaaaga gatctgaaga aactgttcca gtatctagaa    21360
gacgcaaaga agctttacgc taagtaccaa agctgaggct ttatagtttt aaattttccc    21420
gccatggctc aaccagtgac gccttacgtc tggaaatacc aaccagaaac aggatatact    21480
gctggagccc atcaaaatta taacactgtt atcaactggt tgcatgccaa tccacaaatg    21540
tttgccagaa ttcaacatat aaacaccgca cgcaatgtta tggacaaatt ccgctctgat    21600
ttgacccgag atgacatcgc ggttaacatc aacaactggc ctgcagagga tttaatgcaa    21660
cctcctaatt ttccttacat tcctgcgacc tctaaatccg cttcaaccat aaatgactgg    21720
ttggctacca ctcaaggaat tcaactcagt ggaactagtg aactaaacgg gtggggatct    21780
aaccgcctga cttcctatcc ggatattcca cccattttaa agtatgaaag gcctggtcaa    21840
caacttcaag gccaaggact ttttaagcaa gaaaatattc atttatttta cgaatctccg    21900
cgcctccctc gctctggagg attaactccc caacaatttg taaaagaatt tccgcctgtt    21960
gtttataata accccttctc agaatctatg agtgtatttc cgaaagaatt tagtcctttg    22020
tttaacccct tcagaatctt tgaaaaaaca tccagtcaaa ctttacaata taaataaaaa    22080
acttctattg atctttatac ttacactaaa gcatcgcgtt tattttcgtc gccataaaaa    22140
tatatcaaag accccgtaatt ctctaacttt aaatcatttt ttgaactaat cttaatccat    22200
ttaaatgtag gaattaatat atcagaaacc agtaacaagc cagaattaaa atatacttgt    22260
gtcattttta cagatgaagc gagcacgctg ggacccggtt tatccccttt ctgaagagag    22320
actggttcct ctgcctcctt ttattgaagc cggaaaaggg ctaaaaagcg aagggttgat    22380
cttatcttta aactttactg atcctatcac tataaatcaa accggtttct taactgtaaa    22440
attgggagat ggaatattca taaacggaga gggtggccta tcaagcactg ctccaaaagt    22500
caaagttccc ctgactgtct cagatgaaac attgcaactg ctattaagta attctctaac    22560
aactgagtca gactctttag cttttaaaaca accgcaactt cccctaaaaa taaatgatga    22620
ggggagttta gtattgaact taaatactcc tttaaatcta caaaatgaga gattgagttt    22680
aaatgtttca aatccactaa agatagcggc agattcttta actataaact taaaggaacc    22740
cctaggattg caaaatgaaa gtttgggctt aaatctaagt gatcctatga atataactcc    22800
agaaggaaat ttaggtatta aattgaaaaa tcctatgaaa gttgaagaaa gttctttagc    22860
cttaaactat aagaatcctc tcgccattag taatgatgcg ttaagtataa acattgcgaa    22920
tccattaact gttaatacaa gcggatctct aggaatatct tattctactc ccttacgaat    22980
ttcaaataat gctttatcat tatttatagg aaaaccttta ggattaggaa ctgacggctc    23040
tttaactgta aatttaacta ggcctctggt atgtcgtcag aacactttgg ccataaacta    23100
ctcagcccca ctagtgtcat tgcaagacaa tcttacttta agttatgctc aaccattaac    23160
tgtaagcgat aattctttaa gattgtctct aaattctcca ctaaacacaa atagtgatgg    23220
aaaacttagt gtaaactatt ctaatccttt agttgtgact gactctaatc ttaccctcag    23280
tgttaaaaaa cctgtaatga ttaacaacac aggtaatgtt gacttaagct ttacagctcc    23340
```

```
cataaaatta aatgatgcag aacagttgac tttagaaacc actgagccct tggaagtggc    23400
cgataacgct ctaaaactga aacttggaaa aggcttaact gttagtaata atgctttaac    23460
cttaaacctt ggaaacggtt tgactttcca acaaggtctt ttacaaatta aaactaatag    23520
ctctctaggg tttaatgctt ctggggaatt atcaacagct acaaagcagg gaaccataac    23580
cgttaacttt ctaagcacaa ctcctatagc ttttgggtgg caaataatac ctactactgt    23640
agctttcatt tatattttat caggaacaca atttactcct caatcccag taacttcttt    23700 aggttttcaa cccccacaag acttttgga tttcttcgtt ttaagtccgt ttgttacatc    23760
tgtaactcaa attgtgggaa atgatgttaa ggttattggc ctaactattt ctaaaaacca    23820
atctaccata actatgaaat ttacttctcc cttagctgaa aatgtaccag ttagtatgtt    23880
tacagcacat caattcagac aatgaatatt ttaaaaattc tttattaaag agtaatcttt    23940
ttacataccg ttcttgacat aatgtgcctc tataattaac aaatctaagc aagcaaggtt    24000
gatcattgga atctatagaa gcataactct tccaataagc ataatcatat ggcggtaaat    24060 gaaacccct taaatctacc atattcatct ttaagtgtac agtatctaac aggttttac    24120 aatcttgcac ttctggactt ttaaaaacaa acagtacttt cataggacaa caattgtaac    24180
ggttataatc tgttacaatt ttacttattt cttcttccaa tggcaaagca ttccaaagtc    24240
ttgttataag tactgtaaaa tcatcaaatg aataacataa cacatttgta caacaattgg    24300
tccaaggtaa aaaacaggc acacgaacat gaactttttt taaaattaac atcagtgtct    24360
gttttaaact ttgacattgc aaagaatttg gctgcaagca atgacaatga aattgatttt    24420
gctgacaagg taagtcacac aaatacaact ttaacagcct aaatataacg acattaatgt    24480
aactttccaa gactttaaaa ctaacaaacg gtatatcaca ataaaaaga tgatgaatcc    24540 cttcgcaaca cataatggag ttcatgctac atccaaagat ggttccgaca aacctctgta    24600
aattaaagaa caacaataca acatacgaag aaaattaaaa cgttttttcaa aacgagatat    24660 acattgctgc aaagtatctg aacatttaca ttttatactt ataagctcac aagtttcaga    24720
aaatgtaatt cgtttaacag tttgatatga ataccatttt gaagaaaaat agaaatagtt    24780
ttgtgcattt gtgaagctcc cagaaacatt aacggacagc aaatccaagt attacaacaa    24840
acaggaacag tcttaacgtt tcgttcagaa aacaaagtaa caggcatatg attaaagcaa    24900
gacaataaaa cacttttggc agctaaacat tgcaaagatc caggtgaatt acaatgacaa    24960
tgataataaa acttataagc catatcggcc ctcttgcaaa acgaatcagc tttttggctt    25020
ataggaaaat aacaaaaaaa ctgattatat atgaatggag ttaatatctt cttcaaatta    25080
tacacacgaa tagcagaacc aagacgacca cgcccaacac aggtaaatat ttcaagtcca    25140
tgactaggaa cagatggttt ctcacaagca acaactttga tttgcttatc catcactgcc    25200
aatcaggctt aataggaaaa gaagaaaaat aattttccca ataataacga agaaattcc    25260 acgtttcatc ctgtacatta ctagtcacaa atacaacctc cgctatcaaa gattccctat    25320
catttaaaac tcccaccaaa ttgtcccagt ctacctcaaa aaagccagtt cccatatttt    25380
caaaatttgc ccatttttaaa taatccaaag catcaaattc aggaaacaaa tctttctgag    25440
ctaaaacata tacagtttta tcgccattaa atctaaaagc catcctaaat ggacctctag    25500
cccagtagtt taagtaccgg gaagagacta tacaatatac ttgatattga tgtctgttaa    25560
gtggtgataa aaaagaaagt aattcagaat taggataaag cattctccca tgttgattca    25620
tctacaaaaa acaaaaaaat tataaggttc atagaaaacc tactatttaa caaatctata    25680
aaaatgcatt aaaaagttac cttgaatata aattcagatc acctaaaaaa cgaaaaaaaa    25740
```

```
taacatttat gttagtaaat gatagtcttt aaaaattaga aaagaatcaa gtcgctttta    25800
tacttacaaa ctccaaataa attctgtaac caagagaaaa attgtaacct aaaaggtaaa    25860
gaagaacatt ataagattaa aaccactcta aaatctgaaa agcattatga aaaattctga    25920
tagctgcaac ttactagtct tctccaaatg ttgcaggcat ttcaaaaaat caagaggaaa    25980
accggagttt ataaagtagt agtctgatta tatctgaaaa agtttaactt ccttttcaac    26040
ccaacccagt ccaataaaat tccaaccttaa acttctttcc tgctaaaact ccataaaagt    26100
ccaattacca cttgactttt atttaacctc aattatgtta catgttattc tacccataaa    26160
aacttgatga ccaagaactg acctttccca tgttttctg aaataacaaa aatgttgatt    26220
taaagatttt taactaccca aaaacccgc tctcatgatt ttttcttata taaacaggat    26280
acaaaagaac tggcaaagat attccatcat acttctccaa ctgtcaaaac ataccactta    26340
acctctccca tgttttttcc cttttgcaca aacaggatat aaaaaatatt tttgccacaa    26400
tgtttttcct tttactcaac tgccagaata aaaatgaaca gcttaacctt ttccctctt     26460 aacccattgc gttcctctaa gaaaaaaatt atcccgccca atatgctaaa ggcttctccc    26520
gccaaaacag ctcaacttaa aatctctcat gaataaaacc cagagaaaat ttccagtaat    26580
aaaaattaat aaccgtgaag tactagatct aataatgata ttttgaactc ataaaaatcc    26640
accatccatg taatgttaca aacacttttt tattgagttt tttcttacaa ctgcattaca    26700
tacaggccaa gcatcaaact ttcttctgta tttcttccta gaccacaaaa ttacagactt    26760
atatttctgc cacaaatctc tatgatcttt acagtaacac ttacatttaa atggggaata    26820
cagcagcaaa taaggatgag ttaaacatgc gatacaatga ccagaaggaa gataatacaa    26880
tacatcacac caaaatgaag gtacagacaa catcgcatga aatcttaaat gtgattttac    26940
aataaatttc tgcagcagct tacaatctat attagcaaac cgttttatat acaaacataa    27000
aaacttggaa cttttcacca actcaatcat gttattataa cacattacaa attttgctat    27060
atctttattt gtcaaataac aaaatatctc aatccacagc tcatctggca gcaaacttcg    27120
caaatccatg acctgtaaaa gatacaacag aaaacagaaa attaatgcca ttcaataaca    27180
taaaaaatac agtcaaatca catactttt ctcacttaca aaactttgtg agcaggcctc    27240
caaaacaaac ttcagaaaat ggatgcatac aagaacattc tcctctcaaa aattgcttta    27300
actgaatgcg gcattttgca cctccagaaa aatgcagtcc attgagaggc tcttctctta    27360
aaacacagaa atgcttctgc aaaatctgta aagaaactaa caacttccaa attccaatca    27420
tcatgcattg caaagaagga cattcaacag caaaaggatc gtgatgagcc aataaagctt    27480
tactgtatga ctcattttca tgaattacag tctgtaactt actataatgc attttaagct    27540
ctgcttcaca aattaataat gctaatttct ttaagcagct caaagaaaac tcatcaggac    27600
aacggcattt aagaaagcaa caaaatgatt tcttaaaata cattttttcca gcatgatgaa    27660 caataaaaaa tttcaacgtt aaacaatgca aaaatgcatt tttatgcaca gtgaaagtaa    27720
ttttttcagc tgaagctaaa tcacagccta ttttattaca tgattttgta tgctccaaaa    27780
gagcttgttt taattgcttc aaatccatct tcttacaatt ttttcttttt ataaacacca    27840
gaaccgcatt caggccaatt ccagttattg tttaaatttg ctacagaaac tgcagaccac    27900
aaaaccacat cctctaaatc aacccacaaa gatctatgat ccacacaaaa acacaaagaa    27960
tgatacggag aatacaacaa taatggggga ttaacaaggg acgcaacaca atgacccgaa    28020
ggtaataaag ttttacagca ccaattacaa gcaacaggta atggagtata tttcccaatg    28080
```

| | |
|---|---|
| cgacgagaaa gccgaatgtc attcagaaca gcattgcatt ttatcttctc aaacctctta | 28140 |
| aggtgcaatt gtataaaata agaatcctta atgacagtga tgaattgagg aaaagcaaaa | 28200 |
| acaaaactag caatgtcttt gcttgtaagt ttcaaaaata tcttcatcca aatctcagtc | 28260 |
| ggtaattcaa caaaaattc aggcgcctac aaaattaatc agactaattt aatatcatct | 28320 |
| tgtaaacagc gaaagaaaa aataacacac ccaaaaataa aaaactctta cccctgttat | 28380 |
| ccatcgagat acacagaaaa attcagaaca ctcagtgtca tgtttcttaa attgttccca | 28440 |
| aagctcagac attctaagcc aaaaatttt tgagaactgc aaaaacccag tttttataac | 28500 |
| aaagccttaa tgttttctta actgatttaa ctgccctaac aggaactcca cattccggcc | 28560 |
| accgccaccc aggggacaaa tcttgccaag aactacaagt ccataaaaca acatcctgca | 28620 |
| aattatacca aaggtttcta tggtcgacac aattacaacc tgacctaaaa ggtgaataaa | 28680 |
| gcagtaaata aggatgagtt aaacaggcca cacaatgtcc agaatgtaaa aaatgctttg | 28740 |
| tttggcacca accagaccac agctgaagca aggaaaatt gtagcgaaca cattcttctc | 28800 |
| gtaatctgtt taacacagaa caacattcaa ttctggcaaa cctcttaaa aaatgttttc | 28860 |
| tgaaatattt ctttaaaatg acagtttgca actctggaaa acacaaaata aaagccgcaa | 28920 |
| tatctctact gcttaaatat aaaaatatca ttgtccaaat ttctactggt aaaactgaaa | 28980 |
| gcatcttctt cctattaaaa aaagaaaagt gttttcaaat tatattagac tctaaccaaa | 29040 |
| aaaattcaaa tacttttcct ttataatgta cattaagaat aaaaatatac tcaccgttta | 29100 |
| aaagtagaac ttaacagtat aatataaata caagtgagct gaacaacgac agccgatttc | 29160 |
| agccggagca aaattaaaaa gaataaaagg atcaaaccaa cacgtaggac agtctactcc | 29220 |
| aaaacagtaa cggcagtatg acacagaagg agaggaacta agtccaggaa acttcgcccg | 29280 |
| gtgcgataaa aagtaacgcc gccggaaagc agttgaatac aaaagaggta aaaattcacg | 29340 |
| aaaaacagaa gcaaaaacta ctaaatctgc tattggcaaa taagaaaaa tttcaaacca | 29400 |
| tatttccaaa ggaagaaaag caatcatacc gtagaagaac ctgaaggcga ccgcaaacgt | 29460 |
| gctcccgtac cacaacgtca cacgccacac ccactgggaa aacccacacg ccccgcctct | 29520 |
| gtgcaacgtt atatatatga atag | 29544 |

<210> SEQ ID NO 2
<211> LENGTH: 48
<212> TYPE: DNA
<213> ORGANISM: Artificial Sequence
<220> FEATURE:
<223> OTHER INFORMATION: Synthetic construct

<400> SEQUENCE: 2

| | |
|---|---|
| aagcttctcg agatcgatat cagatcttaa taaaaataaa gcggccgc | 48 |

<210> SEQ ID NO 3
<211> LENGTH: 32745
<212> TYPE: DNA
<213> ORGANISM: Ovine adenovirus

<400> SEQUENCE: 3

| | |
|---|---|
| ctattcatat atataacgtt gcacagaggc ggggcgtgtg ggttttttat tgtttattgt | 60 |
| catggaattt acaagaagt aagttgttgg atctttattc acaattcttt taacaatgac | 120 |
| ttttttactt attacatttt tcatcttttt tacttcacat gatattttac ttaaattttg | 180 |
| tacatacaag ccaaaattcg cataaaatgt cttacttaa aagttaaat ttttttttta | 240 |
| acgcataaat ggacgtacag cagcaattgg aatagcagga agggccattg taaagtgtgt | 300 |

-continued

```
tcctgctgat gccgctgcag aaaggataga tgctatcgta cgcataaacc cccctcctat    360
ttgttcatct gctgctttta ttatatcttc tgccaatcta ggtgatattt gcttttgaat    420
gctgtttcca aaagcttgca tcatcggatt ttcaattaaa tggattggat ttgcagaatt    480
tcctaaaaaa tagcccaacc catctaaagc agttaaaagt attctccctc caggaaccac    540
agatataatt aagcggagca accgagaggt taaattccag ggtcctccga agagagtatc    600
taggatcagg ccaagaagtg aaccaaaaag acttgtaagt agaagttgtc tgatatgctt    660
tggagaggac tgtaaaaatt gcaaaacggt atcaatgac catttcttct ttacttttac     720
atctgtatca tgttctccat cagaaggtct tattgggaag taccattggt cacgagcatc    780
tttgaagact tctgtttctt gaaattctgt tttcggtaag cgactagcag ttatggtatt    840
aggaatattg acggtaatgt tattcacatc tacaatttct ggaggaatcc atcttgcata    900
ggatgaaatg ggttttgtgg gttctttcaa tatataattg cgaggagggt ttttccaaaa    960
tctctgaaca taagtatttt ctgattttgg cggttttttg ctttttcgcg ctctttttct   1020
tggctttggt ctttgaaatt ttttcttcct ttttctgtag gctcctcctg ctaaagctgt   1080
gttatttgtg acgtacatcc tgttagctac acgattttcc cggactgcaa atttttttgc   1140
aaatggaaaa gaaattgctg aaaccttcta ttaatcatat aatttgtcag tggaatcatg   1200
aatcagatag tgcaggattt tttcttttg atactgataa tttatactat tatgtattgg    1260
atcaagtgtc ttggatatgt ttaagagata taactcttca ttgtgatcgc atgtggttag   1320
cggtttgttt tgtttgtgc aaatctaaat ttgatgtaca caatattcta gcgggagtac    1380
atgttatgta atgaaaatga cgtcggggat tgaatggatt gagccttatt tgacattttt   1440
ctgtgatttt tttgccttat taggaaataa atttgtggcg ccagtacgat ggagattgga   1500
atgactcctg catttacaga aaggaatttg tactgtgttt tgcttgactt taatttaaga   1560
tggtatcagc agatatttaa cccaatatgg attaagccaa atttatgggc tttctctgat   1620
tttttaaaaa aaatggcctt tatttatgct agcgacttgg cgttgttaaa ttcttacatc   1680
cctggtaatg tttgtaacaa acttgatatc atcaagaaag atcttcctga agattttacc   1740
gtgtctatgt tttgtgtctt agtgtgttgg cttgcttctt tctgtaaagg ttctaattta   1800
gctgaaactc gccagaattg tcacgcggta agcaaattc tggcacaact atcaaaatta    1860
ataaaaccct aattttagt ttgtaaaaat agaattcaaa ttttaacgc cacaatgact      1920
tcggcggagt tttctgttga atttccttat gtttctaagc caattgttcc atggcctgct   1980
tcggcatctt ctaataattc atcgagtcag atatattgact ttcctgttct taaaccagat  2040
caagatccaa tagccttctt tcaaactaac aatacggctt acttacaacc tggagctact   2100
tattactgga agtgtatcga actgtcaaag cctattcaca tttacggtca aggagctaca   2160
gtacaacttg tcggacctgg acctgtgttt gttttcaaca gtgaaagtgt tattcctgaa   2220
gattttacg tcgtgtttga aaatatcaac tttattgaag atgaatttcc tattagaagt    2280
ggccagttaa gttaggact tacaactcac agtgctgtat ggtttatcaa tgtatgaaa     2340
acttcaatag tcaattgtaa ctttaaaaat tttaggggag cggctctttg gtattcagat   2400
aatagaaatt tttggaatgc gagaaaatgg aatcagcagc atttagtttc aaattgtcgt   2460
tttaatggtt gtagaattgg aatttctaat actggttcat ctgaatattc catagccagt   2520
caaaatcaat tttatgattg tcaaatctgt tttaatgtaa ccgggggtaa ttggtctaga   2580
aataataatg ttattgttaa ctgtagatgt gcttatctgc atgttggaga taacatgtgg   2640
```

-continued

```
tatgaaggcc attccgaaaa taataatccc gctaagggta ctttctgcaa taacataatt    2700
aaccatgctg ataacggagg caatgtctgg cctactcagt ttaaacttac agatggatca    2760
acgatacagt tagcatcatt ttattttgat gataatcaag aaattccacc ttgttatagc    2820
ggtaattttc attggtttgg agatgtaaac attgtaaatt tttctaccac aaaaattgat    2880
aaatggtgca ttactggatg taatttctat ggtaatacac atgcagctaa cgatgctggt    2940
caagttcagg ttgctgaagc tgtaaaagac aaagtgttta ttattgggtg ttctggtaat    3000
aatgtaacca tgaaaaatat tgtagaaggt aacatgactc caaaaattgg tacaataaag    3060
taaaaaactt tttattcaaa acaaaatgga tttacattta aacgttttac atattgattc    3120
tgcgtataag ttcttttttct aaacactctt ctaatttcca tacatgcttg ataaaacaaa    3180
ctttgtaaat tcataaatat aggtttgact tgatcagaag gtgaataata gctccatcta    3240
aatgattcgg taataggaac attattatat attaaccagc tatattttga gttaactctt    3300
gcatgatcca ctatatcttt aagtacaggg ataagtgcac tcggaaatcc aaaagaatag    3360
tttttaataa atctatttat ctgtgaagaa tcaagctgcg gactaataac atgacatttt    3420
gattgaattt ttaaatcctt aatatttcct ctatcatgac gcgggttcat attatgtaaa    3480
actactacaa cagtgtaacc attacatttg gcaaatctat taaaaatttt tgacggtaaa    3540
gcatgaaaga aagaacttat agaatgcat gatcccaatt gattcataca ttcatctatt    3600
ataatacaga tagatccttc acttgcagct ctgcagaata tattatctgg attatcaata    3660
tttagattag tatcggaaat agcatctttg aaagctaatt gtataaattt tggatttaat    3720 gttttttgtta gtggattaga gaatgcatcg tagtttcctt caacacactg tgctttccac    3780 gcaattttt cttctaatgg aacagtacct ttttctggag ttatgaaaaa aattgtttct    3840
ggtattggat caattagttt tccagatata atatttctta taaattgaga ttttccgcta    3900
cctgtgggtc catatacagt aacaatgaat ggttgtaatc cgcagtttaa actgggtata    3960
cagccatctt ttaacagatt gtgagcctca tttacagttt tttgataatt tacagcaata    4020
ttgtgtaaat cagtcataag ttgaccatga tacatacatt tatcaaaaac ttcttgactt    4080
tctggaaatg gatttctgca aatagaagga tctatcttta caacatcatt tttccaattt    4140
aatgtgtcac ttaaaaattt tcccaaaaag gattttctgt caatggttct tgcggtcttg    4200
gatttgggtg tctcttgtcg tacgggtaaa gtaagtatcc tttcttccac tggatccctt    4260
tcctcatcgt ttgatccttc caaggtctca gaattctggt tagttgcttc tctaccaccg    4320
tgaatggtac atcggttcca cttgcggttt gcagtgtctt ttttaaactt ttcctcgatg    4380
tctgaaactc tttctgtggt tgttctaata aattatagtc agtaaaacaa tgttttagaa    4440
tttcatagtt taaacaattt ttagcatgac ctttggctct taattttcct tctccaataa    4500
atttacagtt tttacaagtt atgtctttta aagcatataa tttaggagct aaaatacatg    4560
tttctgaact gaatgcttca gctccgcaac ggttacaaac agtttcgcat caaccaacc    4620 aagttagaca tggatgtttt tcatcaaaga ttaaatttga gttatatttt ttaagtctat    4680
gtaatccttt tgataacatg agttggtggc ccttttctgt taagaataac gagtctgtat    4740
caccataaat acttttatc tcccttttcta tgtaaggttt acccatatct tccccatata    4800
aaatttctgc ccactcactc atgaaagctc tggtccaagc cagcacaaag gatgctatct    4860
gagttggata tcggttgttc ttgatccatt cttccttatc ctcaatagtt gttaaaatta    4920
aatcattaca atcagcagat aaaaaagtta taggcttaaa agtcacgtga tcttgatttc    4980
ctataaaaag tggaaaatta aaattttcat ttgtgtctttt ggaatctttg ggcggcattt    5040
```

```
caggtaggtt tgaaaaatac tgattccact caaatgaacg ttttggtaat gatttactaa    5100
tcacagttgt gtatgatgta atttcagctg atccattttc taatctttt  ttatctttct    5160 cttcaatatt ttcagcaaac actactttct ttttatctat acgggtagca aacgaaccat    5220
ataaagcatt tgataacaat ttacttatac ttcgctgaat cttgttgtta cttttacttg    5280
cttttctttt agccataata tttactttca catattttg  acataacggt ttccagtcac    5340
tccatacagc atacatttca gagcttttga ttattttgca tttccatcct ctattgtgta    5400
aggtgattaa atcgatagag gtcagtactt catttatcaa tgtttcattt gaccagcata    5460
actttccact ttttttagaa cataatggag gtaacacatc aagataatct aatgatgggg    5520
gttcacaatc ggctaccaca atcataggtt tgattgaatt gtcaaaataa tctatttttt    5580
cttttctttg tagtagttct tgaaagtaat ctatttgtgc attggcttca aaagcattta    5640 aagttttttcc atatggaagt ggatgcgtta aggcactagc atacattccg cagatatcat    5700
acacatatat tgcttcttca aatattccta aaaatgaagg ataacatctt cctcctctta    5760
aactcattct aacaaaatca tacattttt  ctgatggagc ttccaaattt cttaggaatt    5820
cagagggatg atcttcttca ttataaaga tttgtttaaa caatgcttga gtattactac     5880
taattgtagg acgttggaat atattaaaag aacactcaag ctttaaagat gttgtacaga    5940
actcttgata accttctata agttttcaa ctaattgagc cgtaactata acatcatcaa     6000
tacaatactc cttagcttcc tctaataagt tgtattttg gttgtgtttt ggtttgtttt     6060
gtaaatattc ttcaaatgaa ttccaatatt tttgaactgg ataaccattg ttttcttttt    6120
catattctcc caacataaaa aaatcattga ttgccctgta aggacaataa cctttgctaa    6180
cactcaactg atatgcagta gcagcgtctc ttaaagaaga gtgggttaac aaaaatgtat    6240
ccctaaccat aaattttata ccttgccatt tcatatcttc aaaattaata attccatttt    6300
tccatctttc ataagttgta tgtgaaggtt tcttaaagca aggatttgga agagataatg    6360
taatatcatt aaataacagt tttccagcac gaggcataaa gcttcttgtc agcttaaaca    6420
ttgaaagttc ttcactgtct attccttcta atacatgact tgcaagtatg atttcatcaa    6480
aaccacagat attatgacct actacatata attcaatata tcttggttcg cactgtttta    6540
attttttttc tttatttaag accatgatgt cttcatatga taaatttgat tcaagaccat    6600
gattttcaca aaacgttgac cagtattttt tagctactga aatttgtagc tctgttctga    6660
attttttaaa agctatgcca atttcatctt cttttttatt taacattaca aaacattctc    6720
tgtttacctc ataacctata tcggtagcta ttttagaagc aattttatg  agtgatttac    6780 atccaattaa cttaaaaacc aacaagtaag gagttaactg ttttccatac aaagaatggt    6840
aagtatatgt ttcaatatca taaacaataa aaagacgttt tgcttttatg gctccaactg    6900
gattaaattt gatttttcc  caccagagtt ttgtttcatg gtgaatattg tgataataga    6960
agtcccgtct tctggatgag cagttgtgta tattactata aattgttccg cagaattcac    7020 attttattctg ttgtttaaca gttttttatta aatatatttc tccttttaaa atcaataatt    7080
ctattggtaa caaatttcca ttaagaattt cttcagtcat cttaaaaaat cttttgttga    7140
acttccatat tttaaagat acgggggtgt tagaatcaca aagttttaaa acatctaaaa     7200
cattttctac tttcttgaaa gaatttaatt ttaaaccctg aattgcaaag taattataaa    7260 aactttttc  aaaattcttg tagtatataa ttttatata  tgtatcctca tatattccag    7320
taatataagt agtagttctt tgcttttatta ttgtctttga agccatctgt ttaaagccgc    7380
```

```
ttcccgtact cgctcaaagc ttcttaaaac aacttcattt gtactatagc caacaattcc    7440
agacaatttt attctaaatg ctatttcaac tgaatctaaa tctgaaaaat ccgtgtttac    7500
ttggttgatt acttcttcta tgctcccact gtcttctacg aagtctatat cttgaagtaa    7560
ttggtctctt tcttctggag ttgaaaaaga gtaagatctt tcattagctt ctataattcc    7620
taaaaaatca cgagttattc tgctatatag ttgtctgaat gcttgtgttt ctctattaaa    7680
ccaaactcta gtaaatatat cttctccatt ttcatttcta cctcttaata taatttgaac    7740
aaattggatt ccaatatttc tggcagctaa cctattttgc actaaattta agtataagta    7800
atatagcgtg cttgccacat gctctaatat aaagaaatac actaaccatt tttgaataaa    7860
atcatcagtc aatctatttt cattataaaa tctaataagt aattgaaaaa attcacttcc    7920
gtaattaaaa aaattactcc ttcttgcttc aggagttaat tcttcttcta aattttgaat    7980
taaatctact attgaagcta tcacttcatc attaaattct tccctactca gatcgcttga    8040
gctcggctcg cgatctgaaa atccttcatc ttctatttca ggaacagtaa gaggagaact    8100
agaagtttct tcaacattcc ttacccttig gcgtctatta acaggtaatc tatcaataaa    8160
tcttctgatt acatcacccc ttgaacgtct cattatttca gtaatagctc tataattttc    8220
cctaggtctt aatctgaatg gtaatcctac tcttgtccct gaccttaaag ttaatgctcc    8280
accatgcatg ccacctttc ctaaagttaa tacagttgct aaatctttta aattaattcg    8340
attttcagct tctggaattt ccagctgtga aaattcatct ataaaaagct caatccagaa    8400
ttcagaaaaa ggtaagtcta atatacattc actattatgc atgttagaca aaattaaaaa    8460
tttacataaa gcttttttaa ttttacaaat taactttata aggtaagtat ccctttcttg    8520
caaatttaaa accataaaag cttgagaaaa aggttgataa tgctgctgaa aagatctatt    8580
ctgattttga gctgaaatag cggagccaaa accttgcatg tctgcaagtt gcagactccc    8640
taatattcta tccattaaaa ccgcgttttg aatttgacta attgtttgtg aaaaattttc    8700
tacattttga attgctctca tatatgaccc agtatttatg gagtatgaac aatcagttaa    8760
aatttgccag gtcatgcgtc tctcaaaact tataggtgaa agatacaact tatatgaaat    8820
gttgctgtaa gtccgctgat caaacagata ctggtttaaa actcgcgcca cataaaaata    8880
cccaattaat aaatttggtg gaggttctcc ttcaaatggt ggttgtgaag taacaggtcc    8940
tcttgggcgt aaatcgagta attgagtcac tggataatta aaaaatcgat tagcccattt    9000
tattcccctt tcatgtatag tccttgacct ggcaatactt cgattattaa ggtcaagtgt    9060
taaacgtaaa tatcgtaagg tatgttgact ttgcccagtg agttgttgcc attggtgaat    9120
ctgcaaggca aacaaaaaat ttatcttatt actgcagatg catcctattt tacaaaattt    9180
acgttcatca ttggaaactc cagacttatc aagcaactcc ccgggcacgt caaataaaaa    9240
tgaaaaagat gaatttgaac cagcagttgg catttctagc aaaccatctg atgaatttaa    9300
tatgagacga tctcaaagag atgataattt acctaaaagt cagataccag tagtagatat    9360
actacatgat aaaaatccta aaatggcaga agaacgagac ttaatgtata aatcttctgc    9420
ttgcataaaa cttgatgatt ctaaacaatt aaaaactgat atgttcaggc cggattttgc    9480
tggaactagt ccagctcaaa gacacataga agccgcagag ctaaagagaa atggatctta    9540
tactcgtagt ttagaacaat ggacacatga ttcttttata agtcatgtta aacaattact    9600
ttctagacca tttatatctc taggtattac atatttggat gattttttgc agacttattt    9660
agatcatact gaatcgtctt ctttaaactt tcaactgttt actttaataa atcactgttc    9720
agaaaatact ttaaaacgga ttttaaaaca catttctaaa aaaaatgaaa aaaatcaata    9780
```

```
tgtaaatcaa tggttgattg atctcattac atgtatatat ctaattataa gagatgaaca   9840
aaatgttaca gaacaagtta atgccctttt agtaactagt aatcacttag ctttacattt   9900
tgcaaagaaa gctacaggtg gattctatcc tacagcagac aagttagcga agactcatat   9960
tttttttcaag agaataattt taggaatact ttcgctagca gaaagtatag gttgctatac  10020
tgtgaatcca tattgcaaaa atcctttgaa aaagtcaaaa gtagaagtag aaccaagtga  10080
cgaaatgtat atgttcagct taaaaggtgc acttgaacat cctgattccg acgaagacga  10140
agacagtgga cttcaaaatg aataattatc ataaatggac ttctaatgtt atagatgcaa  10200
ttctatcaaa caaagctctt ttagctataa aaattttaaa agtcaaccgt ttgcaaacaa  10260
attgaatgct ttagaatcag cagttgtgcc tccaagaaaa gatgatactc ctgaaatgat  10320
agcaaatctt ttaaaagaat tagttgcttt gggagctatt cgcagtgatg aagttggccc  10380
attatattct gaccttctta tcagagttca caaatataat agcttgaatg ttcaatcaaa  10440
tttgcaaact ttaacaggag acattaaatc acttcaatcc gatataatta gaagttccga  10500
tattcccaat ttaagtaatc aagttgtttt aaatacattt ttaaattctt tgccctcaac  10560
tgttacattt ggacaacata attatgaagc ttttaaacaa actctaagat tatttgttaa  10620
tgagacacct aatattacag ttttttagatc aggaaatgat actttaattc aggttaacat  10680
aacaggaatt catacaatta atttgaatga tgcatttaaa aatttaaaaa atttttgggg  10740
aatagtatta acaggtgaat ttattccagg tgatattaca agcagactaa cagctaatac  10800
aagagtactg ctttattttc ttgctccttt tacaaatgat aatacattca cacctgatac  10860
ttttctagct ttactcatga aattatatag attgacagtt tcttctgctt tagattttga  10920
agaagaaact gaagctgaag tagaaaatgt agctcaacaa ataggatcca ctagtgcaga  10980
ttttacaaag actttaggat atctattaaa aaacaaagaa gaatcatttt cgcctcccaa  11040
atcattatct cctagacaac tgggtatttt aaggttcata cagaaaagtc tggtagataa  11100
aattgataga aataatgaag atccatggga tgctttagaa actttatctt attcatttc   11160
tccgtcattt tatgaggcca atgggccttt tattagacgg ttaataactt atatggaatt  11220
tgccttacgt aattctccta cttacttcag agaaatttac tccaacaaat attggatacc  11280
acccaattca ttttggactc aaaattatgc agacttttt tcggaaaaga agaaaaaaca  11340
aaatttcgaa acatttgaac cgcgggaact tcctttacaa atctctgagg aagaagctgt  11400
cccgcataca gaagattttc agtcagccat ctcgccctct atgggccaaa cttcactccc  11460
tgctccttct gtgtcagaat acagtagcgt gcctcggtca gcttttttacc ctctcagaga  11520
acgtatccaa gagagcattt caaaggcagt catccctcct ttgacaggct atgtcggaaa  11580
acaaataggt gaaactattt tccctggtag tggagatctt gtagcacccg ctgcgtcttt  11640
agttgcagca caattggttg attcaaggtt taataacaga agacaaagat tgaaagacgc  11700
agccagaaag cgtcaccgct atgttagaga gatgcataat atttctgata aagagtcaaa  11760
tgcttctaat gatacggtaa tatcacctttt gattggacat ggttcgcgca ctgaaaatcg  11820
ttttgaatat ttgagaccta aggtggaaa ttatttatac taataaaat cataacagac  11880
ctgacgggcg gtcatccttt tttattagat gcagaaattt gtacctccac cacgaatcct  11940
tgctccaaca gagggtagaa acagtattac ttatacgcct ctggcaccac tgcaagatac  12000
aacaaaagta ttcttttattg acaataagtc ttcggacatt gaaagtttaa actttactaa  12060
taatcacagt aacttttta caaatattat tcaaaatgct gatttggcag cggatgaagc  12120
```

```
agcaacgcaa gatattaaac tggatgaaag atctagatgg ggcggtgaac tgaaaactttt    12180 tataaaaaca aattgcccca atgtttcaga attttttaac agtaatagct ttctagccag    12240
attaatggta gataaaactg atccagaaca tcctaaatac gaatgggtac aaattacaat    12300
tcctgaaggc aattacactg gaagcgaact tatagatcaa cttaacaatg gtattttaaa    12360
caattactta gaagtgggac gccaaaaagg agtagaaatt gaagacatag gagtaaaatt    12420
tgatacaaga gattttttcac ttggatatga tcctgaaacg ggactaatta ctccaggaaa    12480
atatacatat aaagcttttc atccagatat tatcttgcta cctgaatgtg gcgtagattt    12540
tacatattct agaattaata atatgttagg tataagaaag agatttccat atactaaagg    12600
atttcaaatt ttatacagtg atttgacgaa gggaaatatc tctccattac tgaatttaaa    12660
taactatcct cattctatcg aacctgtaat gcaagacgaa aatggagtta gctataatgt    12720
agaaaaaata agtgacaatc cccccagatg gcaaacaaag tacagatctt ggactttaag    12780
ttataaaaat aatggaggag ctaaagccct aactgtacta actgttccgg acataacagg    12840
aggattaggt caaatttatt ggtcaatgcc agatactttt aaagcaccta ttacttttac    12900
taacaatact acaaagccag aaacacttcc aattgttgga ttacatatgt ttccttttaaa    12960 agcagggtta gttcataata taaatgcggt ttattctcaa cttttggaac aaattacaaa    13020
tacaactcaa gtattcaata gatttcctaa aaatgctata ctaatgcaac caccttacag    13080
caccgtaaca tggataagtg aaaatgtccc ctttgttgca gatcacggga ttcagccatt    13140
aaaaaacagc cttacaggtg tacaaagagt tactataaca gacgacagaa ggagatcttg    13200
tccatacata cagaaatctt tggcgactgt tgtccctaaa gtactttcaa gtgctacact    13260
tcagtaacaa tctggctgat atctctgggc cttatcctcc tggaaccgtt atgtctattt    13320
tagttagtcc ctctgataat accgggtggg gtattggaac atcaagtatg agggctactg    13380
gcttgaaatt ttctaaaaaa caacctgtta gagtgcgacc ttattacaga gctcagtggg    13440
gacagcttaa tgctcgtact tcacttgaga aactaaaaac caaattgaaa tattatgaaa    13500
aattgtacag ggacagacta aaagaaaaa cagttgttcc aaagaaaaag aggtcaccta    13560
catctcctgc ggatcgactt aaaaaatatc ttaaagctgt cagtcaaatc aaagctttca    13620
atagagctag aagagcagcc caataaatat tatttttcac ttgcagatga aggtagttca    13680
cgtgcttaaa tctcctcatc gtcgaagaca tacacgtcgt tacaaaaaac taaaaaaaat    13740
caatctatct ccatacattt tacctaaaga attgcaaggc ggttttttac cagctctcat    13800
tcctatcata gcagccgcaa ttagcgcagc ccctgctata gctggaactg taatagctgc    13860
taaaaatgct aatcgttctt aaaattttaga aactttttt tttaacagat cacatggctt    13920
tttcaagatt agctccccat tgcggcttaa cacctgttta tggccacacc gttggaatct    13980
gtgatatgag aggaggtttc agctggtcta gtttgggaaa ttctttttact tctggtttaa    14040 gaaacatagg ttcatttata tcaaatactg ctcaaaaaat aggtcaatca caaggatttc    14100
agcaagccaa acaaggtcta ctgcaatcaa atgttttaga aaatgcagga caattagcag    14160
gtcaaacttt aaatactttg gtagatattg gaagattaaa ggtagagaaa gatctagaaa    14220
aattgaaaca aaaagttata gggaacgacc aacaaattac tcaagaacaa ttagctcaac    14280
taatagccag cttaaaacca aaagatgaaa tgtttgtaaa gcaatcagaa aaaattgttg    14340
aacctatgag accagaaatt aaatctagcc aaatgcctgt agaaatgtct tttatgatt    14400 ctgtaagtga tgaaccaatc ataaaaacca agaagttag ccctcctcca ttttcatctg    14460
aatcttcaca ttcatattct cacccaagaa aaagaaaacg cgtatccggt tggggtgcat    14520
```

```
ttttggataa catgactgga gatggagtaa attttaatac aagaagatat tgttattaaa    14580 aacactttt atttacagat ggagccacag cgtgaatttt ttcacattgc gggtagaaat    14640
gcaagggaat acttgtctga aaatctggta caattcatct ctgccactca aagttttttt    14700
aatcttggag aaaaatttag agatcctttt gtagctccat cgacgggtgt aactactgac    14760
cgttctcaga aacttcaact tcgtatagtt ccgattcaaa ctgaggacaa tgaaaacttt    14820
tacaaaacta gatttacttt aaatgtagga gataacagag ttgcagatct tggaagtgca    14880 tatttttgaca ttgaaggagt tattgataga ggacctactt ttaaaccttta tggagggaca   14940 gcttataatc cattagcccc aaaatcagct tttcccaatg cagcttttat ggatactgat    15000
gaagctacaa caatttatat tgctcaactc cctaatgctt ataatgctca aaacaaaggt    15060
gtagaagaag caattcgagt agaagcaaac actactactc ctaatcctca atcaggagaa    15120
tatgctactt atgactctgc caaatttaat ccagaaacta ctggtgcttc tggaaggctt    15180
ttaggaatta atagcttagg agatcttttt ccggcttatg gatcttattg tagacctcaa    15240
tcagcagatg gtaacatttc aactgcaccc ataactaaag tctatctaaa cactactgct    15300
acagatgaca gggtcagtgg agttactgca gttgacaccg caaccagatt gcatccagat    15360
gctcattata ttgaatatac tgatgaagcc aaagctacag ctataggaaa tcgcccaaat    15420
tatattggtt tccgagacaa ttttattgga ctcatgttct acaataatgg ttctaatgca    15480
ggaacatttt ccagccaaac acaacaactt aatgttgttt tagacttgaa tgacagaaac    15540
agtgaactaa gctatcaata tctaatagca gatctgacag ataggtatag atattttgca    15600
ctttggaacc aagcagttga tagttacgac cagtatgtca gaattttgca taatgaagga    15660
tatgaagaag cccctccggc cttatcattt ccttctcaag gtatccaaaa ttatttcatg    15720
cctactgcgg caggtaatgc gatgacagta gacacgggta gaaatactgc agcaaaaaca    15780
gataacacca aggcttttat aggatatggc aacatgccat ctttggaaat gaatctgaca    15840
gcaaatctac aacgtacatt tttgtggtct aatgtagcaa tgtatctgcc agataggctg    15900
aaaacaacac cacccaacat aaatctacct gatgacacca actcttacgg atatataaat    15960
ggaagggtcc ctctagcaaa cataatagat acatggacta acattggggc taggtggtca    16020
ttagatgtta tggatactgt aaatccattt aatcaccaca gaaattcagg actaaagtat    16080
aggtcacaac tgttaggaaa tggaagatat tgcagatttc acattcaagt acctcaaaaa    16140 tttttttccta taaaaatct tttgttgctg ccaggaacat ataattatga atggtacttt    16200
agaaaggatc ccaacatggt ttttcagtct actttaggta acgaccttag agcagatggc    16260
gcaactatta catacaccaa cataaattta tatgtttcat ttttccctat gaattatgaa    16320
acagtaagtg aacttgaatt gatgttgcgt aatgctacta atgatcaaaa ctttgcagat    16380
tatttgggtg cggtaactaa tctttatcaa atcccagcta atacaaatac tgtagtagtg    16440
aacgtaccag atagatcttg gggtgctttc agaggatgga gtttcaatag aattaaagct    16500
tcagaaacac ctatgatagg agcaacaaaa gatccaaatt ttacttattc aggatctata    16560
ccgctactag atggtacttt ctatttaaca cacacttttc aacgagtttc tattcagtgg    16620
gattctagcg ttccatggcc aggagatgat aggcttttga ttccaaattg gtttgaaatt    16680
aagagagatc ctaaatatgga cgcagaaggt tatactatga gtcaaagtac tatcacaaaa    16740
gatttttatt tggtacaaat ggctgctaat tataatcaag cttatcaagg ttataaattg    16800
ccagtacatt ctaaatatta tggattttta gaaaattttc aacctatgag tcgccaagta    16860
```

```
ccaatttatg gtaatggcac ttatgattta tatactgctt atattacaaa ccaaagaacc    16920
atgcaaattt ggaataatag tggtttagaa tctaaaactt caaatcctcc tatgttatcc    16980
aacactggtc atctttatgt agctaactgg ccatacccct tgattggacc aaatgctatt    17040
gaaaaccaac aaactgaaag gaaattttg tgtgataagt atatgtggca gataccattt    17100
tctagtaatt ttttgaatat gggtaattta acagatttag ggcaaagtgt tttgtacact    17160
aattctagtc attcacttaa tatggttttt actgtggata gtatgcctga aacaacttat    17220
ctaatgcttt tatttggtgt tttcgaccaa gttgttatta atcaaccaac aagaagtgga    17280
ataagtgtag cttatttgcg ccttcctttt tcagctggta gtgcagcaac atgagcggca    17340
catccgaaag tgagctgaaa aatctgattt catcattaca tttaaataat ggatttttgg    17400
gcatttttga ttgcagattt ccaggttttc tgcaaaaatc taaaattcaa actgctatta    17460
ttaatacagg tcccagagaa caaggcggaa tacactggat aacattagca ttagaaccca    17520
tttcttataa gctatttata tttgatccac tcggatggaa agacactcaa ttaattaaat    17580
tttataattt ttcactaaat tctcttatta aaggtcggc cttaaataac tcagacagat    17640
gtattacagt agaaagaaat actcaaagtg ttcaatgtac ctgtgcggga tcgtgcggct    17700
tgttttgtat attttcctta tactgttttc acttttataa acaaaatgta tttaaaagtt    17760
ggcttttcca aaaattaaac ggttcaaccc cttctctgat cccatgtgaa ccacatctat    17820
tacatgaaaa ccagacattt ctttatgatt ttttaaatgc aaaaagtgtt tattttcgaa    17880
aaaattatag aacatttatt gaaaatacta agactggatt aataaaaaca cattaattgt    17940
attcttgctt tttgacgttt tcattagtct tcatcttcat cttcttcttc actgctagat    18000
tccaagatgg ttttttttt ctttgatgga gtaggctctt caatagttcc aaaaggattc    18060
atatcagaat cctcttctat gttaggcaac atagtatttt taacctggaa tgactgattc    18120
cacttaaatt gagaaaactg aattggaatg ttatttccca tacattcatt ccaaaattta    18180
cgcacaagag ttaaacactg taacatatct ggcaagctaa ttttcatctc acaaaatttt    18240
ccattattac gtctcaagtt gtattgatag ttacaacatt gaaacacaaa acagcaggg    18300 aatgtaactg ctgcggcctg aactctatta acatcctgaa catcaattcc ttccactcca    18360
gatatagaaa atggagttat tttagggagt tgttttccta ttgtttgttt gccaccataa    18420
ttacattcac actgacccaa tataaaaagc atatttccga ctttagcttt cggaaacaca    18480
gcttttgtag tttcaatggc attttgcata gccagcaagg ccttcttttc atctgaaaag    18540
ttaagaccac aactgcgagg agaacattgc ccaaaacgct gatgggcatc ctcagcacat    18600
aacacgtaat gttcctgaac tatttttact acttgtttat tcatacgccc attactaaga    18660
acacccctcc cttcctttag ggcttgcacc cctgcttccg atgttggagg catttcaatt    18720
tcattcaccc ttttaaacat gaagtcacca tgaaaacatc taggacggtc ctcctcccaa    18780
tcatgatacc acaaataaca accagaagca ttaaagtttg gaatcaagtc aatttgctta    18840
caaattgcac tatatagcat tctacctcct acagtagcca tagatttact gctactataa    18900
gtcaaattta aattttcat cttttcatg tactgagcaa ataattttc acaatctcct    18960 tcttcaggat gaaacttcat ttgactggta tcaactttaa cacactctcc aaatttagct    19020
aaaatttcga gcgccgcttg aactttattc tgaaattctt ctgtagtaga ttttctcttc    19080
ttgatagatt tagtaacttt tttagaagac attatgttag ttttttttctc gttgtaggat    19140 ggctgaaaaa aatatgggag agtcagagaa gggtttgaac gaagaagaat ttaactctat    19200
tctatcaaaa catctggaaa gacaaattaa aatctgtaaa gcgttaacat caaaattatc    19260
```

```
gaactggaat attggaacat tgttagaaaa cttgttatttt tgtcctgatg aaagacaatc   19320
atcaggtgat cccgacccaa aactaaactt ttatccgcct tttttaattc cggaatgtct   19380
tgcattgcac tatccatttt ttctaacaac tcctattccg ctatcatgca aagcgaacaa   19440
aataggaact aacacttacc gaaaatggat gaacaatcaa gtcctggatt tacaaatacc   19500
ttccttggaa aattgcaaat gggatgatag cttgggaaat gtagatttaa ttgaagagct   19560
taaagagaac caaaaacttg ttttagtaaa acaagaccat gaaagaaata tatggtttaa   19620
atcaaaatgc aaacaacttc aaagtttcag ctatccctca ctcagtctgc ccccagtttt   19680
acaacaagtt ttaattgaat ctcttatcgg cattagtcag gatcctaata actttgacaa   19740
aaattacgaa cctgcaataa ctctagaaaa actacaacat gtaaactgtg atcaagattt   19800
aaaacaagtt caacaaaaag tatcttcagc cgctacatac ggaatacttt tgaaatgcat   19860
tcagacttta ttcagtgaca aattattcat tcaaaactgc caggaatcat tacattacac   19920
cttaaccat ggttatgtaa aattacttca attttttgaca aatgtcagtt taagcgaatt   19980
tgtaactttc catggtttaa cacacaggaa cagactcaat aatccgcagc aacatacaca   20040
attggcaacc gaagacaaaa tagactatat catagataca gtgtatttat ttttggtatt   20100
tacgtggcag acagcaatgg atatttggaa tcaaacatta tgatgataaaa caataaaatat   20160
aattaaagag gaattaaacc aaaattttga gaaaattgtc aaagctgaat cagttgatga   20220
agtttctgaa attttaaagt ctattatttt ccctgaactc atgctgcgag ctttttgttc   20280
taatttacct gatttttataa atcagagtca gatatcaaat tttagaaact ttatctgcat   20340
taaatccggc ataccgcagt caatttgccc cctattacct tcagatctaa ttccttttaac   20400
tttcctagaa agtcatccaa tactctggag tcatgtaatg ttactaaatc ttgcttcatt   20460
tctagtaaac caaggcaatt atttgcatga acccgaaaaa cctttaaata tttcatcagt   20520
ttactgtaat tgtaatttat gctctccgca aagaatgcca tgttacaata gcagtttgat   20580
gcaagaaata ctaaccattg ataaattcga gttcacaaac tctgataaaa caaaacagct   20640
aaaactgacc ctccaaactt tgctaatgc ctatcttaac aaatttaact cagcagaatt   20700
ctaccatgac caagttttat tctacaaaaa ctgtaaaagt aaattttcta accaattaac   20760
agcttgtgta ataaaagacg aaaaattatt ggctaaaata gcagaaattc aaataacgcg   20820
ggaaaaagaa ctcttaaaaa gaggaaaagg aatttatttg gatccagaaa caggagaaat   20880
cttaaacaat ggagaagcca tatcatcctc tgaaaacttc caaaggcaaa gaactagcta   20940
tgctctacca tcaaatgaag gagagcgagc tggatgggaa gccgatgagc gaagaagacg   21000
aaggagaagt gagtgaggat gaaacagaga caacaattcc aaagaaaatg aagtttacaa   21060
gtaagtaagc tctaaatttt ttatattaaa aactgaattt ttttagacaa aattatttta   21120
aattaaatct ttatagctag cagttgatct ttgttcgttt ttcagaaaac tcaagtgttc   21180
agtcatatca agttcacttg cctctgaaac acgaaattgc ggaaattcta gaaaaaatta   21240
gactagaatc taaaaaatat ccaggaaaag tttatcaaat aagaaatagaa actccagcaa   21300
gtattacaaa acgatacctg tatgaaagag atctgaagaa actgttccag tatctagaag   21360
acgcaaagaa gctttacgct aagtaccaaa gctgaggctt tatagttttta aatttttcccg   21420
ccatggctca accagtgacg ccttacgtct ggaaatacca accagaaaca ggatatactg   21480
ctggagccca tcaaaattat aacactgtta tcaactggtt gcatgccaat ccacaaatgt   21540
ttgccagaat tcaacatata aacaccgcac gcaatgttat ggacaaattc cgctctgatt   21600
```

```
tgacccgaga tgacatcgcg gttaacatca acaactggcc tgcagaggat ttaatgcaac    21660
ctcctaattt tccttacatt cctgcgacct ctaaatccgc ttcaaccata aatgactggt    21720
tggctaccac tcaaggaatt caactcagtg gaactagtga actaaacggg tgggatcta     21780 accgcctgac ttcctatccg gatattccac ccatttttaaa gtatgaaagg cctggtcaac   21840
aacttcaagg ccaaggactt tttaagcaag aaaatattca tttatttttac gaatctccgc   21900 gcctccctcg ctctggagga ttaactcccc aacaatttgt aaaagaattt ccgcctgttg    21960
tttataataa ccccttctca gaatctatga gtgtatttcc gaaagaattt agtcctttgt    22020
ttaacccttc agaatctttg aaaaaaacat ccagtcaaac tttacaatat aaataaaaaa    22080
cttctattga tctttatact tacactaaag catcgcgttt attttcgtcg ccataaaaat    22140
atatcaaaga cccgtaattc tctaacttta aatcattttt tgaactaatc ttaatccatt    22200
taaatgtagg aattaatata tcagaaacca gtaacaagcc agaattaaaa tatacttgtg    22260
tcatttttac agatgaagcg agcacgctgg gacccggttt atccctttttc tgaagagaga    22320 ctggttcctc tgcctccttt tattgaagcc ggaaaagggc taaaaagcga agggttgatc    22380
ttatctttaa actttactga tcctatcact ataaatcaaa ccggtttctt aactgtaaaa    22440
ttgggagatg gaatattcat aaacggagag ggtggcctat caagcactgc tccaaaagtc    22500
aaagttcccc tgactgtctc agatgaaaca ttgcaactgc tattaagtaa ttctctaaca    22560
actgagtcag actctttagc tttaaaacaa ccgcaacttc ccctaaaaat aaatgatgag    22620
gggagtttag tattgaactt aaatactcct ttaaatctac aaaatgagag attgagttta    22680
aatgtttcaa atccactaaa gatagcggca gattcttttaa ctataaactt aaaggaaccc    22740
ctaggattgc aaaatgaaag tttgggctta aatctaagtg atcctatgaa ataactcca     22800 gaaggaaatt taggtattaa attgaaaaat cctatgaaag ttgaagaaag ttcctttagcc   22860 ttaaactata agaatcctct cgccattagt aatgatgcgt taagtataaa cattgcgaat    22920
ccattaactg ttaatacaag cggatctcta ggaatatctt attctactcc cttacgaatt    22980
tcaaataatg ctttatcatt atttatagga aaacctttag gattaggaac tgacggctct    23040
ttaactgtaa atttaactag gcctctggta tgtcgtcaga acactttggc cataaactac    23100
tcagccccac tagtgtcatt gcaagacaat cttactttaa gttatgctca accattaact    23160
gtaagcgata attcttttaag attgtctcta aattctccac taaacacaaa tagtgatgga    23220
aaacttagtg taaactattc taatcctttta gttgtgactg actctaatct taccctcagt    23280
gttaaaaaac ctgtaatgat taacaacaca ggtaatgttg acttaagctt tacagctccc    23340
ataaaattaa atgatgcaga acagttgact ttagaaacca ctgagcccct ggaagtggcc    23400
gataacgctc taaaactgaa acttggaaaa ggcttaactg ttagtaataa tgctttaacc    23460
ttaaaccttg gaaacggttt gacttttccaa caaggtctttt tacaaattaa aactaatagc    23520
tctctagggt ttaatgcttc tggggaatta tcaacagcta caaagcaggg aaccataacc    23580
gttaactttc taagcacaac tcctatagct tttgggtggc aaataatacc tactactgta    23640
gctttcattt atattttatc aggaacacaa tttactcctc aatccccagt aacttcttta    23700
ggttttcaac ccccacaaga cttttttggat ttcttcgttt taagtccgtt tgttacatct    23760
gtaactcaaa ttgtgggaaa tgatgttaag gttattggcc taactatttc taaaaaccaa    23820
tctaccataa ctatgaaatt tacttctccc ttagctgaaa atgtaccagt tagtatgttt    23880
acagcacatc aattcagaca atgaatattt taaaaattct ttattaaaga gtaatctttt    23940
tacataccgt tcttgacata atgtgcctct ataattaaca aatctaagca agcaaggttg    24000
```

```
atcattggaa tctatagaag cataactctt ccaataagca taatcatatg gcggtaaatg    24060
aaaaccccct aaatctacca tattcatctt taagtgtaca gtatctaaca ggtttttaca    24120
atcttgcact tctggacttt taaaaacaaa cagtactttc ataggacaac aattgtaacg    24180
gttataatct gttacaattt tacttatttc ttcttccaat ggcaaagcat tccaaagtct    24240
tgttataagt actgtaaaat catcaaatga ataacataac acatttgtac aacaattggt    24300
ccaaggtaaa aaaacaggca cacgaacatg aacttttttt aaaattaaca tcagtgtctg    24360
ttttaaactt tgacattgca aagaatttgg ctgcaagcaa tgacaatgaa attgattttg    24420
ctgacaaggt aagtcacaca aatacaactt taacagccta aatataacga cattaatgta    24480
actttccaag actttaaaac taacaaacgg tatatcacaa taaaaaagat gatgaatccc    24540
ttcgcaacac ataatggagt tcatgctaca tccaaagatg gttccgacaa acctctgtaa    24600
attaaagaac aacaatacaa catacgaaga aaattaaaac gttttcaaa acgagatata    24660 cattgctgca aagtatctga acatttacat tttatactta taagctcaca gtttcagaa    24720 aatgtaattc gtttaacagt ttgatatgaa taccattttg aagaaaaatc atcttccatc    24780
actccagaaa ataaaaaata gaaatgagtt ttgtgcattt gtgaagctcc cagaaacatt    24840
aacggacagc aaatccaagt attacaacaa acaggaacag tcttaacgtt tcgttcagaa    24900
aacaaagtaa caggcatatg attaaagcaa gacaataaaa cactttggc agctaaacat    24960 tgcaaagatc caggtgaatt acaatgacaa tgataataaa acttataagc catatcggcc    25020
ctcttgcaaa acgaatcagc ttttggctt ataggaaaat aacaaaaaaa ctgattatat    25080
atgaatggag ttaatatctt cttcaaatta tacacacgaa tagcagaacc aagacgacca    25140
cgcccaacac aggtaaatat ttcaagtcca tgactaggaa cagatggttt ctcacaagca    25200
acaactttga tttgcttatc catcactgcc aatcaggctt aataggaaaa gaagaaaaat    25260
aattttccca ataataacga aagaaattcc acgtttcatc ctgtacatta ctagtcacaa    25320
atacaacctc cgctatcaaa gattccctat catttaaaac tcccaccaaa ttgtcccagt    25380
ctacctcaaa aaagccagtt cccatatttt caaaatttgc ccatttaaa aatcccaaag    25440 catcaaattc aggaaacaaa tctttctgag ctaaaacata tacagtttta tcgccattaa    25500
atctaaaagc catcctaaat ggacctctag cccagtagtt taagtaccgg gaagagacta    25560
tacaatatac ttgatattga tgtctgttaa gtggtgataa aaagaaagt aattcagaat    25620 taggataaag cattctccca tgttgattca tctacaaaaa acaaaaaaat tataaggttc    25680
atagaaaacc tactatttaa caaatctata aaatgcatt aaaaagttac cttgaatata    25740
aattcagatc acctaaaaaa cgaaaaaaaa taacatttat gttagtaaat gatagtctt    25800 aaaaattaga aaagaatcaa gtcgcttta tacttacaaa ctccaaataa attctgtaac    25860
caagagaaaa attgtaacct aaaaggtaaa gaagaacatt ataagattaa aaccactcta    25920
aaatctgaaa agcattatga aaaattctga tagctgcaac ttactagtct tctccaaatg    25980
ttgcaggcat ttcaaaaaat caagaggaaa accggagttt ataaagtagt agtctgatta    26040
tatctgaaaa agtttaactt ccttttcaac ccaacccagt ccaataaaat tccaacctta    26100
acttctttcc tgctaaaact ccataaaagt ccaattacca cttgactttt atttaacctc    26160
aattatgtta catgttattc tacccataaa aacttgatga ccaagaactg acctttccca    26220 tgttttctg aaataacaaa aatgttgatt taaagatttt taactaccca aaaaacccgc    26280
tctcatgatt ttttcttata taaacaggat acaaagaac tggcaaagat attccatcat    26340
```

```
acttctccaa ctgtcaaaac ataccactta acctctccca tgttttttcc cttttgcaca      26400
aacaggatat aaaaaatatt tttgccacaa tgttttcct tttactcaac tgccagaata       26460
aaaatgaaca gcttaacctt tttccctctt aacccattgc gttcctctaa gaaaaaaatt      26520
atcccgccca atatgctaaa ggcttctccc gccaaaacag ctcaacttaa aatctctcat     26580
gaataaaacc cagagaaaat ttccagtaat aaaaattaat aaccgtgaag tactagatct     26640
aataatgata ttttgaactc ataaaaatcc accatccatg taatgttaca aacactttt      26700 tattgagttt tttcttacaa ctgcattaca tacaggccaa gcatcaaaact ttcttctgta    26760 tttcttccta gaccacaaaa ttacagactt atatttctgc cacaaatctc tatgatcttt     26820
acagtaacac ttcatttaa atggggaata cagcagcaaa taaggatgag ttaaacatgc      26880
gatacaatga ccagaaggaa gataatacaa tacatcacac caaatgaag gtacagacaa     26940 catcgcatga aatcttaaat gtgattttac aataaatttc tgcagcagct tacaatctat    27000
attagcaaac cgttttatat acaaacataa aaacttggaa cttttcacca actcaatcat    27060
gttattataa cacattacaa attttgctat atctttattt gtcaaataac aaaatatctc    27120
aatccacagc tcatctggca gcaaacttcg caaatccatg acctgtaaaa gatacaacag   27180
aaaacagaaa attaatgcca ttcaataaca taaaaatac agtcaaatca catactttt      27240 ctcacttaca aaactttgtg agcaggcctc caaaacaaac ttcagaaaat ggatgcatac    27300
aagaacattc tcctctcaaa aattgcttta actgaatgcg gcattttgca cctccagaaa    27360
aatgcagtcc attgagaggc tcttctctta aaacacagaa atgcttctgc aaaatctgta    27420
aagaaactaa caacttccaa attccaatca tcatgcattg caaagaagga cattcaacag    27480 caaaggatc gtgatgagcc aataaagctt tactgtatga ctcattttca tgaattacag     27540
tctgtaactt actataatgc attttaagct ctgcttcaca aattaataat gctaatttct    27600
ttaagcagct caaagaaaac tcatcaggac aacggcattt aagaaagcaa caaaatgatt    27660
tcttaaaata cattttttcca gcatgatgaa caataaaaaa tttcaacgtt aaacaatgca   27720
aaaatgcatt tttatgcaca gtgaaagtaa ttttttcagc tgaagctaaa tcacagccta    27780
ttttattaca tgattttgta tgctccaaaa gagcttgttt taattgcttc aaatccatct    27840
tcttacaatt ttttcttttt ataaacacca gaaccgcatt caggccaatt ccagttattg    27900
tttaaatttg ctacagaaac tgcagaccac aaaaccacat cctctaaatc aacccacaaa    27960
gatctatgat ccacacaaaa acacaaagaa tgatacggag aatacaacaa taaatgggga    28020
ttaacaaggg acgcaacaca atgacccgaa ggtaataaag ttttacagca ccaattacaa    28080
gcaacaggta atggagtata tttcccaatg cgacgagaaa gccgaatgtc attcagaaca    28140
gcattgcatt ttatcttctc aaacctctta aggtgcaatt gtataaaata agaatcctta    28200
atgacagtga tgaattgagg aaaagcaaaa acaaaactag caatgtcttt gcttgtaagt    28260
ttcaaaaata tcttcatcca aatctcagtc ggtaattcaa caaaaaattc aggcgcctac    28320
aaaattaatc agactaattt aatatcatct tgtaaacagc gaaagaaaa aataacacac    28380 ccaaaaataa aaaactctta cccctgttat ccatcgagat acacagaaaa attcagaaca    28440
ctcagtgtca tgtttcttaa attgttccca aagctcagac attctaagcc aaaaattttt    28500
tgagaactgc aaaaacccag ttttttataac aaagccttaa tgttttctta actgatttaa   28560
ctgccctaac aggaactcca cattccggcc accgccaccc aggggacaaa tcttgccaag    28620
aactacaagt ccataaaaca acatcctgca aattatacca aaggtttcta tggtcgacac    28680
aattacaacc tgacctaaaa ggtgaataaa gcagtaaata aggatgagtt aaacaggcca    28740
```

```
cacaatgtcc agaatgtaaa aaatgctttg tttggcacca accagaccac agctgaagca   28800
aaggaaaatt gtagcgaaca cattcttctc gtaatctgtt taacacagaa caacattcaa   28860
ttctggcaaa cctctttaaa aaatgttttc tgaaatattt ctttaaaatg acagtttgca   28920
actctggaaa acacaaaata aaagccgcaa tatctctact gcttaaatat aaaaatatca   28980
ttgtccaaat ttctactggt aaaactgaaa gcatcttctt cctattaaaa aaagaaaagt   29040
gttttcaaat tatattagac tctaaccaaa aaaattcaaa tacttttcct ttataatgta   29100
cattaagaat aaaatatac tcaccgttta aagtagaac ttaacagtat aatataaata    29160
caagtgagct gaacaacgac agccgatttc agccggagca aaattaaaaa gaataaaagg   29220
atcaaaccaa cacgtaggac agtctactcc aaaacagtaa cggcagtatg acacagaagg   29280
agaggaacta agtccaggaa acttcgcccg gtgcgataaa aagtaacgcc gccggaaagc   29340
agttgaatac aaaagaggta aaaattcacg aaaaacagaa gcaaaaacta ctaaatctgc   29400
tattggcaaa taagaaaaa tttcaaacca tatttccaaa ggaagaaaag caatcatacc    29460
gtagaagaac ctgaaggcga ccgcaaacgt gctcccgtac cacaacgtca cacgccacac   29520
ccactgggaa aacccacacg ccccgcctct gtgcaacgtt atatatatga ataggtaccc   29580
tttgttccct ttagtgaggg ttaattccga gcttggcgta atcatggtca tagctgtttc   29640
ctgtgtgaaa ttgttatccg ctcacaattc cacacaacat acgagccgga agcataaagt   29700
gtaaagcctg gggtgcctaa tgagtgagct aactcacatt aattgcgttg cgctcactgc   29760
ccgctttcca gtcgggaaac ctgtcgtgcc agctgcatta atgaatcggc caacgcgcgg   29820
ggagaggcgg tttgcgtatt gggcgctctt ccgcttcctc gctcactgac tcgctgcgct   29880
cggtcgttcg gctgcggcga gcggtatcag ctcactcaaa ggcggtaata cggttatcca   29940
cagaatcagg ggataacgca ggaaagaaca tgtgagcaaa aggccagcaa aaggccagga   30000
accgtaaaaa ggccgcgttg ctggcgtttt tccataggct ccgcccccct gacgagcatc   30060
acaaaaatcg acgctcaagt cagaggtggc gaaacccgac aggactataa agataccagg   30120
cgtttccccc tggaagctcc ctcgtgcgct ctcctgttcc gaccctgccg cttaccggat   30180
acctgtccgc ctttctccct tcgggaagcg tggcgctttc tcatagctca cgctgtaggt   30240
atctcagttc ggtgtaggtc gttcgctcca agctgggctg tgtgcacgaa ccccccgttc   30300
agcccgaccg ctgcgcctta tccggtaact atcgtcttga gtccaacccg gtaagacacg   30360
acttatcgcc actggcagca gccactggta acaggattag cagagcgagg tatgtaggcg   30420
gtgctacaga gttcttgaag tggtggccta actacggcta cactagaagg acagtatttg   30480
gtatctgcgc tctgctgaag ccagttacct tcggaaaaag agttggtagc tcttgatccg   30540
gcaaacaaac caccgctggt agcggtggtt ttttgtttg caagcagcag attacgcgca    30600
gaaaaaaagg atctcaagaa gatcctttga tcttttctac ggggtctgac gctcagtgga   30660
acgaaaactc acgttaaggg attttggtca tgagattatc aaaaaggatc ttcacctaga   30720
tccttttaaa ttaaaaatga agttttaaat caatctaaag tatatatgag taaacttggt   30780
ctgacagtta ccaatgctta atcagtgagg cacctatctc agcgatctgt ctatttcgtt   30840
catccatagt tgcctgactc cccgtcgtgt agataactac gatacgggag ggcttaccat   30900
ctggccccag tgctgcaatg ataccgcgag acccacgctc accggctcca gatttatcag   30960
caataaacca gccagccgga agggccgagc gcagaagtgg tcctgcaact ttatccgcct   31020
ccatccagtc tattaattgt tgccgggaag ctagagtaag tagttcgcca gttaatagtt   31080
```

```
                                                 -continued
tgcgcaacgt tgttgccatt gctacaggca tcgtggtgtc acgctcgtcg tttggtatgg    31140
cttcattcag ctccggttcc caacgatcaa ggcgagttac atgatccccc atgttgtgca    31200
aaaaagcggt tagctccttc ggtcctccga tcgttgtcag aagtaagttg gccgcagtgt    31260
tatcactcat ggttatggca gcactgcata attctcttac tgtcatgcca tccgtaagat    31320
gcttttctgt gactggtgag tactcaacca agtcattctg agaatagtgt atgcggcgac    31380
cgagttgctc ttgcccggcg tcaatacggg ataataccgc gccacatagc agaactttaa    31440
aagtgctcat cattggaaaa cgttcttcgg ggcgaaaact ctcaaggatc ttaccgctgt    31500
tgagatccga ttcgatgtaa cccactcgtg cacccaactg atcttcagca tcttttactt    31560
tcaccagcgt ttctgggtga gcaaaaacag gaaggcaaaa tgccgcaaaa aagggaataa    31620
gggcgacacg gaaatgttga atactcatac tcttcctttt tcaatattat tgaagcattt    31680
atcagggtta ttgtctcatg agcggataca tatttgaatg tatttagaaa aataaacaaa    31740 tagggggttcc gcgcacattt ccccgaaaag tgccacctga cgtctaagaa accattatta    31800
tcatgacatt aacctataaa aataggcgta tcacgaggcc ctttcgtctc gcgcgtttcg    31860
gtgatgacgg tgaaaacctc tgacacatgc agctcccgga gacggtcaca gcttgtctgt    31920
aagcggatgc cgggagcaga caagcccgtc agggcgcgtc agcgggtgtt ggcgggtgtc    31980
ggggctggct taactatgcg gcatcagagc agattgtact gagagtgcac catatgcggt    32040
gtgaaatacc gcacagatgc gtaaggagaa ataccgcat caggaaattg taaacgttaa    32100
tattttgtta aaattcgcgt taaattttg ttaaatcagc tcattttta accaataggc    32160 cgaaatcggc aaaatccctt ataaatcaaa agaatagacc gagatagggt tgagtgttgt    32220
tccagtttgg aacaagagtc cactattaaa gaacgtggac tccaacgtca aagggcgaaa    32280
aaccgtctat cagggcgatg gcccactacg tgaaccatca ccctaatcaa gttttttggg    32340
gtcgaggtgc cgtaaagcac taaatcggaa ccctaaaggg agcccccgat ttagagcttg    32400
acggggaaag ccggcgaacg tggcgagaaa ggaagggaag aaagcgaaag gagcgggcgc    32460
tagggcgctg gcaagtgtag cggtcacgct gcgcgtaacc accacacccg ccgcgcttaa    32520
tgcgccgcta caggcgcgt cgcgccattc gccattcagg ctgcgcaact gttgggaagg    32580
gcgatcggtg cgggcctctt cgctattacg ccagctggcg aaaggggggat gtgctgcaag    32640 gcgattaagt tgggtaacgc cagggttttc ccagtcacga cgttgtaaaa cgacggccag    32700
tgaattgtaa tacgactcac tatagggcga attcgagctc ggtac                   32745
```

<210> SEQ ID NO 4
<211> LENGTH: 12
<212> TYPE: PRT
<213> ORGANISM: Artificial Sequence
<220> FEATURE:
<223> OTHER INFORMATION: Derived from Ovine Adenovirus
<220> FEATURE:
<221> NAME/KEY: MISC_FEATURE
<222> LOCATION: (5)..(6)
<223> OTHER INFORMATION: X = A, R, N, D, C, Q, E, G, H, I, L, K, M, F,
    P, S, T, W, Y OR V

<400> SEQUENCE: 4

His Cys His Cys Xaa Xaa Pro Gly Ser Leu Gln Cys
1               5                   10